(12) United States Patent
Bryhn et al.

(10) Patent No.: US 8,618,165 B2
(45) Date of Patent: Dec. 31, 2013

(54) COMPOUNDS

(75) Inventors: Morten Bryhn, Svelvik (NO); Jan Kopecky, Prague (CZ); Anne Kristin Holmeide, Oslo (NO)

(73) Assignee: Pronova Biopharma Norge AS, Baerum (NO)

( * ) Notice: Subject to any disclaimer, the term of this patent is extended or adjusted under 35 U.S.C. 154(b) by 0 days.

(21) Appl. No.: 13/225,855

(22) Filed: Sep. 6, 2011

(65) Prior Publication Data

US 2012/0065260 A1   Mar. 15, 2012

Related U.S. Application Data

(63) Continuation of application No. 12/111,589, filed on Apr. 29, 2008, now Pat. No. 8,034,842, which is a
(Continued)

(30) Foreign Application Priority Data

May 4, 2005 (SE) ........................ 0501044
May 4, 2005 (SE) ........................ 0501045

(51) Int. Cl.
*A61K 31/20* (2006.01)
*A61K 31/22* (2006.01)
*A23D 9/00* (2006.01)

(52) U.S. Cl.
USPC ............................. 514/549; 514/560; 554/224

(58) Field of Classification Search
USPC ................... 514/549, 560; 554/224
See application file for complete search history.

(56) References Cited

U.S. PATENT DOCUMENTS

| 2,836,628 A | 5/1958 | Miller |
| 4,132,719 A | 1/1979 | Mohrbacher et al. |

(Continued)

FOREIGN PATENT DOCUMENTS

| EP | 1 300 470 A1 | 4/2003 |
| EP | 1 310 249 A1 | 5/2003 |

(Continued)

OTHER PUBLICATIONS

Berger, A. et al., "Structural Requirements of Sphingosylphosphocholine and Sphingosine-1-phosphate for Stimulation of Activator Protein-1 Activity," *Molecular Pharmacol.* (1996) 50:451-457.

(Continued)

*Primary Examiner* — Deborah D Carr
(74) *Attorney, Agent, or Firm* — Finnegan, Henderson, Farabow, Garrett & Dunner, LLP

(57) ABSTRACT

Compounds of formula (I);

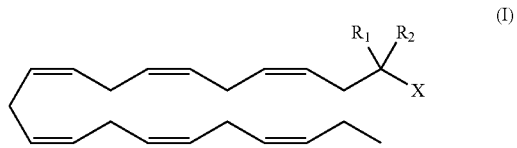

wherein $R_1$ and $R_2$ are the same or different and may be selected from the group consisting of a hydrogen atom, a hydroxy group, an alkyl group, a halogen atom, an alkoxy group, an acyloxy group, an acyl group, an alkenyl group, an alkynyl group, an aryl group, an alkylthio group, an alkoxycarbonyl group, an alkylsulfinyl group, an alkylsulfonyl group, an amino group, and an alkylamino group; and X represents a carboxylic acid group, a carboxylate group, or a carboxamide group;

or any pharmaceutically acceptable salt, solvate, complex or pro-drug thereof, with the provisos that the compound of formula (I) is not (all-Z)-4,7,10,13,16,19-docosahexaenoic acid (DHA), alpha-methyl DHA, alpha-methyl DHA methyl ester, alpha-methyl DHA ethyl ester or alpha-hydroxy DHA ethyl ester, are disclosed.

A fatty acid composition and a pharmaceutical composition comprising such compounds are also disclosed. The use of such compounds as medicaments, in particular for the treatment of diabetes type 2, is also disclosed.

50 Claims, 13 Drawing Sheets

Related U.S. Application Data

(63) continuation of application No. 11/417,252, filed on May 4, 2006, now Pat. No. 7,550,613.

(60) Provisional application No. 60/677,351, filed on May 4, 2005, provisional application No. 60/677,350, filed on May 4, 2005.

(56) References Cited

U.S. PATENT DOCUMENTS

| | | |
|---|---|---|
| 4,264,517 A | 4/1981 | Liang |
| 4,647,685 A | 3/1987 | Bonjouklian et al. |
| 5,422,371 A | 6/1995 | Liao et al. |
| 5,502,077 A | 3/1996 | Breivik et al. |
| 5,656,667 A | 8/1997 | Breivik et al. |
| 5,698,594 A | 12/1997 | Breivik et al. |
| 6,365,628 B1 | 4/2002 | Berge |
| 6,689,812 B2 | 2/2004 | Peet et al. |
| 6,905,850 B2 | 6/2005 | Irimescu et al. |
| 7,550,613 B2 * | 6/2009 | Bryhn et al. ............... 554/85 |
| 8,034,842 B2 * | 10/2011 | Bryhn et al. ............... 514/560 |
| 2004/0162348 A1 | 8/2004 | Peet et al. |
| 2006/0135610 A1 | 6/2006 | Bortz et al. |
| 2010/0035990 A1 | 2/2010 | Bryhn et al. |
| 2011/0166228 A1 | 7/2011 | Holmeide et al. |

FOREIGN PATENT DOCUMENTS

| | | |
|---|---|---|
| EP | 1 426 047 A1 | 6/2004 |
| EP | 1 466 597 A1 | 10/2004 |
| EP | 1 544 281 A1 | 6/2005 |
| GB | 2 323 594 A | 9/1988 |
| JP | 56-108721 | 8/1981 |
| JP | 57-149400 | 9/1982 |
| JP | 57-150392 | 9/1982 |
| JP | 59-204175 | 11/1984 |
| JP | 61-103826 | 5/1986 |
| JP | 63-88159 | 4/1988 |
| JP | 64-083031 | 3/1989 |
| JP | 05-000974 | 1/1993 |
| JP | 06-240289 | 8/1994 |
| JP | 6-293789 | 10/1994 |
| JP | 7-53488 | 2/1995 |
| JP | 10-195023 | 7/1998 |
| JP | 2002-180082 | 6/2002 |
| JP | 2004-182674 | 7/2004 |
| JP | 2004-525180 A | 8/2004 |
| JP | 2003-283858 | 2/2005 |
| WO | WO 97/44063 | 11/1997 |
| WO | WO 99/26620 | 6/1999 |
| WO | WO 99/26661 | 6/1999 |
| WO | WO 02/052955 A1 | 7/2002 |
| WO | WO 02/083122 A1 | 10/2002 |
| WO | WO 03/092673 A1 | 11/2003 |
| WO | WO 2004/012727 A1 | 2/2004 |
| WO | WO 2004/043894 A1 | 5/2004 |
| WO | WO 2004/071504 A1 | 8/2004 |
| WO | WO 2004/078166 A2 | 9/2004 |
| WO | WO 2004/085582 A2 | 10/2004 |
| WO | WO 2005/060954 A1 | 7/2005 |
| WO | WO 2006/117664 A1 | 11/2006 |
| WO | WO 2006/117668 A1 | 11/2006 |
| WO | WO 2007/107869 A2 | 9/2007 |
| WO | WO 2007/116027 A1 | 10/2007 |
| WO | WO 2010/006085 A1 | 1/2010 |

OTHER PUBLICATIONS

Bonjouklian, R. et al., "Studies of the Antitumor Activity of (2-Alkoxyalkyl)- and (2-Alkoxyalkenyl)phosphocholines," *J. Med Chem.* (1986) 29:2472-2477.

CAPlus Abstract for Kaufmann, H. P. and Kirschnek, A., "Fatty aldehydes. IV. Preparation of fatty aldehydes containing more than one double bond," *Fette, Seifen, Anstrichmittel* (1958) 60:1125-1132.

CAPlus Abstract, AN 1996:483717, for Kuklev, D. V., et al., "Synthesis of C2-elongated polyunsaturated fatty acids," *Bioorganischeskaya Khimiya* (1996) 22(3):219-222.

Cateni, F. et al., "Total Synthesis of a Natural Cerebroside from Euphorbiaceae," *Helv. Chim. Acta* (2007) 90:282-290.

Combs, Colin K., et al., "Inflammatory Mechanisms in Alzheimer's Disease: Inhibition of β-Amytoid-Stimulated Proinflammatory Responses and Neurotoxicity by PPAR, Agonists," *The Journal of Neuroscience* (2000) 20(2):558-567.

Copending U.S. Appl. No. 12/446,249, filed Apr. 20, 2009.
Copending U.S. Appl. No. 12/446,615, filed Apr. 22, 2009.
Copending U.S. Appl. No. 12/447,092, filed Apr. 24, 2009.
Copending U.S. Appl. No. 12/740,377, filed Apr. 29, 2010.

Desarnaud, F., et al., "Anandamide Amidohydrolase Activity in Rat Brain Microsomes," *Journal of Biological Chemistry* (1995) 270(11): 6030-6035.

Eichelberger, U. et al., "Synthesis of analogues of the 2-O-alkyl glycerate part of the moenomycins," *Tetrahedron* (2002) 58:545-559.

English abstract of JP 05-000974.
English abstract of JP 06-240289.
English abstract of JP 10-195023.
English Translation of JP 2003-283858.

Flock, Solveig, et al. "Syntheses of Some Polyunsaturated Sulfur and Oxygen-containing Fatty Acids Related to Eicosapentaenoic and Docosahexaenoic Acids" *Acta Chemica Scandinavica* (1999) 53:436-445.

Granlund, L. et al., "Effects of structural changes of fatty acids on lipid accumulation in adipocytes and primary hepatocytes," *Biochimica et Biophysica Acta* (2005) 1687:23-30.

International Search Report for PCT/IB2007/003305 (U.S. Appl. No. 12/446,615) dated Mar. 20, 2008.

International Search Report for PCT/IB2007/004588 (U.S. Appl. No. 12/447,092) dated Nov. 21, 2008.

International Search Report for PCT/IB2007/004613 (U.S. Appl. No. 12/446,249) dated Apr. 16, 2009.

International Search Report for PCT/IB2008/003666 (U.S. Appl. No. 12/740,377) dated Mary 24, 2009.

Itoh, T. et al., "Synthesis of docosahexaenoic acid derivatives designed as novel PPARγ agonists and antidiabetic agents," *Bioorganic & Med. Chem.* (2006) 98-108.

Kato, T. et al., "Abnormal Catabolites of Unsaturated Fatty Acids by in Vitro Reaction of Crude Enzyme from Infected Higher Plants," *Chem. Lett.* (1994) 4:761-762.

Kaufmann, H. P. and Kirschnek, A., "Fatty aldehydes. IV. Preparation of fatty aldehydes containing more than one double bond," *Fette, Seifen, Anstrichmittel* (1958) 60:1125-1132.

Kinsho, T. and Mori, K., "Synthesis of 3-Deoxy Analogs of Sphingolipids," *Agric. Biol. Chem.* (1989) 53(10):2785-2790.

Kuklev, D. V., et al., "Synthesis of C2-elongated polyunsaturated fatty acids," *Bioorganischeskaya Khimiya* (1996) 22(3):219-222.

Larsen, L. N. et al., "α- and β-Alkyl-Substituted Eicosapentaenoic Acids: Incorporation into Phospholipids and Effects on Prostaglandin H Synthase and 5-Lipoxygenase" *Biochemical Pharmacology* (1998) 55(4):405-411.

Larsen, Laita, et al. "Sulfur-Substituted and α-Methylated Fatty Acids as Peroxisome Proliferator-Activated Receptor Activators" *Lipids* (2005) 40(1):49-57.

Magrioti, V. et al al., "Synthesis and in Vivo Anti-Inflammatory Activity of Long-chain 2-Amino-alcohols," *Bioorg. & Med. Chem. Lett.* (2003) 13:375-377.

Mangold, H. K., "Syntheses of Unsaturated Fatty Aldehydes," *J. Org. Chem.* (1959) 24:405-407.

Meyer A. et al., "Biosynthesis of Docosahexaenoic Acid in *Euglena gracilis*: Biochemical and Molecular Evidence for the Involvement of a Δ4-Fatty Acyl Group Desaturase" *Biochemistry* (2003) 42(32):9779-9788.

Nishikawa, M. et al., "Low-calorie omega-3 fatty acid glyceride health food," Database CAPLUS Chemical Abstracts XP002518330, STN Database Accession No. 2002:480253.

Notice of Allowance dated Jun. 8, 2011, from U.S. Appl. No. 12/111,589.

Office Action dated Jul. 24, 2008, from U.S. Appl. No. 11/417,252.
Office Action dated Nov. 29, 2007, from U.S. Appl. No. 11/417,252.

(56) References Cited

OTHER PUBLICATIONS

Office Action dated Aug. 6, 2009, from U.S. Appl. No. 12/111,589.
Office Action dated Apr. 14, 2010, from U.S. Appl. No. 12/111,589.
Office Action dated Jul. 14, 2010, from U.S. Appl. No. 12/111,589.
Pfeffer, P. E. et al., "α Anions of Carboxylic Acids. V. A Simple High Yield Presentation of α-Alkylhydracrylic Acids and α-Alkylacrylic Acids," *J. Org. Chem.* (1972) 37(8):1256-1258.
Sinha, S. C. and Keinan, E., "Total Synthesis of (+)-Aspicilin. The Naked Carbon Skeleton Strategy vs the Bioorganic Approach," *J. Org. Chem.* (1997) 62:377-386.
Tockizawa, K. et al., "Effects of phospholipids containing docosahexaenoic acid on differentiation and growth of HL-60 human promyelocytic leukemia cells," *J. Jpn. Oil Chem. Soc.* (1997) vol. 46, pp. 383-390.
Vaagenes, H. et al., "Low Doses of Eicosapentaenoic Acid, Docosahexaenoic Acid, and Hypolipidemic Eicosapentaenoic Acid Derivatives Have No Effect on Lipid Peroxidation in Plasma" *Lipids* (1998) 33(11):1131-1137.
Vaagenes, Hege et al. "Methylated Eicosapentaenoic Acid and Tetradecylthioacetic Acid: Effects on Fatty Acid Metabolism" *Biochemical Pharmacology* (1999) 58:1133-1143.
van der Linde, R. et al., "Synthesis of 2-substituted *cis*-8,*cis*-11,*cis*-14-eicosatrienoic acids, precursors for 2-substituted prostaglandins," *J. Royal Netherlands Chem. Soc.* (1975) 94(12):257-261.
Van Dorp, D. A. "Essential Fatty Acids and Prostaglandins," *Acta Biologica et Medica Germanica* (1976) 35(8-9):1041-1049.
Williams, J. et al., "Quantitative method for the profiling of the endocannabinoid metabolome by LC-Atmospheric Pressure Chemical Ionization-MS," *Anal. Chem.* (2007) vol. 79, pp. 5582-5593.
Willson, Timothy M., et al., "The PPARs: From Orphan Receptors to Drug Discovery," *Journal of Medicinal Chemistry* (2000) 43(4):527-550.
Written Opinion for PCT/IB2007/003305 dated Mar. 20, 2008.
Written Opinion for PCT/IB2007/004588 dated Nov. 21, 2008.
Written Opinion for PCT/IB2007/004613 dated Apr. 16, 2009.
Banker, G.S. and Rhodes, C.T., *Modern Pharmaceutics: Third Edition, Revised and Expanded*, Marcel Dekker, New York, 1996, pp. 451, 596.
English Abstract of JP 57-149400.
English Abstract of JP 59-204175.
English Abstract of JP 63-88159.
English Abstract of JP 6-293789.
English Abstract of JP 7-53488.
English Abstract of JP 2002-180082.
English Abstract of JP 2004-182674.
English translation of Japanese Office Action in related application, JP 2008-509528 dated Dec. 6, 2011.
International Preliminary Report on Patentability for PCT/IB2006/001155 (U.S. Appl. No. 11/417,252) dated Nov. 6, 2007.
International Preliminary Report on Patentability for PCT/IB2007/003305 (U.S. Appl. No. 12/446,615) dated Jan. 26, 2009.
International Preliminary Report on Patentability for PCT/IB2008/003666 (U.S. Appl. No. 12/740,377) dated May 4, 2010.
International Preliminary Report on Patentability for PCT/IB2007/004588 (U.S. Appl. No. 12/447,092) dated Mar. 27, 2009.
International Preliminary Report on Patentability for PCT/IB2007/004613 (U.S. Appl. No. 12/446,249) dated May 5, 2009.
International Search Report for PCT/IB2006/001155 (U.S. Appl. No. 11/417,252) dated Aug. 10, 2006.
International Search Report for PCT/IB2011/000250 (U.S. Appl. No. 13/574,132) dated May 31, 2011.
Meyer, U. A., "Overview of Enzymes of Drug Metabolism," *J. Pharmacokinetics and Biopharmaceutics* (1996) 24(5):449-459.
Notice of Allowance dated Feb. 10, 2009, from U.S. Appl. No. 11/417,252.
Notice of Allowance dated Oct. 17, 2012, from U.S. Appl. No. 12/446,615.
Office Action dated Jun. 27, 2011, from U.S. Appl. No. 12/446,615.
Office Action dated Feb. 3, 2012, from U.S. Appl. No. 12/446,615.
Office Action dated May 17, 2012, from U.S. Appl. No. 12/447,092.
Office Action dated Oct. 24, 2012, from U.S. Appl. No. 12/447,092.
Supplementary European Search Report; EP 06 74 4648 dated Jun. 9, 2010.
Vaagenes, H. et al., "Methylated Eicosapentaenoic Acid and Tetradecylthioacetic Acid: Effects on Fatty Acid Metabolism," *Biochemical Pharmacology* (1999) 58:1133-1143.
West, Anthony R., *Solid State Chemistry and Its Applications*, Wiley, New York, 1988, pp. 358, 365.
Willumsen, N., et al., "On the effect of 2-deuterium- and 2-methyl-eicosapentaenoic acid derivatives on triglycerides, peroxisomal β-oxidation and platelet aggregation in rats," *Biochimica et Biophysica Acta* (1998) 1369:193-203.
Wolff, M. E., *Burger's Medicinal Chemistry and Drug Discovery*, Fifth Ed., vol. 1: Principles and Practice, Wiley, New York, 1995, pp. 975-977.
Ackman, R.G. In *Nutritional Evaluation of Long-Chain Fatty Acids in Fish Oil*, edited by Barlow. S.M. and Stansby., M.E., Academic Press, London, 1962, pp. 25-29.
Bittman, R. et al., "Interaction of Cholesterol with Sphingomyelin in Monolayers and Vesicles," *Biochemistry* (1994) 33(39):11776-11781.
Boger, D. et al., "60-Kato Heterocycle Inhibitors of Fatty Amide Hydrolyase: Carbonyl Group Modification and α-Substitution," *Bioorganic & Medicinal Chemistry Letters* (2001) 11(12):1517-1520.
Cravatt, B.F. et al., "Structure Determination of an Endogenous Sleep-inducing Lipid, *cis*-9-Octadecenamide (Oleamide): A Synthetic Approach, to the Chemical Analysis of Trace Quantities of a Natural Product." *Journal of American Chemical Society* (1996) 118(3):580-590.
Czeskle, B.A, et al., "Total Synthesis of the Archaebacteriai $C_{40}$-Diol and its Enantiomer Based on (*R*)-5-Acetoxy-4-methylpentanoic Acid," *Mendeleev Commun.* (1993) 93-96.
English Abstract of JP 56-108721.
English Abstract of JP 57-150392.
English Abstract of JP 61-103826.
English Abstract of JP 64-083031.
English Machine Translation of JP 2004-525180 A.
Joseph, J.D. and Ackman, R.G. "Capillary Column Gas Chromatography Method for Analysis of Encapsulated Fish Oil and Fish Oil Ethyl Esters: Collaborative Study," *J. AOAC Int.* (1992) 75(3):488-506.
Kawate, T. et al, "Synthesis Sphingosine Analogues: Stereoselective Synthesis of 3-Deoxysphingosine and *cis*-Isomers," *Chem. Pharm. Bull.* (1997) 45(12):2116-2118.
Kimura, T. et al., "Synthesis of All the Stereoisomers of 13,17-Dimethyl-1-tritriacontene and 13,17-Dimethyl-1-pentatriacontene, the Contact Sex Pheromone Components of the Female Tsetse Fly, *Glossina austeni*," *European Journal of Organic Chemistry* (2001) 17:3385-3390.
Kley, J. et al., "Synthesis and $PLA_2$-Inhibitory Properties of 2(*R*)-Acetamido-Alkylphosphamethanols with a Variable Aggregate Anchor," *Bioorganic & Medicinal Chemistry Letters* (1999) 9:261-264.
Lerner, R. et al. "Cerebrodiene: A brain lipid isolated from sleep-deprived cats," *Proceedings of the National Academy of Sciences of the United States of America* (1994) 91(20):9505-9508.
Li, M. & Xu, G., "Chemical Constituents of the Essential Oil from *Dendrobium nobile* Lindi," *Youji Huazue* (1991) 11:219-224.
Nakajima, K., "Microbial Transformation of Isoprenoid Hydrocarbons and Related Compounds," 219-230, in *Bioreactors & Transformations* (Moody, G. & Baker, P., eds. 1988).
Nakamura, Y. & Mori, K. "Synthesis of the Enantiomers of *anti*-2,6-Dimethylheptane-1,7-diol Monotetrahydropyranyl Ether and Their Conversion into the Enantiomers of the Sex Pheromone Components of the Apple Leafminer, *Lyonetia prunifoliella*," *European Journal of Organic Chemistry* (2000) 15:2745-2753.
Office Action dated Apr. 3, 2013, from U.S. Appl. No. 12/740,377.
Office Action dated Jul. 3, 2013, from U.S. Appl. No. 13/225,855.
Office Action dated Nov. 9, 2012, from U.S. Appl. No, 12/446,249.

(56) References Cited

OTHER PUBLICATIONS

Pfeffer, J. et al. "Highly Efficient Enzymatic Synthesis of 2-Monoacylglycerides and Structured Lipids and Their Production on a Technical Scale," *Lipids* (2007) 42:947-953.

Quero, C. et al., "New Fluorinated Derivatives as Esterase Inhibitors. Synthesis, Hydration and Crossed Specificity Studies," *Bioorganic & Medicinal Chemistry* (2003) 11(8):1047-1055.

Shimizu, M. & Yoshioka, H., "Highly Selective Ring Opening of Epoxides with Silicon Tetrafluoride: Preparation of Fluorohydrins." *Tetrahedron Letters* (1988) 29(33):4101-4104.

Stumpp, M. & Schmidt, R., "Synthesis on Moenocinol," *Tetrahedon* (1986) 42(21):5941-5948.

Sugiura, T. et al. "Evidence that 2-Arachidonoylglycerol but not N-Palmitoyiethanolamine or Anandamide is the Physiological Ligand for the Cannabinoid CB2 Receptor," *Journal of Biological Chemistry* (2000) 275(1):605-612.

Tokumasu, M. et al., "Synthesis, and Structure-Activity Relationship to Novel Terpenoids from Sea Sponges," *Symposium on the Chemistry of Natural Products* (1998) 40:691-696.

Wallace, P. & Minnikin, D., "Synthesis of (2R, 4R,S)- and (2S; 4R,S)-dimethyldocosanoic Acids." *Chemistry & Physics of Lipids* (1994) 72(1):87-101.

Wang, T. et al., "Analysis of the Essential Oil from *Dracocephalum purdomii*," *Natural Product Rasearch & Development* (2002) 14(6):20-21, 30.

Xiao, J. et al., "Extraction of Volatile Oil from *Marchantia* Convoluta by $CO_2$ Supercritical Fluid Extraction and Analysis by GC-MS," *Traditional Chinese Drug Research & Clinical Pharmacology* (2005) 16(3):191-194.

Zaknun, J. et al., "Effect of Monounsaturation of a Branched Fatty Acid on Organ Selectivity," *Journal of Nuclear Medicine* (1995) 36(11):2062-2068.

* cited by examiner

Free fatty acid concentrations of the different PRBs in liver tissue from animals given 1,5% of PRB-1,2,5, and 7

DHA concentrations in liver tissue from animals given 1,5% of PRB -1,2,5,and 7

COMPOUNDS

This is a continuation of application Ser. No. 12/111,589, filed Apr. 29, 2008, now U.S. Pat. No. 8,034,842, which is a continuation of application Ser. No. 11/417,252 filed on May 4, 2006, which issued as U.S. Pat. No. 7,550,613, which claims the benefit of priority to Swedish Application Nos. 050145-9 and 050144-2, and U.S. provisional application nos. 60/677,351, and 60/677,350, all of which were filed May 4, 2005.

TECHNICAL FIELD

The present invention relates to compounds of the general formula (I):

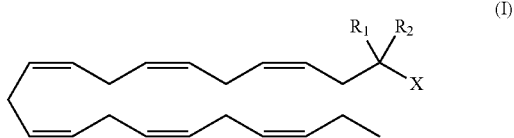

and their use as medicaments, in particular for the treatment of diabetes mellitus, type 2, and pre-stages thereof. It also relates to a pharmaceutical composition comprising compounds of formula (I), as well as to a fatty acid composition comprising compounds of formula (I).

BACKGROUND OF THE INVENTION

The increasing incidence of type 2 diabetes mellitus worldwide poses an immense public health and medical challenge for the implementation of successful preventive and treatment strategies. The concurrent rise in overweight and obesity, which is tightly correlated to type 2 diabetes, interferes with diabetes treatment and increases the likelihood of hypertension, dyslipidemia, and atherosclerosis related diseases.

The pathophysiologic condition precluding the development of type 2 diabetes is related to reduced effects of insulin on peripheral tissues, called insulin resistance. These tissues are mainly muscle, fat and liver. Muscle tissue is the main tissue concerned by insulin resistance in type 2 diabetes. The syndrome characterised by insulin resistance, hypertension, dyslipidemia and a systemic proinflammatory state, is referred to as metabolic syndrome. The prevalence of metabolic syndrome in the adult population in developed countries is 22-39% (Meighs 2003)

Currently the most promising approach to mitigate and deter the metabolic syndrome is lifestyle intervention with weight reduction, decreased consumption of saturated fat, increased physical activity in combination with appropriate pharmacotherapy. Healthy diets that avoid excess energy intake encompass substitution of mono and polyunsaturated fatty acids in exchange for saturated fat. In particular the long-chain omega-3 fatty acids from fatty fish, namely eicosapentaenoic acid (EPA) and docosahexaenoic acid (DHA) have proven beneficial in prevention of type 2 diabetes.

EPA and DHA have effects on diverse physiological processes impacting normal health and chronic disease, such as the regulation of plasma lipid levels, cardiovascular and immune function, insulin action and neural development and visual function. Firm evidence exist for their beneficial role in the prevention and management of coronary heart disease, dyslipidemias, type 2 diabetes, insulin resistance, and hypertension (Simonopoulos 1999; Geleijnse 2002; Storlien 1998).

Recent studies suggest that omega-3 fatty acids serve as important mediators of gene expression, working via nuclear receptors like the peroxisome proliferator-activated receptors (PPARs) controlling the expression of the genes involved in the lipid and glucose metabolism and adipogenesis (Jump 2002). PPARs are nuclear fatty acid receptors that have been implicated to play an important role in obesity-related metabolic diseases such as hyperlipidemia, insulin resistance, and coronary heart disease.

The three subtypes, $\alpha$, $\gamma$, and $\delta$, have distinct expression pattern and evolved to sense components of different lipoproteins and regulate lipid homeostasis based on the need of a specific tissue. PPAR$\alpha$ potentiates fatty acid catabolism in the liver and is the molecular target of the lipid-lowering fibrates. PPAR$\gamma$ on the other hand is essential for adipocyte differentiation and mediates the activity of the insulin-sensitizing thiazolidinediones (the glitazones) through mechanisms not fully understood. (Chih-Hao 2003; Yki-Järvinen 2004)

Recently, pharmaceuticals acting as ligands to the PPAR$\gamma$ receptor have been introduced as treatment of type 2 diabetes (Yki-Järvinen 2004). These compounds called thiazolidinediones or glitazones are drugs that reverse insulin resistance which is the pathophysiologic basis for development of the metabolic syndrome and type 2 diabetes. These compounds, of which rosiglitazone and pioglitazone have been launched as pharmaceuticals, lower fasting and postprandial glucose concentrations (which is being manifest as a pathologic glucose tolerance test), plasma insulin as well as free fatty acid concentrations. In this respect the glitazones act as insulin sensitizers.

However, these improvements are generally accompanied by weight gain and an increase in the subcutaneous adipose-tissue mass (Adams 1997). The use of thiazolidinediones is not only associated with weight gain but a subgroup of patients also have fluid retention and plasma volume expansion, leading to peripheral oedema. The increase in body weight and oedema has been associated with an increase in the incidence of heart failure, which is the reason why the Food and Drug Administration has included a warning in the prescription information for rosiglitazone (provided by Avandia) and pioglitazone (provided by Takeda). These adverse effects restrict the use of the glitazones especially in patients with coronary heart conditions. Clearly there is a potential for new drugs with positive effects on insulin resistance but with weight reduction activity and no fluid retention tendency.

The effect of the poly-unsaturated fatty acids (PUFAs) on PPARs are not only a result of fatty acid structure and affinity to the receptor. Factors contributing to the composition of the intracellular non-esterified fatty acids (NEFA) levels are also important. This NEFA pool is affected by the concentration of exogenous fatty acids entering the cell and the amount of endogenous synthesised fatty acids, their removal via incorporation into lipids as well as their oxidation pathways. (Pawar 2003)

Although omega-3 fatty acids are weak agonists of PPARs, when compared with pharmacological agonists like the thioglitazones, these fatty acids have demonstrated improvement in glucose uptake and insulin sensitivity (Storlien 1987). It has been reported that adipocytes were more insulin sensitive and transported more glucose when the polyunsaturated to saturated fatty acid ratio in the diet was increased (Field 1990). Collectively, these data indicate that the 20- and 22-carbon fatty acids, namely EPA and DHA could play a preventive role in the development of insulin resistance.

Due to their limited stability in vivo and their lack of biological specificity, PUFAs have not achieved widespread use as therapeutic agents. Chemical modifications of the n-3 polyunsaturated fatty acids have been performed by several research groups in order to change or increase their metabolic effects.

For example, the hypolipidemic effects of EPA was potentiated by introducing methyl or ethyl in α- or β-position of EPA. (Vaagenes 1999). The compounds also reduced plasma free fatty acid while EPA EE had no effect.

In a recent work published by L. Larsen (Larsen 2005) the authors show that the α-methyl derivatives of EPA and DHA increased the activation of the nuclear receptor PPARα and thereby the expression of L-FABP compared to EPA/DHA. EPA with an ethyl group in the α-position activated PPARα with equal strength as α-methyl EPA. The authors suggest that delayed catabolism of these α-methyl FA may contribute to their increased effects due to decreased β-oxidation in mitochondria leading to peroxisomal oxidation.

Alpha-methyl EPA has been shown to be a stronger inhibitor of platelet aggregation than EPA, both in vitro (Larsen 1998) and in vivo (Willumsen 1998).

Patent Abstract of Japan, publication number 05-00974 discloses DHA substituted in alpha-position with an OH-group, however only as an intermediate. No examination as to possible pharmaceutical effects of this compound is disclosed.

Laxdale Limited has also described the use of alpha substituted derivatives of EPA in the treatment of psychiatric or central nervous disorders (U.S. Pat. No. 6,689,812).

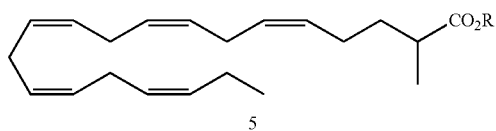

R = H, CH$_3$, CH$_2$CH$_3$ (A) α-methyl EPA

None of these modified fatty acids have, however, shown satisfactory pharmaceutical activity, and none of them has reached the pharmaceutical market.

SUMMARY OF THE INVENTION

The aim of the present invention is to provide new DHA-derivatives having therapeutical activity.

Based on the present invention a number of aspects are presented in the appended claims. Some of these aspects are;
1. Novel compounds, i.e. certain α-substituted polyunsaturated fatty acid derivatives.
2. The novel compounds for use as a medicament and for use in therapy.
3. A fatty acid composition or a pharmaceutical composition comprising the novel compounds.
4. A fatty acid composition comprising the novel compounds for use as a medicament and for use in therapy.
5. Use of the novel compounds for the production of a medicament for the prevention and/or treatment of diabetes in humans or an animal.
6. Use of the novel compounds for the production of a medicament for the treatment and/or prevention of obesity or an overweight condition.
7. Use of the novel compounds for the production of a medicament for controlling body weight reduction and/or for preventing body weight gain.
8. Use of the novel compounds for the production of a medicament for the treatment and/or prevention of amyloidos-related diseases.
9. Use of the novel compounds for the production of a medicament for the treatment or prophylaxis of multiple risk factors or cardiovascular diseases.
10. Use of the novel compounds for the production of a medicament for the prevention of stroke, cerebral or transient ischaemic attacks related to atherosclerosis of several arteries.
11. A method for specific treatment of a diabetic condition, preferably type 2 diabetes.
12. A method for controlling body weight reduction, for preventing body weight gain and/or for the treatment and/or the prevention of obesity or an overweight condition.
13. A method for the treatment and/or prevention of amyloidos-related diseases.
14. A method for the treatment or prophylaxis of multiple risk factors for cardiovascular diseases.
15. A method for the prevention, of stroke, cerebral or transient ischaemic attacks related to atherosclerosis of several arteries.
16. Processes for preparing novel fatty acid analogous according to the invention.

The present invention relates to a compound of formula (I):

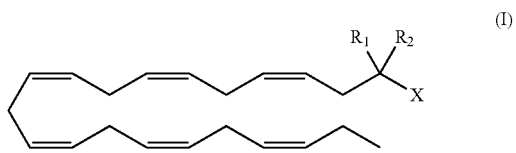

wherein
R$_1$ and R$_2$ are the same or different and may be selected from the group consisting of a hydrogen atom, a hydroxy group, an alkyl group, a halogen atom, an alkoxy group, an acyloxy group, an acyl group, an alkenyl group, an alkynyl group, an aryl group, an alkylthio group, an alkoxycarbonyl group, an allylsulfinyl group, an alkylsulfonyl group, an amino group, and an alkylamino group; and
X represents a carboxylic acid group, a carboxylate group, or a carboxamide group,
or any pharmaceutically acceptable salt, solvate, complex or pro-drug thereof, with the provisos that:
the compound of formula (I) is not (all-Z)-4,7,10,13,16, 19-docosahexaenoic acid (DHA), alPha-methyl DHA, alpha-methyl DHA methyl ester, alpha-methyl DHA ethyl ester, or alpha-hydroxy DHA ethyl ester.
The provisos correspond to the following cases:
when R$_1$ is a hydrogen atom, then R$_2$ is not a hydrogen atom;
when R$_2$ is a hydrogen atom, then R$_1$ is not a hydrogen atom;
when R$_1$ is a methyl group, then R$_2$ is not a hydrogen atom, and X is not a carboxylic acid group, a methyl-carboxylate, or an ethylcarboxylate;
when R$_2$ is a methyl group, then R$_1$ is not a hydrogen atom, and X is not a carboxylic acid group, a methyl-carboxylate, or an ethylcarboxylate;

when $R_1$ is a hydroxy group, then $R_2$ is not a hydrogen atom, and X is not an ethylcarboxylate; and when $R_2$ is a hydroxy group, then $R_1$ is not a hydrogen atom, and X is not an ethylcarboxylate.

In a compound according to the invention, said alkyl group may be selected from the group consisting of methyl, ethyl, n-propyl, isopropyl, n-butyl, sec.-butyl, n-hexyl, and benzyl; said halogen atom may be selected from the group consisting of fluorine, chlorine, bromine, and iodine; said alkoxy group may be selected from the group consisting of methoxy, ethoxy, propoxy, isopropoxy, sec.-butoxy, phenoxy, benzyloxy, $OCH_2CF_3$, and $OCH_2CH_2OCH_3$; said acyloxy group may be selected from acetoxy, propionoxy, and butyroxy; said alkenyl group may be selected from the group consisting of allyl, 2-butenyl, and 3-hexenyl; said alkynyl group may be selected from the group consisting of propargyl, 2-butynyl, and 3-hexynyl; said aryl group is a phenyl group; said alkylthio group may be selected from the group consisting of methylthio; ethylthio, isopropylthio, and phenylthio; said alkoxycarbonyl group may be selected from the group consisting of methoxycarbonyl, ethoxycarbonyl, propoxycarbonyl, and butoxycarbonyl; said alkylsulfinyl group may be selected from the group consisting of methanesulfinyl, ethanesulfinyl, and isopropanesulfinyl; said alkylsulfonyl group may be selected from the group consisting of methanesulfonyl, ethanesulfonyl, and isopropanesulfonyl; said alkylamino group may be selected from the group consisting of methylamino, dimethylamino, ethylamino, and diethylamino; said carboxylate group may be selected from the group consisting of ethyl carboxylate, methyl carboxylate, n-propyl carboxylate, isopropyl carboxylate, n-butyl carboxylate, sec.-butyl carboxylate, and n-hexyl carboxylate; said carboxamide group may be selected from the group consisting of primary carboxamide, N-methyl carboxamide, N,N-dimethyl carboxamide, N-ethyl carboxamide, and N,N-diethyl carboxamide.

In one embodiment of the invention, $R_1$ and $R_2$ are selected from the group consisting of a hydrogen atom, a hydroxy group, an alkyl group, a halogen atom, an alkoxy group, an alkylthio group, an alkylsulfinyl group, an alkylsulfonyl group, an amino group, and an alkylamino group.

In another embodiment of the invention, $R_1$ and $R_2$ are selected from the group consisting of a hydrogen atom, a hydroxy group, a $C_1$-$C_7$ alkyl group, a halogen atom, a $C_1$-$C_7$ alkoxy group, a $C_1$-$C_7$ alkylthio group, a $C_1$-$C_7$ alkylsulfinyl group, a $C_1$-$C_7$ alkylsulfonyl group, an amino group, and a $C_1$-$C_7$ alkylamino group. Then, said $C_1$-$C_7$ alkyl group may be methyl, ethyl, or benzyl; said halogen atom may be fluorine or iodine: said $C_1$-$C_7$ alkoxy group may be methoxy or ethoxy; said $C_1$-$C_7$ alkylthio group may be methylthio, ethylthio or phenylthio; said $C_1$-$C_7$ alkylsulfinyl group may be ethanesulfinyl; said $C_1$-$C_7$ alkylsulfonyl group may be ethanesulfonyl; said $C_1$-$C_7$ alkylamino group may be ethylamino or diethylamino; and X may represent an ethylcarboxylate or a carboxamide group.

In another embodiment of the invention, $R_1$ and $R_2$ are selected from the group consisting of a hydrogen atom, a $C_2$-$C_7$ alkyl group, a halogen atom, a $C_1$-$C_7$ alkoxy group, a $C_1$-$C_7$ alkylthio group, a $C_1$-$C_7$ alkylsulfinyl group, a $C_1$-$C_7$ alkylsulfonyl group, an amino group, and a $C_1$-$C_7$ alkylamino group; and X represents a carboxylate. Then, said $C_2$-$C_7$ alkyl group may be ethyl, or benzyl; said halogen atom may be fluorine or iodine: said $C_1$-$C_7$ alkoxy group may be methoxy or ethoxy; said $C_1$-$C_7$ alkylthio group may be methylthio, ethylthio or phenylthio; said $C_1$-$C_7$ alkylsulfinyl group may be ethanesulfinyl; said $C_1$-$C_7$ alkylsulfonyl group may be ethanesulfonyl; said $C_1$-$C_7$ alkylamino group may be ethylamino or diethylamino; and X represents a an ethylcarboxylate.

In the compound according to formula (I) of the present invention, $R_1$ and $R_2$ may be the same or different. When they are different, the compounds of formula (I) are capable of existing in stereoisomeric forms. It will be understood that the invention encompasses all optical isomers of the compounds of formula (I) and mixtures thereof including racemates.

Therefore, the present invention includes, where $R_1$ is different from $R_2$, compounds of formula (I) that are racemic or enantiomerically pure, either as the (S) or (R) enantiomer. Therefore, the present invention includes, where $R_1$ is different from $R_2$, compounds of formula (I) that are racemic or enantiomeric pure, either as the (S) or (R) stereoisomer.

Within the scope of the invention are enantiomers of the compounds of the formula (I), as hereinbefore defined. Moreover, the enantiomers of the DHA derivatives according to the invention might be in the form of a carboxylic acid, or a pharmaceutically acceptable salt thereof, any ester, anhydride or amide (primary, secondary, tertiary). The acid derivative might be in the form of a phospholipid or a tri- di- or monoglyceride.

In one embodiment of a compound of formula (I) according to the invention, one of $R_1$ and $R_2$ represents a $C_2$-$C_7$ alkyl group, e.g. ethyl or benzyl, and the other one represents a hydrogen atom. Preferably, the alkylgroup is ethyl.

In another embodiment of a compound of formula (I) according to the invention, one of $R_1$ and $R_2$ represents an alkoxy group, e.g. ethoxy or methoxy, and the other one represents a hydrogen atom.

In another embodiment of a compound of formula (I) according to the invention, one of $R_1$ and $R_2$ represents a halogen atom, e.g. fluorine or iodine, and the other one represents a hydrogen atom.

In another embodiment of a compound of formula (I) according to the invention, one of $R_1$ and $R_2$ represents an allylthio group, e.g. ethylthio, methylthio or phenylthio, and the other one represents a hydrogen atom. Preferably, the alkylthiogroup is ethylthio.

In another embodiment of a compound of formula (I) according to the invention, one of $R_1$ and $R_2$ represents an alkylsulfonyl group, e.g. ethylsulfonyl, and the other one represents a hydrogen atom.

In another embodiment of a compound of formula (I) according to the invention, one of $R_1$ and $R_2$ represents an amino group, and the other one represents a hydrogen atom.

In another embodiment of a compound of formula (I) according to the invention, one of $R_1$ and $R_2$ represents an alkyl-amino group, e.g. ethyl-amino or diethyl-amino, and the other one represents a hydrogen atom.

In a further embodiment of a compound of formula (I) according to the invention, $R_1$ and $R_2$ are the same and represent $C_1$-$C_7$-alkyl groups, preferably methyl groups or ethyl groups.

In preferred embodiments of the compound of formula (I), X is a carboxylate, e.g. ethyl carboxylate.

The compound according to the invention may exist in the form of a phospholipid, a tri-, di- or monoglyceride, or in the form of a free acid.

The alpha-substituted DHA-derivatives according to the invention have very surprisingly shown excellent results with regard to pharmaceutical activity. In particular, the fatty acid derivatives according to the present invention possess a huge potential to be used in the treatment and/or prevention of diabetes and pre-stages thereof.

Another aspect of the present invention relates to a compound of formula (I) for use as a medicament.

The invention also relates to a process for the manufacture of a compound of formula (I). For example, a compound of formula (I) may be prepared from (all-Z)-4,7,10,13,16,19-docosahexaenoic acid (DHA). The DHA may e.g. originate from a vegetable, a microbial and/or an animal source, such as a marine fish oil. Another important advantage with compounds of formula (I) is that the fatty acid analogues can be prepared directly from (all-Z)-4,7,10,13,16,19-docosahexaenoic acid (DHA).

In a preferred embodiment of the invention, the fatty acid analogues of formula (I) are prepared from DHA, wherein said DHA is obtained from at least one of vegetable, microbial and animal origins, or combinations thereof. The invention includes therefore derivatives prepared from DHA-containing oil from microbial origin. Suitable, said DHA is produced from a marine oil, such as a fish oil.

Another aspect of the present invention relates to a pharmaceutical composition comprising a compound of formula (I) as an active ingredient. The pharmaceutical composition may further comprise a pharmaceutically acceptable carrier. Suitably, a pharmaceutical composition according to the invention is formulated for oral administration, e.g. in the form of a capsule or a sachet. A suitable daily dosage of a compound of formula (I) according to the present invention is 10 mg to 10 g, in particular 100 mg to 1 g of said compound.

In addition, the present invention relates to a fatty acid composition comprising a compound of formula (I). At least 60%, or at least 90% by weight of the fatty acid composition may be comprised of said compound. The fatty acid composition may further comprise (all-Z)-5,8,11,14,17-eicosapentaenoic acid (EPA), (all-Z)-4,7,10,13,16,19-docosahexaenoic acid (DHA), (all-Z)-6,9,12,15,18-heneicosapentaenoic acid (HPA), and/or (all-Z)-7,10,13,16,19-docosapentaenoic acid (DPA). The fatty acids may be present in the form of derivatives. A fatty acid composition according to the present invention may further comprise a pharmaceutically acceptable antioxidant, e.g. tocopherol. Within the scope of the present invention is also a fatty acid composition described above, for use as a medicament.

In a further aspect, the present invention relates to the use of a compound according to formula (I) for the manufacture of a medicament for controlling body weight reduction and/or for preventing body weight gain; for the manufacture of a medicament for the treatment and/or the prevention of obesity or an overweight condition; for the manufacture of a medicament for the prevention and/or treatment of diabetes in an animal, in particular type 2 diabetes; for the manufacture of a medicament for the treatment and/or prevention of amyloidos-related diseases; for the manufacture of a medicament for the treatment or prophylaxis of multiple risk factors for cardiovascular diseases, preferably for the treatment of elevated blood lipids for the manufacture of a medicament for prevention of stroke, cerebral or transient ischaemic attacks related to atherosclerosis of several arteries.

In addition, the present invention relates to a method for controlling body weight reduction and/or for preventing body weight gain; a method for the treatment and/or the prevention of obesity or an overweight condition; a method for the prevention and/or treatment of diabetes, in particular type 2 diabetes; a method for the treatment and/or prevention of amyloidos-related diseases; a method for the treatment or prophylaxis of multiple risk factors for cardiovascular diseases; a method for the prevention of stroke, cerebral or transient ischaemic attacks related to atherosclerosis of several arteries, wherein a pharmaceutically effective amount of a compound of formula (I) is administered to a human or an animal. Suitably, the compound of formula (I) is administered orally to a human or an animal.

DETAILED DESCRIPTION OF THE INVENTION

In the research work leading to the present invention, novel DHA-derivatives were prepared, which showed excellent pharmaceutical activity.

Figure 1:
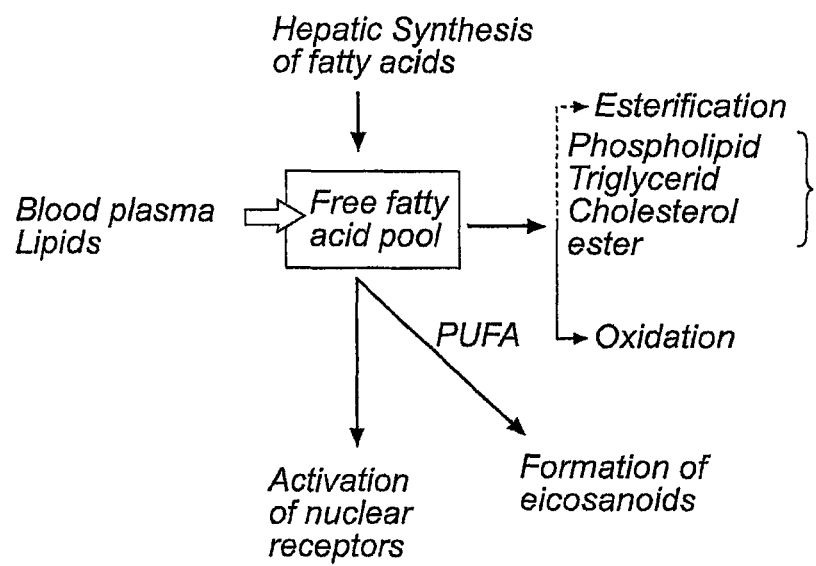
FIG. 1 is a schematic overview of the free fatty acid pool theory.

Fatty acids enter cells passively or trough G-protein coupled transporter systems, such as fatty acid transport proteins. Well inside the cells they are temporarily bound by binding proteins (Fatty acid binding proteins, FABP), which play an important role in directing fatty acids to various intracellular compartments for metabolism and gene expression (Pawar & Jump 2003). (FIG. 1 liver cell).

Esterification of fatty acids into triglycerides, polar lipids, and cholesterol esters and their beta-oxidation (mitochondrial and peroxisomal) requires conversion of fatty acids to acyl CoA thioesters. Other pathways, like microsomal NADPH-dependent mono oxidation and eicosanoids synthesis, utilise non-esterified fatty acids as substrates. All these reactions are likely to influence cellular levels of free fatty acids (non-esterified) and thereby the amount and type of fatty acids which could be used as ligands to nuclear receptors. Because PPARs are known to bind non-esterified fatty acids it is reasonable to expect that the composition of the free fatty acid pool is an important determinant in the control of PPAR activity.

The composition of the free fatty acid pool is affected by the concentration of exogenous fatty acids entering the cells, and their rate of removal via pathways listed above. Since short and medium chain fatty acids are effectively recruited to these pathways, in practice only the long-chain polyunsaturated fatty acids will be available for liganding to nuclear receptors. In addition, fatty acid structure may also be an important determinant. Even if a series of mono and polyunsaturated fatty acids demonstrated affinity to the PPARα receptor, EPA and DHA demonstrated the highest binding capacity in experiments with rat liver cells (Pawar & Jump 2003).

Searching for fatty acid candidates available for genetic modification of proteins by interaction with nuclear receptors like the PPARs, it is important to verify that the respective fatty acids will be enriched in the free fatty acid pool.

DHA which enter cells are rapidly converted to fatty acyl-CoA thioesters and incorporated into phospholipids and due to this, the intracellular DHA level is relatively low. These DHA-CoA are also substrate for β-oxidation primarily in the peroxisomes that lead to retroconvertion of DHA to EPA, see FIG. 1. Because of the rapid incorporation into neutral lipids and the oxidation pathway DHA will not stay long in the free fatty acid pool. Due to this the effect of DHA on gene expression is probably limited.

The present invention aims at achieving an accumulation of fatty acid derivatives in the free fatty acid pool, rather than incorporation into phospholipids. The present inventors have surprisingly found that the introduction of at least one substituent in the α-position of DHA will lead to a slower oxidation rate in addition to less incorporation into neutral lipids. This will lead to an increased effect on gene expression, since the DHA derivatives will accumulate in the tissue particular within liver, muscle, and adipose cells and trigger local nuclear receptor activity to a greater extent than DHA.

The different substituents according to the invention will give variable affinities of the derivatives to fatty acids binding receptors. It is also possible that changes in affinity to fatty acids binding proteins lead to changes in the biological activity of these α-substituted DHA derivatives of formula (I). Altogether theses changes lead to an increased therapeutic effect of the DHA derivatives according to the invention compared to DHA.

EPA (all-Z)-5,8,11,14,17-eicosapentaenoic acid) has earlier been alkylated in α- and β-position to inhibit mitochondrial β-oxidation. DHA is not oxidised in the mitochondria, but rather incorporated into phospholipids. In the peroxisomes though some DHA is retroconverted to EPA. A substituent in the α-position of EPA and DHA will due to this affect different metabolic pathways. It has earlier been shown that α-methyl EPA and β-methyl EPA is incorporated into phospholipids and triglycerides while α-ethyl EPA is not (Larsen 1998). In this study the derivatives were tested as substrates and/or inhibitors of enzymes involved in the eicosanoid cascade. Since most of the substrates for these enzymes are fatty acids liberated from phospholipids it was desired that the derivatives were incorporated into phospholipids. In contrast to this, as mentioned before, we want derivatives that will not incorporate into lipids, but rather accumulate in the NEFA pool.

Throughout this description, the abbreviation "PRB-x", where x is an integer, will be used when describing specific compounds according to the invention. Below, the structural formulas and trivial names for each of these compounds are listed:

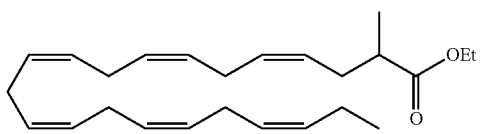

PRB-1 α-methyl docosahexaenoic acid ethyl ester

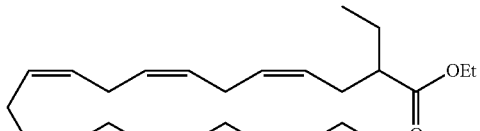

PRB-2 α-ethyl docosahexaenoic acid ethyl ester

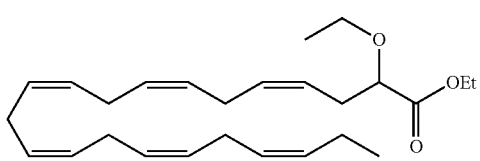

PRB-3 α-ethoxy docosahexaenoic acid ethyl ester

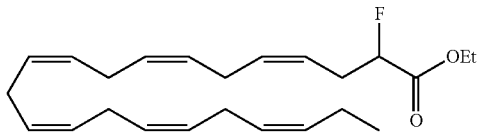

PRB-4 α-fluoro dzocosahexaenoic acid ethyl ester

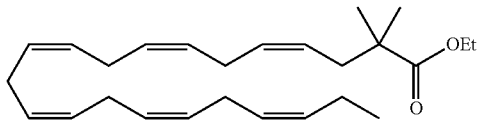

PRB-5 α,α di-methyl docosahexaenoic acid ethyl ester

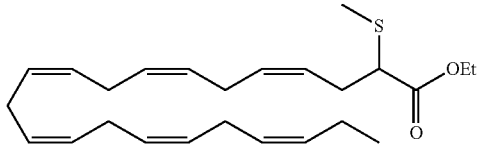

PRB-6 α-tiomethyl docosahexaenoic acid ethyl ester

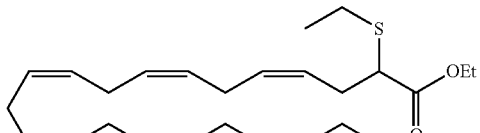

PRB-7 α-tioethyl docosahexaenoic acid ethyl ester

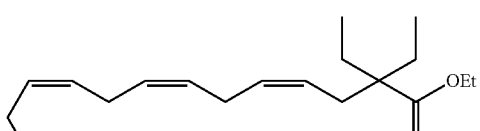

PRB-8 α,α di-ethyl docosahexaenoic acid ethyl ester

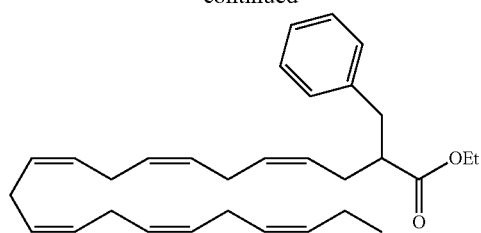

PRB-9 α-benzyl docosahexaenoic acid ethyl ester

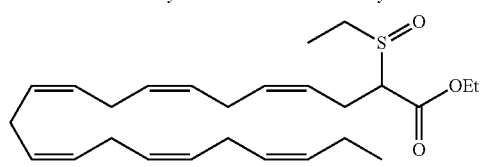

PRB-10 α-ethanesulfinyl docosahexaenoic acid ethyl ester

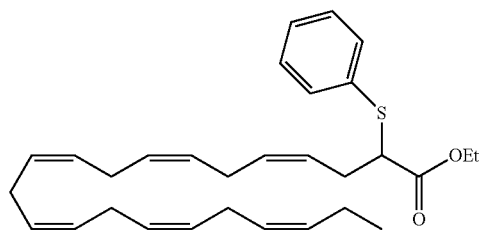

PRB-11 α-tiophenyl docosahexaenoic acid ethyl ester

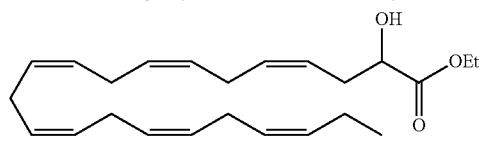

PRB-12 α-hydroxy docosahexaenoic acid ethyl ester

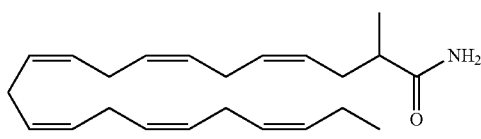

PRB-13 α-methyl docosahexaenoic acid amide

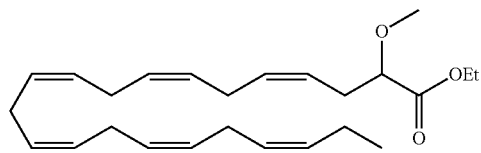

PRB-14 α-methoxy docosahexaenoic acid ethyl ester

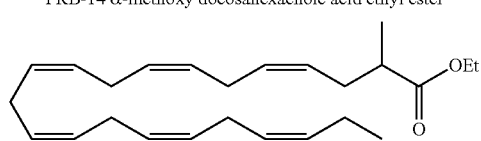

PRB-15 α-iodo docosahexaenoic acid ethyl ester

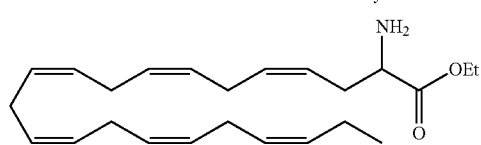

PRB-17 α-amino docosahexaenoic acid ethyl ester

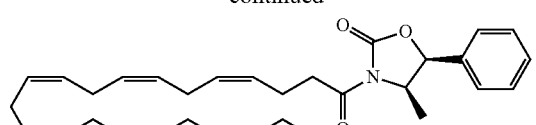

PRB-18 (4R,5S)-3-docosahexaenoyl-
4-methyl-5-phenyl-oxazolidin-2-one

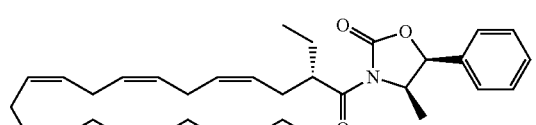

PRB-19 (4R,5S)-3-[(S)-α-ethyldocosahexaenoyl]-
4-methyl-5-phenyl-oxazolidin-2-one

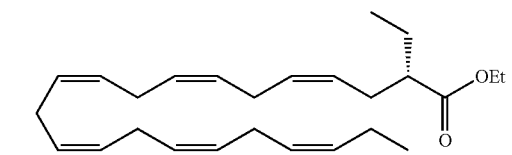

PRB-20 (S)-(+)-α-ethyl docosahexaenoic acid ethyl ester

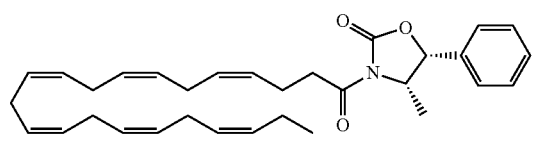

PRB-21 (4S,5R)-3-docosahexaenoyl-
4-methyl-5-phenyl-oxazolidin-2-one

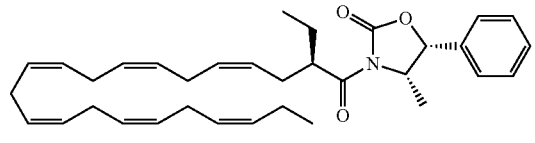

PRB-22 (4S,5R)-3-[(R)-α-ethyldocosahexaenoyl]-
4-methyl-5-phenyl-oxazolidin-2-one

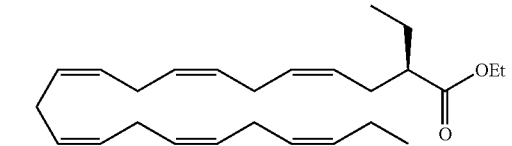

PRB-23 (R)-(-)-α-ethyl docosahexanoic acid ethyl ester

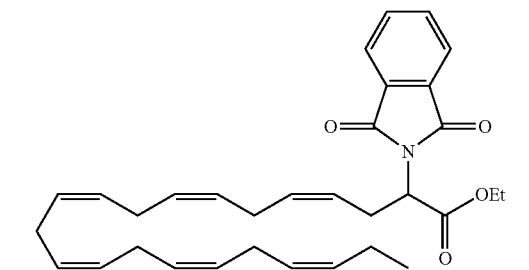

PRB-24
2-(1,3-Dioxo-1,3-dihydro-isoindol-2-yl)-
docosahexaenoic acid ethyl ester

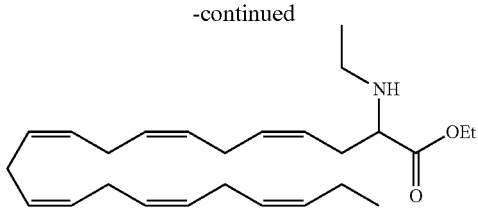

PRB-25 α-ethyl-amino
docosahexanoic acid ethyl ester

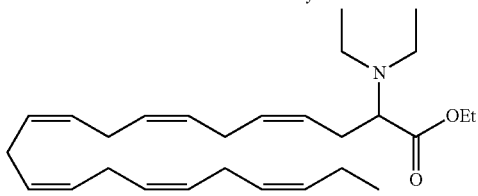

PRB-26 α-diethyl-amino
docosahexanoic acid ethyl ester

PRB-1 corresponds to a compound of formula (I) in which $R_1$ or $R_2$ is methyl, and the other one is hydrogen, and X is ethyl carboxylate.

PRB-2 corresponds to a compound of formula (I) in which $R_1$ or $R_2$ is ethyl, and the other one is hydrogen, and X is ethyl carboxylate.

PRB-3 corresponds to a compound of formula (I) in which $R_1$ or $R_2$ is ethoxy, and the other one is hydrogen, and X is ethyl carboxylate.

PRB-4 corresponds to a compound of formula (I) in which $R_1$ or $R_2$ is fluorine, and the other one is hydrogen, and X is ethyl carboxylate.

PRB-5 corresponds to a compound of formula (I) in which $R_1$ and $R_2$ is methyl, and X is ethyl carboxylate.

PRB-6 corresponds to a compound of formula (I) in which $R_1$ or $R_2$ is methylthio, and X is ethyl carboxylate.

PRB-7 corresponds to a compound of formula (I) in which $R_1$ or $R_2$ is ethylthio, and the other one is hydrogen, and X is ethyl carboxylate.

PRB-8 corresponds to a compound of formula (I) in which $R_1$ and $R_2$ is ethyl, and the other one is hydrogen, and X is ethyl carboxylate.

PRB-9 corresponds to a compound of formula (I) in which $R_1$ or $R_2$ is benzyl, and the other one is hydrogen, and X is ethyl carboxylate.

PRB-10 corresponds to a compound of formula (I) in which $R_1$ or $R_2$ is ethanesulfinyl, and the other one is hydrogen, and X is ethyl carboxylate.

PRB-11 corresponds to a compound of formula (I) in which $R_1$ or $R_2$ is phenylthio, and the other one is hydrogen, and X is ethyl carboxylate.

PRB-12 corresponds to a compound of formula (I) in which $R_1$ or $R_2$ is hydroxy, and the other one is hydrogen, and X is ethyl carboxylate.

PRB-13 corresponds to a compound of formula (I) in which $R_1$ or $R_2$ is methyl, and the other one is hydrogen, and X is primary carboxamide.

PRB-14 corresponds to a compound of formula (I) in which $R_1$ or $R_2$ is methoxy, and the other one is hydrogen, and X is ethyl carboxylate.

PRB-15 corresponds to a compound of formula (I) in which $R_1$ or $R_2$ is iodine, and the other one is hydrogen, and X is ethyl carboxylate.

PRB-17 corresponds to a compound of formula (I) in which $R_1$ or $R_2$ is amino, and the other one is hydrogen, and X is ethyl carboxylate.

PRB-20 corresponds to the (S) stereoisomer of a compound of formula (I) in which $R_1$ or $R_2$ is ethyl, and the other one is hydrogen, and X is ethyl carboxylate.

PRB-23 corresponds to the (R) stereoisomer of a compound of formula (I) in which $R_1$ or $R_2$ is ethyl, and the other one is hydrogen, and X is ethyl carboxylate.

PRB-24 corresponds to a compound of formula (I) in which $R_1$ or $R_2$ is N-phthalimide, and the other one is hydrogen, and X is ethyl carboxylate.

PRB-25 corresponds to a compound of formula (I) in which $R_1$ or $R_2$ is ethyl-amino, and the other one is hydrogen, and X is primary carboxamide.

PRB-26 corresponds to a compound of formula (I) in which $R_1$ or $R_2$ is diethyl-amino, and the other one is hydrogen, and X is ethyl carboxylate.

PRB-2 is the most preferred compound according to the present invention. Other preferred compounds according to the invention are PRB-5, PRB-7, and PRB-8.

It is to be understood that the present invention encompasses any possible pharmaceutically acceptable salts, solvates, complexes or prodrugs of the compounds of formula (I).

"Prodrugs" are entities which may or may not possess pharmacological activity as such, but may be administered (such as orally or parenterally) and thereafter subjected to bioactivation (for example metabolized) in the body to form the agent of the present invention which is pharmacologically active.

Where X is a carboxylic acid, the present invention also includes salts of the carboxylic acids. Suitable pharmaceutically acceptable salts of carboxy groups includes metal salts, such as for example aluminium, alkali metal salts such as lithium, sodium or potassium, alkaline metal salts such as calcium or magnesium and ammonium or substituted ammonium salts.

A "therapeutically effective amount" refers to the amount of the therapeutic agent which is effective to achieve its intended purpose. While individual patient needs may vary, determination of optimal ranges for effective amounts of each nitric oxide adduct is within the skill of the art. Generally the dosage regimen for treating a condition with the compounds and/or compositions of this invention is selected in accordance with a variety of factors, including the type, age, weight, sex, diet and medical condition of the patient.

By "a medicament" is meant a compound according to formula (I), in any form suitable to be used for a medical purpose, e.g. in the form of a medicinal product, a pharmaceutical preparation or product, a dietary product, a food stuff or a food supplement.

In the context of the present specification, the term "therapy" also includes "prophylaxis" unless there are specific indications to the contrary. The terms "therapeutic" and "therapeutically" should be constructed accordingly.

Treatment includes any therapeutic application that can benefit a human or non-human animal. The treatment of mammals is particularly preferred. Both human veterinary treatments are within the scope of the present invention. Treatment may be in respect of an existing condition or it may be prophylactic. It may be of an adult, a juvenile, an infant, a fetus, or a part of any of the aforesaid (e.g. an organ, tissue, cell, or nucleic acid molecule). By "chronic treatment" is meant treatment that continues for some weeks or years.

"A therapeutically or a pharmaceutically active amount" relates to an amount that will lead to the desired pharmacological and/or therapeutic effects. A compound according to the present invention may for example be included in a food stuff, a food supplement, a nutritional supplement, or a dietary product Alpha-substituted DHA derivatives and EPA (or DHA for that matter) can be bound together and combined on triglyceride form by an esterification process between a mixture of alpha-derivatives, EPA and glycerol catalysed by Novozyme 435 (a commercially available lipase from *Candida antarctica* on immobilised form).

The compounds of formula (I) have activity as pharmaceuticals, in particular as triggers of nuclear receptor activity. Thus, the present invention also relates to compounds of formula (I), pharmaceutically acceptable salts, solvates, complexes nr pro-drugs thereof, as hereinbefore defined, for use as a medicament and/or for use in therapy. Preferably, the novel compounds, or pharmaceutically acceptable salts, solvates, complexes or pro-drugs thereof, of the invention may be used:

- for the prevention and/or treatment of diabetes mellitus in humans or animals;
- for controlling body weight reduction and/or for preventing body weight gain;
- for the prevention and/or treatment of obesity or an overweight condition in humans or in an animal;
- for the treatment and/or prevention of amyloidos-related diseases;
- for the treatment or prophylaxis of multiple risk factors for cardiovascular diseases;
- for the prevention of stroke, cerebral or transient ischaemic attacks related to atherosclerosis of several arteries.
- for the treatment of TBC or HIV.

There are two major forms of diabetes mellitus. One is type 1 diabetes, which is known as insulin-dependent diabetes mellitus (IDDM), and the other one is type 2 diabetes, which is also known as non-insulin-dependent diabetes mellitus (NIDDM). Type 2 diabetes is related to obesity/overweight and lack of exercise, often of gradual onset, usually in adults, and caused by reduced insulin sensitivity, so called peripheral insulin resistance. This leads to a compensatory increase in insulin production. This stage before developing full fetched type 2 diabetes is called the metabolic syndrome and characterized by hyperinsulinemia, insulin resistance, obesity, glucose intolerance, hypertension, abnormal blood lipids, hypercoagulopathia, dyslipidemia and inflammation, often leading to atherosclerosis of the arteries. Later when insulin production seizes, type 2 diabetes mellitus develops.

In a preferred embodiment, the compounds according to formula (I) may used for the treatment of type 2 diabetes. The compounds according to formula (I) may also be used for the treatment of other types of diabetes selected from the group consisting of metabolic syndrome, secondary diabetes, such as pancreatic, extrapancreatic/endocrine or drug-induced diabetes, or exceptional forms of diabetes, such as lipoatrophic, myotonic or a disease caused by disturbance of the insulin receptors. The invention also includes treatment of type 2 diabetes. Suitably, compounds of formula (I), as hereinbefore defined, may activate nuclear receptors, preferably PPAR (peroxisome proliferator-activated receptor) $\alpha$ and/or $\gamma$.

The compounds of formula (I) may also be used for the treatment and/or prevention of obesity. Obesity is usually linked to an increased insulin resistance and obese people run a high risk of developing type 2 diabetes which is a major risk factor for development of cardiovascular diseases. Obesity is a chronic disease that afflict an increasing proportion of the population in Western societies and is associated, not only with a social stigma, but also with decreasing life span and numerous problems, for instance diabetes mellitus, insulin resistance and hypertension. The present invention thus fulfils a long felt need for a drug that will reduce total body weight, or the amount of adipose tissue, of preferably obese humans, towards their ideal body weight without significant adverse side effects.

The compounds according to formula (I) may also be used for the prevention and/or treatment of amyloidos-related diseases. Amyloidos-related conditions or diseases associated with deposition of amyloid, preferably as a consequence of fibril or plaque formation, includes Alzheimer's disease or dementia, Parkinson's disease, amyotropic lateral sclerosis, the spongiform encephalopathies, such as Creutzfeld-jacob disease, cystic fibrosis, primary or secondary renal amyloidoses, IgA nephropathy, and amyloid deposition in arteries, myocardium and neutral tissue. These diseases can be sporadic, inherited or even related to infections such as TBC or HIV, and are often manifested only late in life even if inherited forms may appear much earlier. Each disease is associated with a particular protein or aggregates of these proteins are thought to be the direct origin of the pathological conditions associated with the disease. The treatment of a amyloidos-related disease can be made either acutely or chronically.

The compounds of formula (I) may also be used for the treatment due to reduction of amyloid aggregates, prevention of misfolding of proteins that may lead to formation of so called fibrils or plaque, treatment due to decreasing of the production of precursor protein such as A$\beta$-protein (amyloid beta protein), and prevention and/or treatment due to inhibiting or slow down the formation of protein fibrils, aggregates, or plaque. Prevention of fibril accumulation, or formation, by administering compounds of formula (I), as hereinbefore defined, is also included herein. In one embodiment, the novel compounds, pharmaceutically acceptable salts, solvates, complexes or pro-drugs thereof, as hereinbefore defined, are used for the treatment of TBC (tuberculosis) or HIV (human immunodeficiency virus).

Further, the compounds of formula (I) may be administered to patients with symptoms of atherosclerosis of arteries supplying the brain, for instance a stroke or transient ischaemic attack, in order to reduce the risk of a further, possible fatal, attack.

The compounds of formula (I) may also be used for the treatment of elevated blood lipids in humans.

Additionally, the compounds of formula (I), as hereinbefore defined, are valuable for the treatment and prophylaxis of multiple risk factors known for cardiovascular diseases, such as hypertension, hypertriglyceridemia and high coagulation factor VII phospholipid complex activity: Preferably, the compounds of formula (I) is used for the treatment of elevated blood lipids in humans.

The compounds of formula (I) and pharmaceutically acceptable salts, solvates, pro-drugs or complexes thereof may be used on their own but will generally be administered in the form of a pharmaceutical composition in which the compounds of formula (I) (the active ingredient) are in association with a pharmaceutically acceptable adjuvant, diluent or carrier.

The present invention thus also provides a pharmaceutical composition comprising a therapeutically effective amount of the compound of formula (I) of the present invention and a pharmaceutically acceptable carrier, diluent or excipients (including combinations thereof).

This is a composition that comprises or consists of a therapeutically effective amount of a pharmaceutically active agent. It preferably includes a pharmaceutically acceptable carrier, diluent or excipients (including combinations thereof). Acceptable carriers or diluents for therapeutic use are well known in the pharmaceutical art. The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Pharmaceutical compositions within the scope of the present invention may include one or more of the following: preserving agents, solubilising agents, stabilising agents, s wetting agents, emulsifiers, sweeteners, colourants, flavouring agents, odorants, salts compounds of the present invention may themselves be provided in the form of a pharmaceutically acceptable salt), buffers, coating agents, antioxidants, suspending agents, adjuvants, excipients and diluents.

A pharmaceutical composition according to the invention is preferably formulated for oral administration to a human or an animal. The pharmaceutical composition may also be formulated for administration through any other route where the active ingredients may be efficiently absorbed and utilized, e.g. intravenously, subcutaneously, intramuscularly, intranasally, rectally, vaginally or topically.

In a specific embodiment of the invention, the pharmaceutical composition is shaped in form of a capsule, which could also be microcapsules generating a powder or a sachet. The capsule may be flavoured. This embodiment also includes a capsule wherein both the capsule and the encapsulated fatty acid composition according to the invention is flavoured. By flavouring the capsule it becomes more attractive to the user. For the above-mentioned therapeutic uses the dosage administered will, of course, vary with the compound employed, the mode of administration, the treatment desired and the disorder indicated.

The pharmaceutical composition may be formulated to provide a daily dosage of 10 mg to 10 g. Preferably, the pharmaceutical composition is formulated to provide a daily dosage between 50 mg and 5 g of said composition. Most preferably, the pharmaceutical composition is formulated to provide a daily dosage between 100 mg and 1 g of said composition. By a daily dosage is meant the dosage per 24 hours. The dosage administered will, of course, vary with the compound employed, the mode of administration, the treatment desired and the disorder indicated. Typically, a physician will determine the actual dosage which will be most suitable for an individual subject. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The agent and/or the pharmaceutical composition of the present invention may be administered in accordance with a regimen of from 1 to 10 times per day, such as once or twice per day. For oral and parenteral administration to human patients, the daily dosage level of the agent may be in single or divided doses.

A further aspect of the present invention relates to a fatty acid composition comprising compounds of formula (I). A fatty acid composition comprising compounds of formula (I) increases the natural biological effects of DHA that are a result of regulation of gene expression, and the derivatives according to the present invention will accumulate in the free fatty acid pool.

The fatty acid composition may comprise in the range of 60 to 100% by weight of the compounds of formula (I), all percentages by weight being based on the total weight of the fatty acid composition. In a preferred embodiment of the invention, at least 80% by weight of the fatty acid composition is comprised of compounds of formula (I). More preferably, the compounds of formula (I) constitute at least 90% by weight of the fatty acid composition. Most preferably, the compounds of formula (I) constitutes more than 95% by weight of the fatty acid composition.

The fatty acid composition may further comprise at least one of the fatty acids (all-Z)-5,8,11,14,17-eicosapentaenoic acid (EPA), (all-Z)-4,7,10,13,16,19-docosahexaenoic acid (DHA), (all-Z)-6,9,12,15,18-heneicosapentaenoic acid (HPA), and (all-Z)-7,10,13,16,19-docosapentaenoic acid (DPAn-3), (all-Z)-8,11,14,17-eicosatetraenoic acid (ETAn-3), or combinations thereof. Further, the fatty acid composition may comprise (all-Z)-4,7,10,13,16-Docosapentaenoic acid (DPAn-6) and/or (all-Z)-5,8,11,14-eicosatetraenoic acid (ARA), or derivatives thereof. The fatty acid composition may also comprise at least these fatty acids, or combinations thereof, in the form of derivatives. The derivatives are suitably substituted in the same way as the DHA derivatives of formula (I), as hereinbefore defined.

The fatty acid composition according to the invention may comprise (all-Z omega-3)-6,9,12,15,18-heneicosapentaenoic acid (HPA), or derivatives thereof, in an amount of at least 1% by weight, or in an amount of 1 to 4% by weight.

Further, the fatty acid composition according to the invention may comprise omega-3 fatty acids other than EPA and DHA that have 20, 21, or 22 carbon atoms, or derivatives thereof, in an amount of at least 1.5% by weight, or in an amount of at least 3% by weight.

In specific embodiments of the invention, the fatty acid composition is a pharmaceutical composition, a nutritional composition or a dietary composition. The fatty acid composition may further comprise an effective amount of a pharmaceutically acceptable antioxidant. Preferably, the antioxidant is tocopherol or a mixture of tocopherols. In a preferred embodiment the fatty acid composition further comprises tocopherol, or a mixture of tocopherols, in an amount of up to 4 mg per g of the total weight of the fatty acid composition. Preferably, the fatty acid composition comprises an amount of 0.2 to 0.4 mg per g of tocopherols, based on the total weight of the composition.

Another aspect of the invention provides a fatty acid composition, or any pharmaceutically acceptable salt, solvate, pro-drug or complex thereof, comprising compounds of formula (I), as hereinbefore defined, for use as a medicament and/or in therapy. Such a fatty acid composition may be used to prevent and/or treat the same conditions as outlined for the compounds of formula (I) above.

When the fatty acid composition is used as a medicament, it will be administered in a therapeutically or a pharmaceutically active amount.

In a preferred embodiment, the fatty acid composition is administered orally to a human or an animal.

The present invention also provides the use of a compound of formula (I), or a pharmaceutically acceptable salt, solvate, pro-drug or complex thereof, as hereinbefore defined, for the manufacture of a medicament for controlling body weight reduction and/or for preventing body weight gain; for the manufacture of a medicament for the treatment and/or the prevention of obesity or an overweight condition; for the manufacture of a medicament for the prevention and/or treatment of diabetes in a human or animal; for the manufacture of a medicament for the treatment and/or prevention of amyloidos-related diseases; for the manufacture of a medicament for the treatment and prophylaxis of multiple risk factors known for cardiovascular diseases, such as hypertension, hypertriglyceridemia and high coagulation factor VII phospholipid complex activity; for the manufacture of a medicament for the treatment of TBC or HIV; for the manufacture of a medicament for prevention of stroke, cerebral or transient ischaemic attacks related to atherosclerosis of several arteries; for the manufacturing of a medicament for lowering triglycerides in the blood of mammals and/or evaluating the HDL cholesterol levels in the serum of a human patients; or for the manufacturing of a medicament for the treatment and/or prevention of the multi metabolic syndrome termed "metabolic syndrome". All these embodiments also include the use of a fatty acid composition, as hereinbefore defined, comprising compounds of formula (I) for the manufacture of medicaments as outlined above. The present invention further relates to the use of alpha-hydroxy-DHA for the manufacture of medicaments as outlined above.

The present invention also relates to a method for controlling body weight reduction and for preventing body weight gain, wherein a fatty acid composition comprising at least a compound of formula (I), as hereinbefore defined, is administered to a human or an animal.

Further, the invention relates to a method for the treatment and/or the prevention of obesity or an overweight condition, wherein a fatty acid composition comprising at least a compound of formula (I), as hereinbefore defined, is administered to a human or an animal.

In a preferred embodiment of the invention, the present invention relates to a method for the prevention and/or treatment of diabetes mellitus, wherein a fatty acid composition comprising at least a compound of formula (I), as hereinbefore defined, is administered to a human or an animal. Preferably, diabetes mellitus is a type 2 diabetes.

Other aspects of the present invention relate to;
a method for the treatment and/or prevention of amyloidos-related diseases;
a method for the treatment or prophylaxis of multiple risk factors for cardiovascular diseases;
a method for prevention of stroke, cerebral or transient ischaemic attacks related to atherosclerosis of several arteries;
wherein a fatty acid composition comprising at least a compound of formula (I), as hereinbefore defined, is administered to a human or an animal.

The fatty acid derivatives of formula (I) may be prepared most effectively from DHA. If the start material is not pure DHA (i.e. not 100% DHA) the final fatty acid composition will contain a mixture of DMA derivatives, as hereinbefore defined, and an amount of other fatty acids than DHA, wherein these fatty acids are substituted in the same way as the novel fatty acid analogous of formula (I). Such embodiments are also included herein.

In another embodiment of the invention, the compounds of formula (I) are prepared from (all-Z)-4,7,10,13,16,19-docosahexaenoic acid (DHA), wherein said DHA is obtained from a vegetable, a microbial and/or an animal source, or combinations thereof. Preferably, said DHA is obtained from a marine oil, such as a fish oil.

The fatty acids in the composition may also be obtained from a vegetable; a microbial or an animal source, or combinations thereof. Thus, the invention also includes a fatty acid composition prepared from a microbial oil.

The present invention provides processes for preparing novel fatty acid analogous of formula (I), as hereinbefore defined.

DHA is produced from biological sources like marine, microbial or vegetable fats. All possible raw materials are mixtures of fatty acids on triglyceride form where DHA constitutes only a fraction of the fatty acids. Typical DHA concentrations are 40% in microbial fats and 10-25% in marine fats. DHA-containing vegetable fats are during development and fats with high DHA concentrations are expected in the future.

The first process step will always be conversion of the triglycerides to free fatty acids or monoesters. Preferable esters are methyl or ethyl esters, but other esters are possible. In this way the fatty acids bound together three by three on triglycerides are separated from each other and thereby making separation possible. Several methods of separating DHA from other fatty acids are available, the most common ones being short path distillation separating the fatty acids by volatility, and urea precipitation separating the fatty acids by degree of unsaturation. Other methods reported are silver nitrate complexation also separating the fatty acids on degree on unsaturation, esterification reactions catalysed by fatty acid selective lipases in combination with short path distillation and countercurrent extraction with supercritical carbon dioxide.

The most important challenges connected to production of pure DHA is to separate it from the other C20-22 highly unsaturated fatty acids present in all available sources. These fatty acids have properties so similar to DHA that none of the methods mentioned above provide sufficient degree of separation. For some microbial high DHA fats, which have very low levels of C20-22 highly unsaturated fatty acids, short path distillation alone or in combination of other methods mentioned may provide more that 90% purity.

Most DHA containing fats also contain considerable amounts of C20-22 highly unsaturated fatty acids, e.g. EPA (20:5n-3), n-3DPA (22:5n-3), HPA (21:5n-3) and others. The only available method for separating DHA from such fatty acids is preparative High Performance Liquid Chromatography, the stationary phase being silica gel or silver nitrate impregnated silica gel, the mobile phase being selected organic solvents or supercritical carbon dioxide. With this method DHA with more than 97% purity is available. However, it has to be noted that the production costs increases strongly with concentration, as an example is production cost for 97% DHA more 5 times higher than for 90% DHA.

DHA having a purity of 90, 95 eller 97% contains small amounts of other fatty acids. As an example, DHA having a purity of 97% contains n-3DPA (22:5n-3), but also long chain fatty acids, e.g. EPA (20:5n-3), HPA (21:5n-3), and others. However, the other fatty acids will react in a way similar to DHA and provide alpha-substituted derivatives.

Organic synthesis may provide a purification method since DHA and n-6DPA (and 22:5n-6 which normally is present in very low concentrations) are the only known fatty acids that can provide gamma-lactones by cyclisation with the first double bond. Lactonisation followed by purification and hydrolysis back to DHA may be a possibility, but it is expected that this pathway is even more expensive than HPLC.

In one embodiment, the compounds of formula (I) where $R_1$ (or $R_2$) is a hydrogen are prepared through the following processes (Scheme 1). Suitably adapted, these processes can also be used for preparing compounds represented by the general formula (I) where both $R_1$ and $R_2$ are e.g. a $C_1$-$C_7$ alkyl group, a benzyl, a halogen, a benzyl, an alkenyl, or an alkynyl.

Compounds represented by the general formula (I) where $R_1$ is a hydrogen and $R_2$ denotes a $C_1$-$C_7$ alkyl group, a benzyl, a halogen, a benzyl, an alkenyl, an alkynyl are prepared by reacting a DHA ester with a strong non-nucleophilic base like lithium diisopropylamine or potassium/sodium hexamethyldisilazideane in a solvent such as tetrahydrofuran, diethylether at temperatures of −60 to −78° C., to provide the ester enolate (process 1).

product might possess interesting biologically activity. Thus, in one embodiment of the invention the condensation (intermediate) product mentioned above, as well as the use of this product for treatment and/or prevention of diseases according to the present invention, are disclosed.

In a further embodiment, compounds represented by the general formula (I) are synthesised through following processes (Scheme 2).

(Scheme 1)

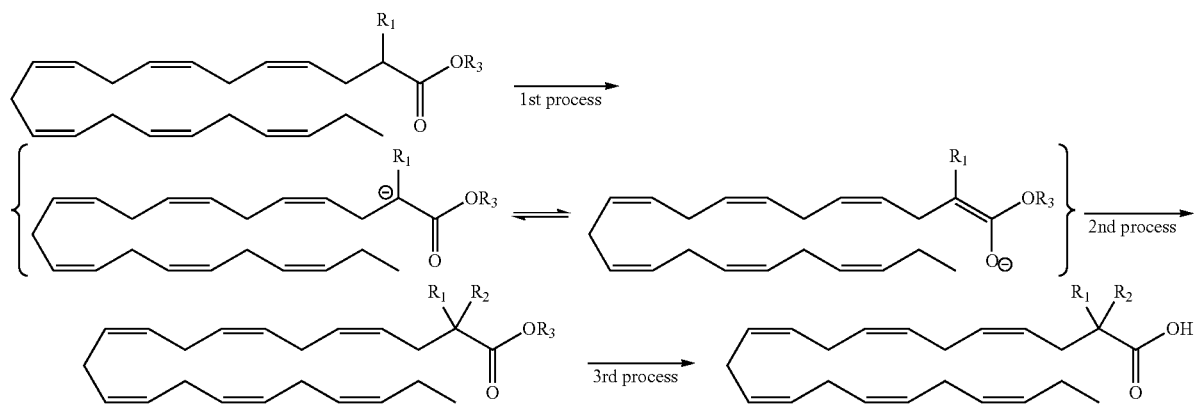

This ester enolate is reacted with an electrophilic reagent like an alkylhalide exemplified by ethyliodide, benzylchloride, an acyl halide exemplified by acetyl chloride, benzoyl bromide, a carboxylic anhydride exemplified by acetic anhydride or a electrophilic halogenation reagent exemplified by (Scheme 2)

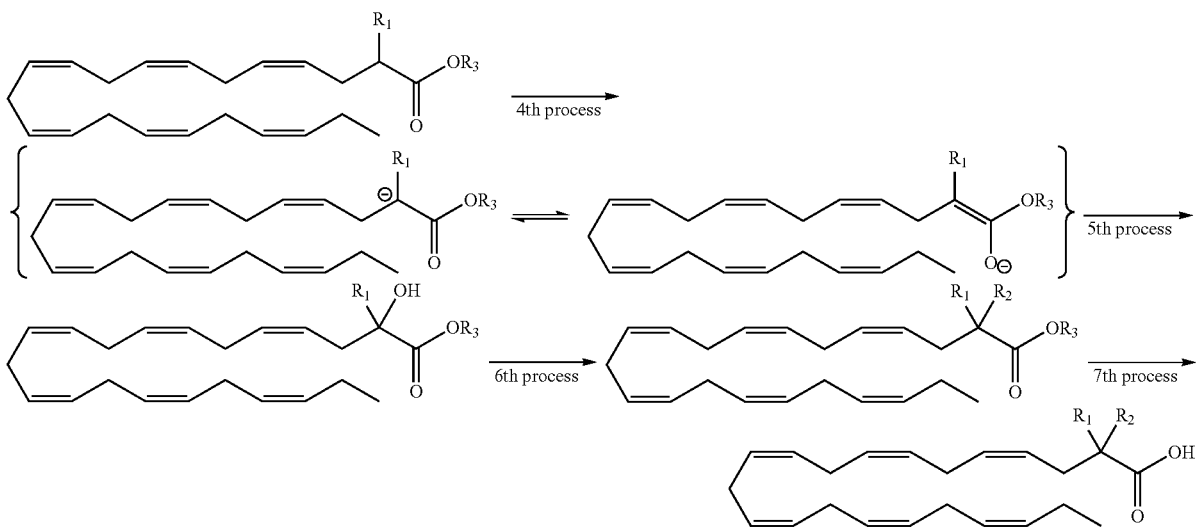

N-fluorobenzene sulfonimide (NFSI), etc. to provide the monosubstituted derivative (process 2). The ester is further hydrolysed in a solvent like ethanol or methanol to the carboxylic acid derivative by addition of a base like lithium/sodium hydroxide in water at temperatures between 15-40° C.

Claisen condensation of the DHA EE occurs during the treatment of DHA EE with a strong base. This condensation Compounds represented by the general formula (I) where $R_1$ is a hydrogen and $R_2$ denotes a hydroxy, an alkoxy group, an acyloxy are prepared by reacting a DHA ester with a strong non-nucleophilic base like lithium diisopropylamine or potassium/sodium hexamethyldisilazideane in a solvent such as tetrahydrofuran, diethylether at temperatures of −60 to −78° C., to provide the ester enolate (process 4). This ester enolate is reacted with an oxygen source like dimethyldioxirane, 2-(phenylsulfonyl)-3-phenyloxaziridine, molecular oxygen with different additives like trimethylphosphite or different catalysts like a Ni(II) complex to provide alpha-hydroxy DHA ester (process 5). Reaction of the secondary alcohol with a base like sodiumhydride in a solvent like THF or DMF generates an alkoxide that is reacted with different electrophilic reagents as allyliodide for example; methyl iodide, ethyl iodide, benzylbromide or an acyl halide, for example; acetyl chloride, benzoyl bromide (process 6). The ester is hydrolysed in a solvent like ethanol or methanol to the carboxylic acid derivative by addition of a base like lithium/sodium hydroxide in water at temperatures between 15-40° C. (process 7).

The hydroxy-DHA ester is a useful intermediate for the introduction of other functional groups in the α-position according to the invention. The hydroxyl function can be activated by conversion to a halide or tosylate prior to reaction with different nucleophiles like ammonia, amines, thiols, etc. The Mitsunobu reaction is also useful for the conversion of a hydroxyl group into other functional groups. (Mitsunobu, O, Synthesis, 1981, 1).

Compounds represented by the general formula (I), as hereinbefore defined, can also be synthesised by combinations of the different processes previously described. The present invention includes the processes mentioned above.

The invention further provides a process for the preparation of a pharmaceutical composition of the invention, with comprises mixing of at least a compound of formula (I), or a pharmaceutically acceptable salt, solvate, complex or prodrug thereof, as hereinbefore defined, with a pharmaceutically acceptable adjuvant, diluent or a carrier.

The enantiomeric pure compounds can be prepared by resolving a racemic compound of formula (I), as hereinbefore defined. The resolution of a compound of formula (I) may be carried out using known resolution procedures, for example by reacting the compound of formula (I) with an enantiomerically pure auxiliary to provide a mixture of diastereomers that can be separated by chromatography. Thereafter the two enantiomers of compound (I) may be regenerated from the separated diastereomers by conventional means, such as hydrolysis.

There is also a possibility to use stoichiometric chiral auxiliaries to effect an asymmetricintroduction of the substituents, as hereinbefore defined, in the α-position of DHA. The use of chiral oxazolidin-2-ones has proved to be a particularly effective methodology. The enolates derived from chiral N-acyloxazolidines can be quenched with a variety of electrophiles in a highly stereo regulated manner (Ager, Prakash, Schaad 1996).

EXAMPLES

The invention will now be described in more detail by the following examples, which are not to be constructed as limiting the invention. In the examples the structures were verified by Mass Spectrometry (MS). It should be pointed out that the fatty acid derivatives may also be produced from low and medium DHA-containing starting material (i.e. about 40-60 w % DHA).

Synthesis Protocols

Preparation of α-methyl DHA EE (PRB-1)

Butyllithium (228 ml, 0.37 mol, 1.6 M in hexane) was added dropwise to a stirred solution of diisopropylamine (59.5 ml, 0.42 mol) in dry THF (800 ml) under $N_2$ at 0° C. The resulting solution was stirred at 0° C. for 30 min., cooled to −78° C. and stirred an additional 30 min. before dropwise addition of DHA EE (100 g, 0.28 mol) in dry THF (500 ml) during 2 h. The dark-green solution was stirred at −78° C. for 30 min. before MeI (28 ml, 0.45 mol) was added. The solution was allowed to reach −20° C. during 1.5 h, then poured into water (1.5 l) and extracted with heptane (2×800 ml). The combined organic phases were washed with 1 M HCl (1 l), dried ($Na_2SO_4$), filtered and evaporated in vacuo. The product was purified by dry flash chromatography on silica gel eluting with heptane/EtOAc (99:1) to give 50 g (48%) of the titled compound as a slightly yellow oil;

$^1$H-NMR (200 MHz, $CDCl_3$) δ 1.02 (t, J=7.5 Hz, 3H), 1.20 (d, J 6.8 Hz, 3H), 1.29 (t, J 7.1 Hz, 3H), 2.0-2.6 (m, 5H), 2.8-3.0 (m, 10H), 4.17 (t, J 7.1 Hz, 2H), 5.3-5.5 (m, 12H);

MS (electrospray); 393 [M+Na].

Preparation of α-ethyl DHA EE (PRB-2)

Butyllithium (440 ml, 0.67 mol, 1.6 M in hexane) was added dropwise to a stirred solution of diisopropylamine (111 ml, 0.78 mol) in dry THF (750 ml) under $N_2$ at 0° C. The resulting solution was stirred at −78° C. for 45 min. before dropwise addition of DHA EE (200 g, 0.56 mol) in dry THF (1.6 l). The addition of the ester was complete in 4 hours. The dark-green solution was stirred at −78° C. for 30 min. before EtI (65 ml, 0.81 mol) was added. The solution was allowed to reach −40° C. before an additional amount of EtI (5 ml, 0.06 mol) was added, and finally reach −15° C. (during 3 hours from −78° C.) before the mixture was poured into water and extracted with hexane (2×). The combined organic phases were washed with 1 M HCl, water, dried ($Na_2SO_4$), filtered and evaporated in vacuo. The product was purified by flash chromatography on silica gel eluting with heptane/EtOAc (99:1 followed by 50:1) to give 42.2 g (20%) of the titled compound as a yellow oil;

$^1$H-NMR (200 MHz; $CDCl_3$) δ 0.8-1.0 (m, 6H), 1.2-1.4 (m, 4H), 1.5-1.7 (m, 2H), 2.12 (m, 2H), 2.3-2.5 (m, 2H), 2.8-3.0 (m, 10H), 4.18 (t, J 7.1 Hz, 2H), 5.3-5.6 (m, 12H);

MS (electrospray); 407 [M+Na].

Preparation of α-ethoxy-DHA ethylester (PRB-3)

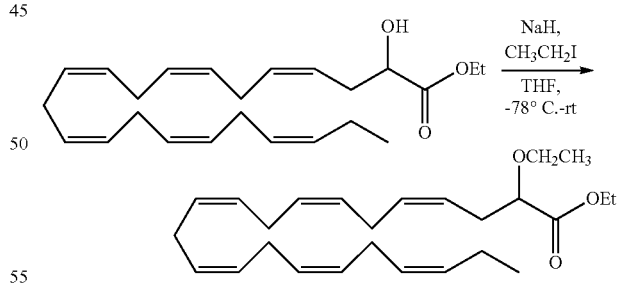

To a suspension of 60% NaH (84.1 mg, 2.1 mmol) in THF, 5 mL, at −78° C. under $N_2$-atmosphere was added drop wise a solution of α-hydroxy-DHA ethyl ester (PRB-12) (372 mg, 1.00 mmol) in THF, 5 mL, the resulting mixture was stirred at −78° C. for 20 minutes before ethyl iodide (0.24 mL, 3.01 mmol) was added drop wise. The reaction mixture was gradually warmed to room temperature over night. Saturated aqueous $NH_4Cl$, 15 mL, was added and the mixture was extracted with diethyl ether, 25 mL×2, the organic phase was washed with brine, 25 mL, dried ($Na_2SO_4$) filtered, evaporated in vacuo and subjected to flash chromatography on silica gel eluting with heptane/EtOAc (95:5) to yield-68 mg (17%) of the product as a yellow liquid.

$^1$H NMR (200 MHz, CDCl$_3$) δ 0.94 (t, J=7.5 Hz, 3H), 1.16-1.29 (m, 6H), 2.05 (quint, J=7.2 Hz, 2H), 2.50 (m, 2H), 2.76-2.84 (m, 10H), 3.33-3.48 (m, 1H), 3.53-3.71 (m, 1H), 3.83 (dd, J=6.8 Hz, J=6.2 Hz, 1H), 4.18 (q, J=7.1 Hz, 2H), 5.31-5.45 (m, 12H)

$^{13}$C NMR (50 MHz, CDCl$_3$) δ 14.2, 15.1, 20.5, 25.5, 25.6, 25.7, 31.0, 60.8, 66.0, 78.7, 124.1, 127.0, 127.8, 127.9, 128.0 (2 signals), 128.2 (2 signals), 128.5, 130.7, 132.0, 172.5 (3 signals hidden)

MS (electrospray); 423 [M+Na]$^+$

Preparation of α-fluoro DHA EE (PRB-4)

LDA (2.1 ml, 4.2 mol, 2 M in THF/heptane/ethylbenzene) in dry THF (10 ml) under N$_2$ at −78° C. was dropwise added DHA EE (1 g, 2.8 mmol) in dry THF (30 ml) during 15 min. NFSi (1.06 g, 3.4 mmol) was then added. The solution was allowed to reach RT and stirred for 70 hours. The mixture was poured into water and extracted with hexane (2×). The combined organic phases were washed with 1 M HCl, water, dried (Na$_2$SO$_4$), filtered and evaporated in vacuo; MS (electrospray); 397 [M+Na].

Preparation of α,α-dimethyl DHA EE (FRB-5)

Butyllithium (100 ml, 0.17 mol, 1.6 M in hexane) was added dropwise to a stirred solution of diisopropylamine (28 ml, 0.20 mol) in dry THF (100 ml) under N$_2$ at 0° C. The resulting solution was stirred at 0° C. for 30 min., cooled to −78° C. and dropwise added a solution of DHA EE (50 g, 0.14 mol) in dry THF (200 ml). The resulting dark-green solution was stirred at −78° C. for 30 min. before MeI (17 ml, 0.28 mol) was added. The solution was allowed to reach −10° C., then poured into water and extracted with hexane (2×). The combined organic phases were washed with 1 M HCl, dried (Na$_2$SO$_4$), filtered and evaporated in vacuo.

The procedure was repeated, but the crude product of α-methyl DHA EE was used instead of DHA EE. The product was purified by dry flash chromatography on silica gel eluting with heptane/EtOAc (99:1 followed by 98:2) to give 31.6 g (59%) of the titled compound as a slightly yellow oil;

$^1$H-NMR (200 MHz; CDCl$_3$) δ 1.01 (t, J 7.5 Hz, 3H), 1.21 (s, 6H); 1.28 (t, J 7.1 Hz, 3H), 2.08 (m, 2H), 2.34 (d, J 6.8 Hz, 2H), 2.8-3.0 (m, 10H), 4.15 (q, J 7.5 Hz, 2H), 5.3-5.6 (m, 12H);

$^{13}$C-NMR (50 MHz; CDCl$_3$) δ 14.7, 21.0, 25.3, 26.0, 26.1, 38.3, 42.8, 60.7, 125.8, 127.4, 128.3, 128.5, 128.6, 128.7, 129.0, 130.7, 132.4, 177.9;

MS (electrospray); 385 [M+H].

Preparation of α-thiomethyl DHA (PRB-6)

α-Iodo DHA EE (0.5 g, 1.04 mmol) dissolved in 20 mL THF at 0° C. under N$_2$. MeSNa (80 mg, 1.14 mmol) was added the reaction and the mixture was allowed to stir for a few minutes before it was diluted with heptane. The organic phase was washed with water (2×) dried (Na$_2$SO$_4$) and evaporated in vacuo. The desired product was isolated by flash chromatography Heptan/EtOAc (30:1) to give α-thiomethyl DHA EE as a pale yellow oil. The α-thiomethyl DHA EE was dissolved in 10 mL EtOH and 10 mL THF. The solution was added LiOH (0.39 g, 9.2 mmol) dissolved in 5 mL water. The reaction mixture was allowed to stir overnight at RT, before diluting with water and heptane. The organic fraction was extracted with 1M LiOH (2x) and the combined aqueous phases was acidified with 5M HCl and extracted with diethyl ether (2x). The combined organic phases was washed with brine, water, dried (Na$_2$SO$_4$) and evaporated in vacuo to give 183 mg (47%) of the title compound as a pale yellow oil;

$^1$H-NMR (200 MHz, CDCl$_3$) δ 0.98 (t, J 6.6 Hz, 3H), 1.95-2.65 (m, 7H), 2.72-3.05 (m, 10H), 3.12-3.43 (m, 1H), 5.20-5.70 (m, 12H), 10.65 (br s, 1H);

$^{13}$H-NMR (50 MHz, CDCl$_3$) δ 14.7, 21.0, 25.9, 26.0, 26.2, 28.8, 125.4, 127.4, 128.1, 128.3, 128.4, 128.7, 128.9, 129.0, 131.6, 132.4, 177.0.

Preparation of α-thioethyl DHA EE (PRB-7)

α-Iodo DHA EE (11 g, 23 mmol) dissolved in 100 mL THF under N$_2$ at 0° C. EtSNa (2.1 g, 25 mmol) was added the solution and was allowed to stir for 1 hour at 0° C. The reaction was quenched with 1M HCl and diluted with Heptan. The organic phase was washed with water (2x), dried (Na$_2$SO$_4$) and evaporated in vacuo. The desired product was isolated by flash chromatography Heptan/EtOAc (30:1) to give 7.3 g (76%) of the title compound as a pale yellow oil;

$^1$H-NMR (200 MHz, CDCl$_3$) δ 1.1-1.3 (m, 9H), 2.05 (m, 2H), 2.3-2.7 (m, 4H), 2.7-2.9 (m, 10H), 3.25 (m, 1H), 4.17 (q, J=7.1 Hz, 2H), 5.3-5.5 (m, 12H);

MS (electrospray): 439 [M+Na].

Preparation of α,α-diethyl DHA EE (PRB-8)

Butyllithium (38.6 ml, 0.62 mol, 1.6 M in hexane) was added dropwise to a stirred solution of diisopropylamine (9.1 ml, 0.65 mol) in dry THF (200 ml) under N$_2$ at 0° C. The resulting solution was stirred at 0° C. for 30 min., cooled to −78° C. and dropwise added a solution of DHA EE (20.0 g, 0.56 mol) in dry THF (100 ml). The resulting dark-green solution was stirred at −78° C. for 30 min., before EtI (6.8 ml, 0.84 mol) was added. The solution was allowed to reach −10° C., then poured into water and extracted with hexane (2×). The combined organic phases were washed with 1 M HCl, dried (Na$_2$SO$_4$), filtered and evaporated in vacuo.

The procedure was repeated, but the crude product of α-ethyl DHA EE was used instead of DHA EE. The reaction mixture after addition of EtI was allowed to reach ambient temperature and was stirred over night. The product was purified by dry flash chromatography on silica gel eluting with heptane/EtOAc (99:1 followed by 98:2) to give 10.0 g (43%) of the titled compound as a slightly yellow oil;

$^1$H-NMR (200 MHz; CDCl$_3$) δ 0.83 (t, J 7.4 Hz, 6H), 0.94 (t, J 5.8 Hz, 3H), 1.28 (t, J 7.1 Hz, 3H), 1.63 (q, J 7.4 Hz, 4H), 2.10 (m, 2H), 2.34 (d, J 6.9 Hz, 2H), 2.8-3.0 (m, 10H), 4.15 (q, J 7.5 Hz, 2H), 5.3-5.6 (m, 12H);

$^{13}$C-NMR (50 MHz; CDCl$_3$) δ 8.9, 14.7, 21.0, 23.1, 25.9, 26.0, 26.2, 27.4, 31.2, 50.1, 60.6, 125.5, 127.4, 128.3, 128.6, 128.9, 130.5, 132.4, 177.1;

MS (electrospray); 413.3 [M+H], 435.3 [M+Na].

Preparation of α-benzyl DHA EE (PRB-9)

To a stirred solution of diisopropyl amine (0.91 mL, 6.46 mmol) in dry THF (20 mL) under inert atmosphere held at 0°

C. was added drop wise n-BuLi (1.6 M in hexanes, 3.86 mL, 6.18 mmol). The mixture was stirred at 0° C. for 30 minutes, given −78° C. and stirred at this temperature for five minutes. DHA EE (2.0 g, 5.62 mmol) in dry THF (10 mL) was added drop wise and the mixture was stirred at −78° C. for 20 minutes, then benzyl bromide (0.80 mL, 6.74 mmol) was added. The resulting solution was allowed to reach 0° C. over three hours, portioned between water (100 mL) and heptane (100 mL). The aqueous layer was extracted with heptane (50 mL) and the combined organic layer was washed with 1M HCl and dried ($Na_2SO_4$). Concentration under reduced pressure and purification by flash chromatography (Heptane:EtOAc 99:1) afforded 1.05 g (42%) of the title compound as a colorless oil;

$^1$H-NMR (200 MHz, $CDCl_3$): δ 0.99 (t, 3H), 1.18 (t, 3H), 2.08-2.16 (m, 2H), 2.35-2.42 (m, 2H), 2.74-2.98 (m, 13H), 4.09 (q, 4H), 5.38-5.50 (m, 10H), 7.19-7.36 (m, 5H);

$^{13}$C-NMR (50 MHz, $CDCl_3$): δ 14.61, 14.71, 20.99, 25.98, 26.07, 30.07, 38.32, 48.02, 60.88, 126.75, 126.83, 127.46, 128.31, 128.45, 128.53, 128.58, 128.86, 128.77, 129.01, 129.35, 130.55, 132.46, 138.89, 175.39.

MS (electrospray): 447.3 [M+H], 469.3 [M+Na].

Preparation of α-ethanesulfinyl DHA EE (PRB-10)

To a solution of α-thioethyl DHA EE (0.5 g, 1.3 mmol) in 15 mL $CHCl_3$ held at −20° C. under inert atmosphere was added a solution of MCPBA (0.22 g, 1.3 mmol) in 10 mL $CHCl_3$. The reaction mixture was stirred for 2 h at this temperature, filtered and washed with a saturated aqueous solution of $NaHCO_3$. The aqueous phase was extracted twice with $CHCl_3$ and the combined organic phase was washed with water and brine, dried with $Na_2SO_4$, filtered and concentrated. The product was isolated from residual material after flash chromatography using hexane:EtOAc 8:2 to afford 0.35 g (70%) of the title compound.

$^1$H NMR (200 MHz, $CDCl_3$): δ 0.99 (t, 3H), 1.27-1.45 (m, 6H), 2.09 (m, 2H), 2.79-2.94 (m, 14H), 3.55 (m, 1H), 4.25 (q, 2H), 5.37-5.59 (m, 12H).

$^{13}$C NMR (50 MHz, $CDCl_3$): δ 7.97, 14.58, 14.68, 20.95, 23.68, 25.17, 25.93, 26.04, 44.20, 45.15, 62.30, 64.08, 123.91, 124.47, 127.41, 127.86, 128.26, 128.40, 128.44, 128.72, 128.72, 128.96, 129.12, 132.42, 132.47, 174.55.

MS (electrospray): 455.3 [M+Na].

Preparation of α-thiophenyl-DHA ethylester (PRB-11)

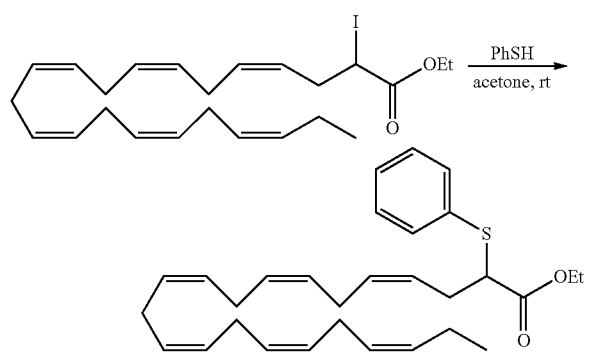

To a solution of α-iodo-DHA ethylester (PRB-15) (3.40 g, 7.05 mmol) in acetone, 20 mL, a solution of sodium phenyl sulfide (1.039 g, 7.86 mmol) in acetone, 110 mL, was added drop wise. The resulting mixture was stirred at ambient temperature for 1½ hrs, evaporated in vacuo and subjected to flash chromatography on silica gel eluting with heptane/EtOAc 200:1-95:5 to yield 2.35 g (72%) of the product as a yellow liquid.

$^1$H NMR (200 MHz, $CDCl_3$) δ 0.97 (t, J=7.5 Hz, 3H), 1.18 (t, J=7.1 Hz, 3H), 2.09 (quint, J=7.1 Hz, 2H), 2.54-2.66 (m, 2H), 2.83-2.86 (m, 10H), 3.67 (dd, J=6.8 Hz, J=8.3 Hz, 1H), 4.12 (q, J=7.1 Hz, 2H), 5.24-5.49 (m, 12H), 7.28-7.33 (m, 3H), 7.46-7.50 (m, 2H)

$^{13}$C NMR (50 MHz, $CDCl_3$) δ 14.0, 14.2, 20.5, 25.5, 25.6, 25.7, 29.4, 50.6, 61.1, 125.1, 127.0, 127.7, 127.9, 128.0, 128.3, 128.42, 128.45, 128.9, 131.2, 132.0, 133.0, 133.2, 174.1 (5 signals hidden)

MS (electrospray); 465 [M+H]$^+$, 487 [M+Na]$^+$

HRMS (EI) calculated for $C_{30}H_{40}O_2S$: 464.2749. found: 464.2741

Preparation of α-hydroxy-DHA ethylester (PRB-12)

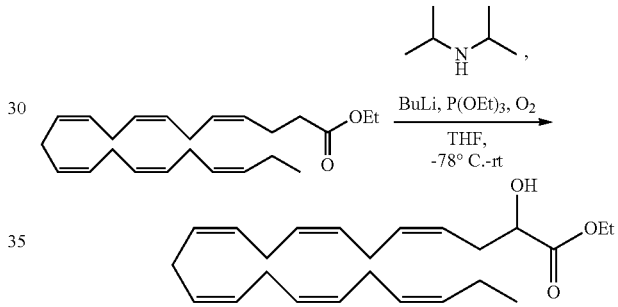

To a solution of diisopropyl amine (19.76 mL, 140 mmol) in dry THF, 40 mL, under $N_2$-atmosphere at −78° C. was added drop wise 1.6 M BuLi in hexane (87.5 mL, 140 mmol). The resulting mixture was stirred at −78° C. for 15 minutes before a solution of DHA ethylester (24.99 g, 70.1 mmol) in THF, 80 mL, was added drop wise. The resulting dark green reaction mixture was stirred for 1 hour at −78° C. before triethylphosphite (12.2 mL, 70.1 mmol) was added drop wise and then $O_2$ was bubbled through the reaction mixture over night while the reaction mixture was kept at −78° C. for 5 hrs and then slowly warmed to room temperature. Saturated aqueous $NaHCO_3$, 100 mL, was added and the mixture was extracted with diethyl ether, 200 mL×2. The organic phase was dried ($Na_2SO_4$), filtered and evaporated in vacuo and subjected to flash chromatography on silica gel eluting with heptane/EtOAc 99:1-95:5 to yield 4.52 g (17%) of the product as a yellow liquid.

$^1$H NMR (200 MHz, $CDCl_3$) δ 0.92 (t, J=7.5 Hz, 3H), 1.24 (t, J=7.1 Hz., 3H), 2.02 (quint, J=7.1 Hz, 2H), 2.44-2.54 (m, 2H), 2.74-2.87 (m, 10H), 4.13-4.24 (m, 3H), 5.25-5.94 (m, 12H)

$^{13}$C NMR (50 MHz, $CDCl_3$) δ 14.0, 14.1, 20.4, 25.4, 25.5, 25.6, 32.0, 61.5, 69.9, 123.3, 126.9, 127.7, 127.9, 128.08, 128.1, 128.2, 128.4, 131.3, 131.8, 174.4 (4 signals hidden)

MS (electrospray); 395 [M+Na]$^+$

HRMS (ES) calculated for $C_{24}H_{36}O_3Na$: 395.2556, found: 395.2543

Preparation of α-methyl-DHA amide (PRE-13)

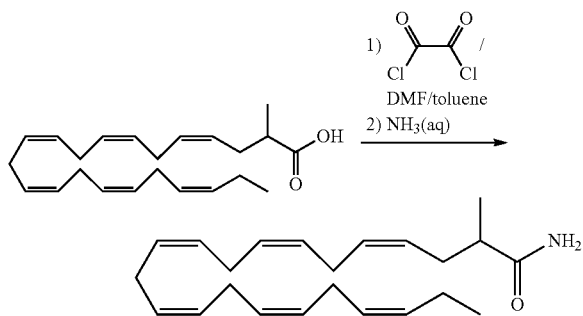

A solution of α-methyl-DHA (PRB-1 FA) (3.13 g, 9.1 mmol) and oxalyl chloride (8.0 mL, 94.5 mmol) in toluene, 90 mL, was added DMF, 0.1 mL, and the resulting mixture was stirred at ambient temperature under $N_2$-atmosphere for 15½ hours. The mixture was then evaporated in vacuo and the residue was dissolved in THF, 100 mL, cooled to 0° C. and aqueous $NH_3$ (20 mL) was added drop wise. The ice-bath was removed and the mixture was stirred at ambient temperature for 4 hours, water, 50 mL, was added and the aqueous phase was extracted with diethyl ether, 2×100 mL. The organic phase was washed with saturated aqueous $NH_4Cl$, 50 mL, dried ($Na_2SO_4$), filtered and evaporated in vacuo and subjected to flash chromatography on silica gel eluting with $CH_2Cl_2$/2M $NH_3$ in MeOH 97.5:2.5 to yield 2.51 g (80%) of the product as a yellow liquid.

$^1$H NMR (200 MHz, $CDCl_3$) δ 0.91 (t, J=7.5 Hz, 3H), 1.10 (d, J=9.8 Hz, 3H), 1.94-2.11 (m, 3H), 2.19-2.35 (m, 2H), 2.76-2.77 (m, 10H), 5.18-5.45 (m, 12H), 6.03 (s, 1H), 6.72 (s, 1H)

$^{13}$C NMR (50 MHz, $CDCl_3$) δ 14.6, 17.6, 20.8, 25:8, 25.9, 32.0, 41.0, 127.3, 128.1, 128.4, 128.6, 128.8, 130.1, 132.2, 179.6 (8 signals hidden)

MS (electrospray); 342 $[M+H]^+$, 364 $[M+Na]^+$

HRMS (EI) calculated for $C_{23}H_{35}NO$: 341.2719, Found: 341.2707

Preparation of α-methoxy-DHA ethylester (PRB-14)

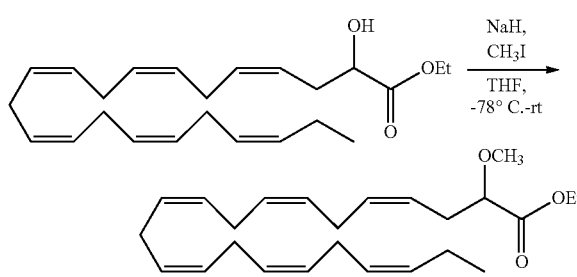

To a suspension of 60% NaH (61.1 mg, 1.53 mmol) in THF, 5 mL, at −78° C. under $N_2$-atmosphere was added drop wise a solution of α-hydroxy-DHA ethyl ester (PRB-12) (373 mg, 1.00 mmol) in THF, 5 mL, the resulting mixture was stirred at −78° C. for 20 minutes before methyl iodide (0.13 mL, 2.09 mmol) was added drop wise. The reaction mixture was gradually warmed to room temperature for 5 hrs. Saturated aqueous $NH_4Cl$, 15 mL, was added and the mixture was extracted with diethyl ether, 25 mL×2, the organic phase was washed with brine, 25 mL, dried ($Na_2SO_4$) filtered, evaporated in vacuo and subjected to flash chromatography on silica gel eluting with heptane/EtOAc 99:1-4:1 to yield 136 mg (35%) of the product as a yellow liquid.

$^1$H NMR (200 MHz, $CDCl_3$) δ 0.92 (t, J=7.5 Hz, 3H), 1.24 (t, J=7.1 Hz, 3H), 2.03 (quint, J=1=7.3 Hz, 2H), 2.48 (t, J=5.7 Hz, 2H), 2.73-2.82 (m, 10H), 3.34 (s, 3H), 3.74 (t, J=6.2 Hz, 1H), 4.17 (q, J=7.1 Hz, 2H), 5.24-5.43 (m, 12H)

$^{13}$C NMR (50 MHz, $CDC_{13}$) δ 14.1, 20.4, 25.4, 25.5, 25.7, 30.6, 57.9, 60.9, 80.8, 123.7, 126.9, 127.71, 127.73, 127.92, 127.94, 128.07, 128.1, 128.2, 128.4, 130.7, 131.8, 171.9 (3 signals hidden)

MS (electrospray); 409 $[M+Na]^+$

HRMS (ES) calculated for $C_{25}H_{38}O_3Na$: 409.2713, Found: 409.2711

Preparation of α-iodo DHA EE (PRB-15)

Diisopropylamine (20 mL, 0.140 mmol) was dissolved in 150 mL THF under $N_2$ at −20° C. n-BuLi (88 mL, 140 mmol, 1.6 M) was added dropwise to the mixture before the solution was cooled to −78° C. DHA EE (50 g, 140 mmol) in 250 mL THF was added dropwise to the solution and the reaction mixture was stirred for 30 min at RT. The resulting mixture was added dropwise to a solution of $I_2$ (42.8 g, 169 mmol) in 400 mL THF under $N_2$ at −78° C. The reaction was quenched with 1M HCl and diluted with Heptan. The organic phase was washed with 10% $Na_2S_2O_3$ (2×), dried ($Na_2SO_4$), filtered and evaporated in vacuo. The desired product was isolated by flash chromatography Heptan/EtOAc (100:1) to give 11.0 g (16%) of the title compound as a pale yellow oil; MS (Electrospray): 505 [M+Na].

Preparation of α-iodo-DHA ethylester (PRB-15)

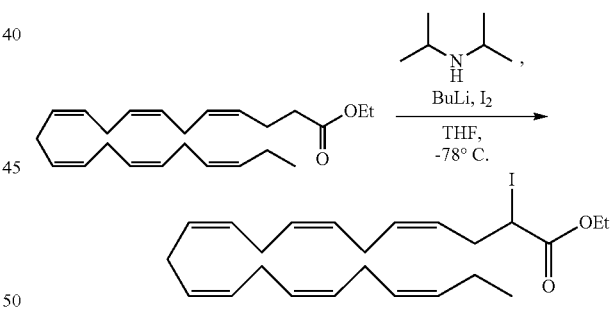

To a solution of diisopropyl amine (42 mL, 298 mmol) in dry THF, 150 mL, under $N_2$-atmosphere at −78° C. was added drop wise 1.6 M BuLi in hexane (158 mL, 253 mmol). The resulting mixture was stirred at −78° C. for 35 minutes before a solution of DHA ethylester (75.05 g, 210 mmol) in THF, 300 mL, was added drop wise. The resulting dark green reaction mixture was stirred for 30 minutes at −78° C. before a solution of $I_2$ (91.06 g, 359 mmol) in THF, 200 mL was added drop wise. The reaction mixture was stirred at −78° C. for 20 minutes before it was quenched with water, 200 mL, and extracted with heptane, 300 mL. The organic phase was washed with 1 M HCl, 150 mL, and water, 200 mL, dried ($Na_2SO_4$), filtered and evaporated in vacuo. The resulting crude product was subjected to flash chromatography on silica gel eluting with heptane/EtOAc (100:1) yielding 26.14 g (26%) of the product as a yellow liquid.

¹H NMR (200 MHz, CDCl₃) δ 0.94 (t, J=7.5 Hz, 3H), 1.24 (t, J=7.1 Hz, 3H), 2.04 (quint, J=7.1 Hz, 2H), 2.69-2.84 (m, 12H), 4.17 (q, J=7.1 Hz, 2H), 4.22 (t, J=7.9 Hz, 1H), 5.24-5.49 (m, 12H)

¹³C NMR (50 MHz, CDCl₃) δ 13.7, 14.2, 25.5, 26.0 (2 signals), 25.8, 34.0, 61.7, 126.1, 127.0, 127.4, 127.8, 127.9, 128.0, 128.2, 128.5, 128.5, 131.6, 131.9, 170.9 (4 signals hidden)

MS (electrospray); 505 [M+Na]⁺

Preparation of α-amino-DHA ethylester (PRB-17)

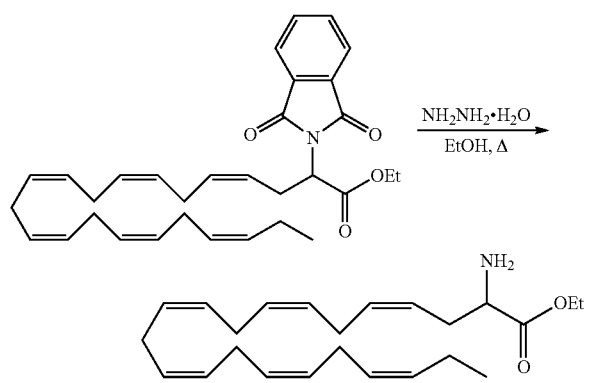

A solution of α-phthalimide-DHA ethylester (313.5 mg, 0.62 mmol) in EtOH, 5 mL, was added hydrazine hydrate (46 µl, 0.95 mmol) and the resulting mixture was refluxed under N₂-atmosphere for 15½ hrs followed by evaporation in vacuo and flash chromatography on silica gel eluting with CH₂Cl₂: 7M NH₃ in MeOH (99:1-95:1) to yield 149 mg (64%) of the product as a yellow liquid.

¹H NMR (200 MHz, CDCl₃) δ 0.91 (t, J=7.5 Hz, 3H), 1.22 (t, J=7.1 Hz, 3H), 1.72 (bs, 2H), 2.02 (quint., J=7.2 Hz, 2H), 2.39-2.46 (m, 2H), 2.73-2.82 (m, 10H), 3.47 (bs, 1H), 4.13 (q, 2H), 5.23-5.56 (m, 12H)

¹³C NMR (50 MHz, CDCl₃) δ 14.1, 20.4, 25.4, 25.5, 25.6, 54.1, 60.8, 124.4, 126.9, 127.7 (2 signals), 127.9, 128.2, 128.3, 128.4, 131.4, 131.9, 189.3 (6 signals hidden)

MS (electrospray); 372 [M+H]⁺

Preparation of (S)-(+)-α-ethyl DHA EE (PRB-20)

Synthesis of intermediate PRB-18

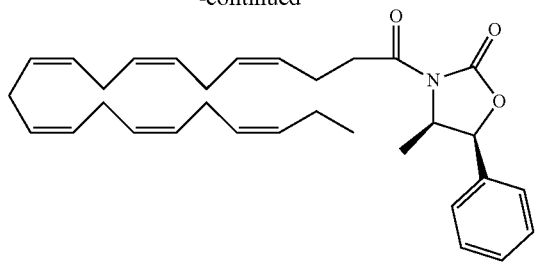

DHA (3.00 g, 18.3 mmol) was dissolved in dry CH₂Cl₂ (120 mL) held at 0° C. under inert atmosphere and added DMAP (2.45 g, 20.1 mmol) and DCC (3.96 g, 19.2 mmol). The mixture was stirred at 0° C. for 20 minutes, added (4R, 5S)-(+)-4-methyl-5-phenyl-2-oxazolidinone (3.24 g, 18.3 mmol) and stirred at ambient temperature for 20 hours. Filtration and purification by flash chromatography (heptane: EtOAc 6:1) afforded 3.00 g (34%) of intermediate PRB-18 as a colorless oil.

¹H-NMR (200 MHz, CDCl₃): δ 0.93-1.05 (t+d, 6H), 2.11 (m, 2H), 2.51 (m, 2H), 2.80-3.00 (m, 10H), 3.05 (m, 2H), 4.77 (m, 1H), 5.34-5.68 (m, 12H), 5.70 (d, 1H), 7.28-7.32 (m, 2H), 7.37-7.47 (m, 3H).

Synthesis of intermediate PRB-19

PRB-18 (1.80 g, 3.70 mmol) in dry THF (10 mL) was added drop wise to a solution of LiHMDS (1M in THF, 4.00 mL, 4.00 mmol) in dry THF(15 mL) held at −78° C. under inert atmosphere. The mixture was stirred at −78° C. for 30 minutes, added EtI (0.89 mL, 11.1 mmol) and slowly given 0° C. over one hour. The mixture was then stirred at 0° C. for 18 hours and portioned between saturated NH₄Cl (50 mL) and diethyl ether (50 mL). The aqueous layer was extracted with diethyl ether (50 mL) and the combined organic layer was washed with 0.1 M HCl (50 mL) and brine (50 mL). Drying (Na₂SO₄) and purification by flash chromatography (heptane: EtOAc 95:5) afforded 0.52 g (27%) of intermediate PRB-19 as a colorless oil.

¹H-NMR (200 MHz, CDCl₃): δ 0.88-1.01 (m, 9H), 1.64-1.78 (m, 2H), 2.08 (m, 2H), 2.31 (m, 1H), 2.48 (m, 1H), 2.87 (m, 10H), 3.87 (m, 1H), 4.75 (m, 1H), 5.32 (m, 12H), 5.63 (d, J 7.1 Hz, 1H), 7.32 (m, 2H), 7.42 (m, 3H).

¹³C-NMR (50 MHz, CDCl₃): δ 7.26, 11.75, 14.67, 14.98, 20.95, 25.57, 25.93, 26.04, 29.93, 44.59, 55.31, 79.10, 125.21, 126.31, 127.17, 127.42, 128.27, 128.50, 128.55, 128.67, 128.95, 129.09, 130.35, 132.42, 133.80, 153.18, 176.25.

MS (electrospray): 538.2 [M+Na]

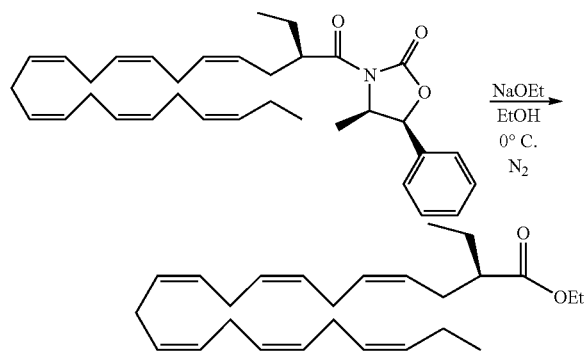

PRB-19 (0.25 g, 0.485 mmol) was dissolved in abs EtOH (5 mL) and given 0° C. under inert atmosphere. NaOEt (1M in EtOH, 0.54 mL, 0.54 mmol) was added and the mixture was stirred at 0° C. for 30 minutes and portioned between water and heptane. The aqueous layer was extracted with heptane and the combined organic layer was washed with 0.1 M HCl and dried. Purification by flash chromatography afforded 0.025 g (13%) of the title compound PRB-20 as a colorless oil.

$^1$H-NMR (200 MHz; CDCl$_3$) δ 0.8-1.0 (m, 6H), 1.2-1.4 (m, 4H), 1.5-1.7 (m, 2H), 2.12 (m, 2H), 2.3-2.5 (m, 2H), 2.8-3.0 (m, 10H), 4.18 (t, 2H), 5.3-5.6 (m, 12H).

MS (electrospray); 407 [M+Na].

[α]$_D$+1.7° (c=1.5, ethanol).

Preparation of (R)-(−)-α-ethyl DHA EE (PRB-23)

Synthesis of intermediate PRB-21

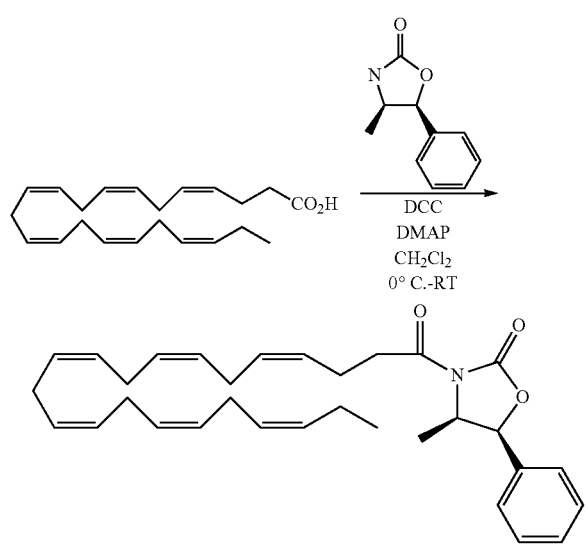

DHA (1.00 g, 3.05 mmol) was dissolved in dry CH$_2$Cl$_2$ (20 mL) held at 0° C. under inert atmosphere and added DMAP (0.41 g, 3.35 mmol) and DCC (0.66 g, 3.20 mmol). The mixture was stirred at 0° C. for 20 minutes, added (4S,5R)-(−)-4-methyl-5-phenyl-2-oxazolidinone (0.54 g, 3.05 mmol) and stirred at ambient temperature for 20 hours. Filtration and purification by flash chromatography (heptane:EtOAc 6:1) afforded 1.08 g (73%) of intermediate PRB-21 as a colorless oil.

$^1$H-NMR (200 MHz, CDCl$_3$): δ 0.93-1.05 (t+d, 6H), 2.11 (m, 2H), 2.51 (m, 2H), 2.80-3.00 (m, 10H), 3.05 (m, 2H), 4.77 (m, 1H), 5.34-5.68 (m, 12H), 5.70 (d, 1H), 7.28. 7.32 (m, 2H), 7.37-7.47 (m, 3H).

Synthesis of intermediate PRB-22

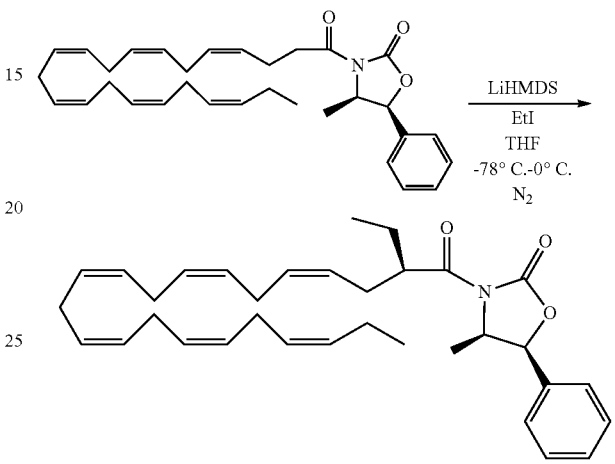

PRB-21 (3.25 g, 6.67 mmol) in dry THF (15 mL) was added drop wise to a solution of LiHMDS (1M in THF, 7.34 mL, 7.34 mmol) in dry THF (35 mL) held at −78° C. under inert atmosphere. The mixture was stirred at −78° C. for 30 minutes, added EtI (1.6 mL, 20.0 mmol) and slowly given 0° C. over one hour. The mixture was then stirred at 0° C. for 18 hours and portioned between saturated NH$_4$Cl (50 mL) and diethyl ether (50 mL). The aqueous layer was extracted with diethyl ether (50 mL) and the combined organic layer was washed with 0.1 M HCl (50 mL) and brine (50 mL). Drying (Na$_2$SO$_4$) and purification by flash chromatography (heptane:EtOAc 95:5) afforded 1.50 g (44%) of intermediate PRB-22 as a colorless oil.

$^1$H-NMR (200 MHz, CDCl$_3$): δ 0.88-1.01 (m, 9H), 1.64-1.78 (m, 2H), 2.08 (m, 2H), 2.31 (m, 1H), 2.48 (m, 1H), 2.87 (m, 10H), 3.87 (m, 1H), 4.75 (m, 1H), 5.32 (m, 12H), 5.63 (d, J 7.1 Hz, 1H), 7.32 (m, 2H), 7.42 (m, 3H).

$^{13}$C-NMR (50 MHz, CDCl$_3$): δ 7.26, 11.75, 14.67, 14.98, 20.95, 25.57, 25.93, 26.04, 29.93, 44.59, 55.31, 79.10, 125.21, 126.01, 127.17, 127.42, 128.27, 128.50, 128.55, 128.67, 128.95, 129.09, 130.35, 132.42, 133.80, 153.18, 176.25.

MS (electrospray): 538.2 [M+Na]

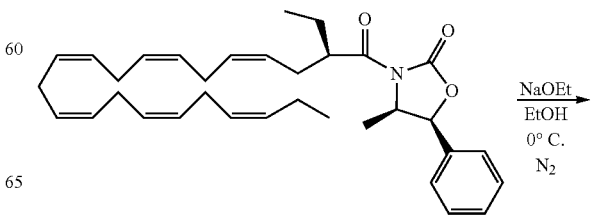

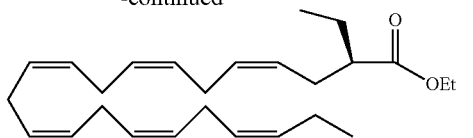

PRB-22 (0.25 g, 0.485 mmol) was dissolved in abs EtOH (5 mL) and given 0° C. under inert atmosphere. NaOEt (1M in EtOH, 0.54 mL, 0.54 mmol) was added and the mixture was stirred at 0° C. for 30 minutes and portioned between water and heptane. The aqueous layer was extracted with heptane and the combined organic layer was washed with 0.1 M HCl and dried. Purification by flash chromatography afforded 0.025 g (13%) of the title compound PRB-23 as a colorless oil.

$^{1}$H-NMR (200 MHz; CDCl$_{3}$) δ 0.8-1.0 (m, 6H), 1.2-1.4 (m, 4H), 1.5-1.7 (m, 2H), 2.12 (m, 2H), 2.3-2.5 (m, 2H), 2.8-3.0 (m, 10H), 4.18 (t, 2H), 5.3-5.6 (m, 12H);

MS (electrospray); 407 [M+Na].

[α]$_{D}$ −1.3° (c=1.00, ethanol).

Preparation of α-phthalimide-DHA ethylester (PRB-24)

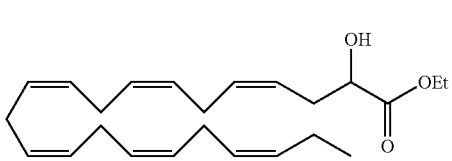

A mixture of the α-hydroxy-DHA ethyl ester (PRB-12) (373.5 mg, 1.00 mmol), phthalimide (178 mg, 1.21 mmol) and triphenyl phosphine (313.9 mg, 1.20 mmol) in THF, 10 mL, was cooled to 0° C. under N$_{2}$-atmosphere before diisopropyl azodicarboxylate (0.24 mL, 1.24 mmol) was added drop wise. The ice-bath was removed and the reaction mixture was stirred at ambient temperature for 18 hrs, whereupon it was evaporated in vacuo and subjected to flash chromatography on silica gel eluting with heptane/EtOAc (99:1-95:1) to yield 323 mg (64%) of the product as a yellow liquid.

$^{1}$H NMR (200 MHz, CDCl$_{3}$) δ 0.95 (t, J=7.5 Hz, 3H), 1.22 (t, J=7.1 Hz, 3H), 2.05 (m, 2H), 2.72-2.84 (m, 1H), 3.02-3.22 (1H), 4.20 (q, J=7.1 Hz, 2H), 4.87 (dd, J=11 Hz, J=4.9 Hz, 1H), 5.17-5.40 (m, 12H), 7.68-7.75 (m, 2H), 7.79-7.85 (m, 2H)

$^{13}$C NMR (50 MHz, CDCl$_{3}$) δ 14.0, 14.1, 20.4, 25.4, 25.4, 25.5, 27.0, 51.8, 61.7, 123.8, 124.3, 126.9, 127.5, 127.7, 127.9, 127.9, 128.1, 128.1, 128.3, 128.4, 131.6, 131.8, 131.8, 134.0, 167.3, 168.7 (2 signals hidden)

MS (electrospray); 502 [M+H]$^{+}$, 524 [M+Na]$^{+}$

Preparation of α-ethylamino-DHA etylester (PRB-25) and α-diethylamino-DHA etylester (PRB-26)

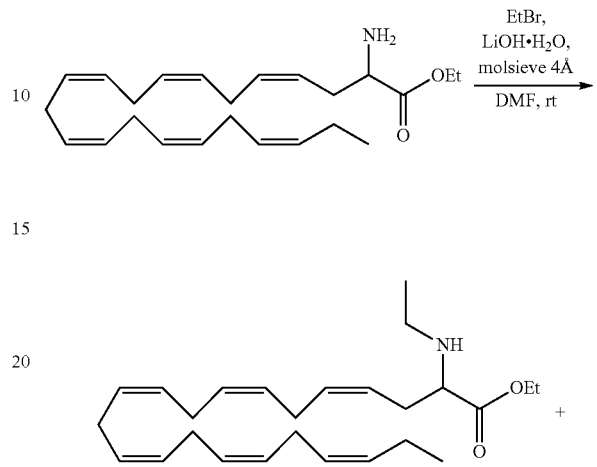

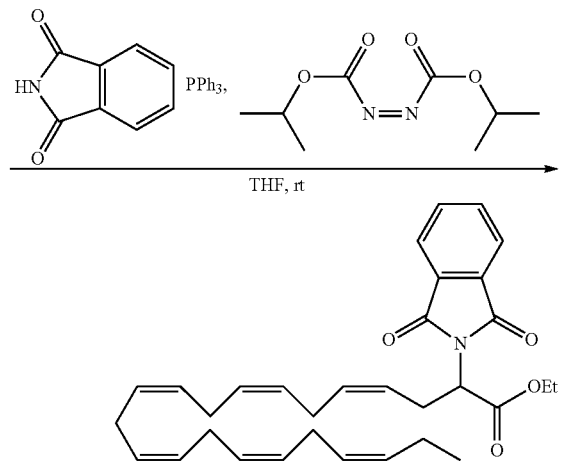

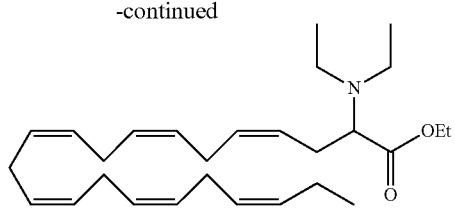

A mixture of the α-amino-DHA ethylester (PRB-17) (746.5 mg, 2.01 mmol), LiOH.H$_{2}$O (171.6 mg, 4.09 mmol) and molsieve 4 Å (599 mg) in DMF, 4 mL, was added ethylbromide (3.0 ml, 40.2 mmol) and the resulting mixture was stirred at ambient temperature for 71 hrs. The mixture was diluted with diethyl ether, 100 mL, and filtered. The organic phase was washed with 1 M NaOH, 20 mL, and brine, 20 mL, dried (Na$_{2}$SO$_{4}$), filtered and evaporated in vacuo and subjected to flash chromatography on silica gel eluting with heptane:EtOAc (95:5)—CH$_{2}$Cl$_{2}$:2M NH$_{3}$ in MeOH (99:1) to yield 458 mg (53%) of PRB-26 as a yellow liquid and 152 mg (19%) of PRB-25 as a yellow liquid. PRB-26:

$^1$H NMR (200 MHz, CDCl$_3$) δ 0.89 (t, J=7.5 Hz, 3H), 1.03 (t, 3H), 1.24 (t, J=7.1 Hz, 6H), 2.05 (quint, J=7.1 Hz, 2H), 2.52 (m, 4H), 2.76-2.85 (m, 12H), 3.35 (t, 1H), 4.13 (q, J=7.1Hz, 2H), 5.28-5.44 (m, 12H)

$^{13}$C NMR (75 MHz, CDCl$_3$) δ 14.1, 14.3, 14.4, 20.5, 22.6, 25.5, 25.6, 25.7, 31.9, 44.4, 60.1, 62.9, 127.0, 127.8, 128.05, 128.13, 128.17, 128.22, 128.5, 132.0, 173.3 (5 signals hidden)

EXAMPLES

Figure 2:
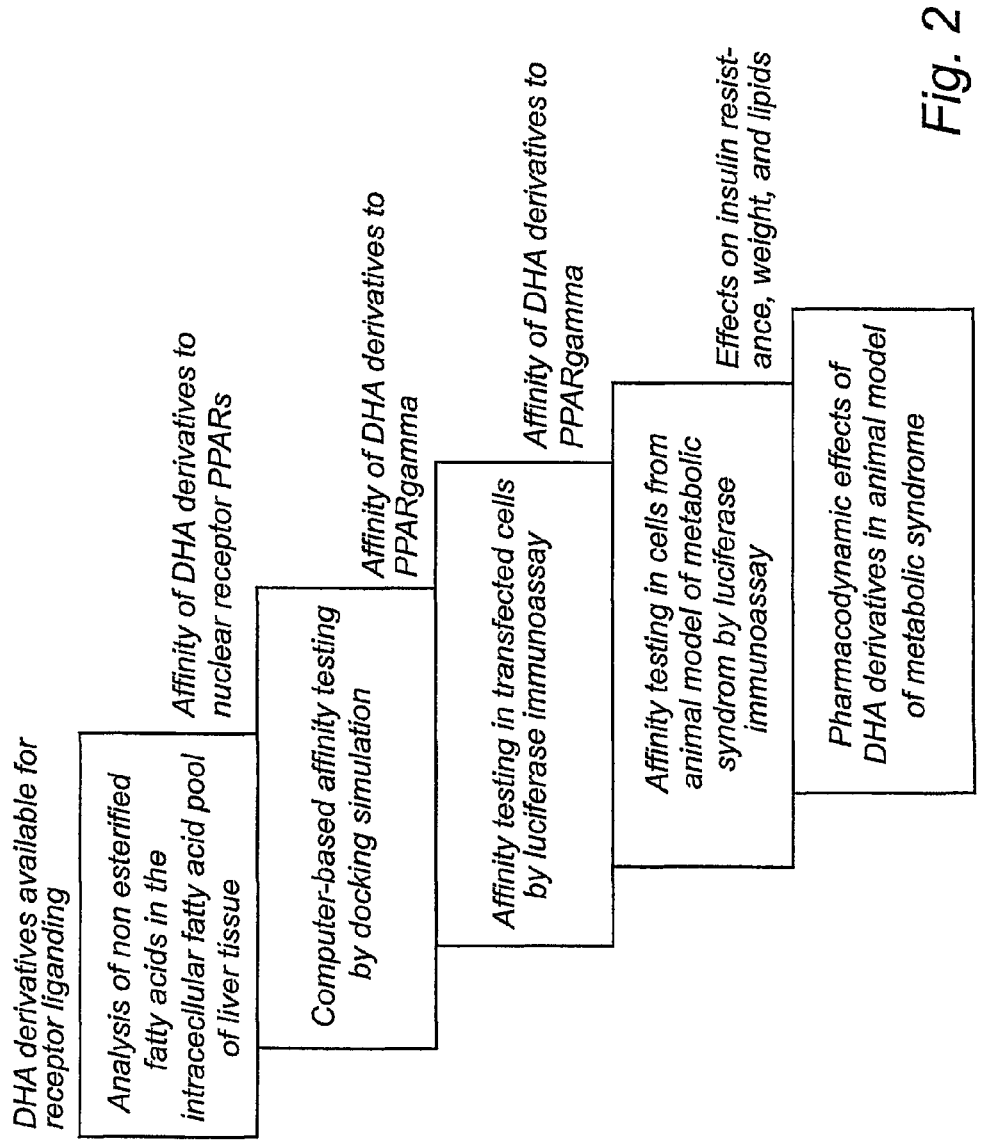
FIG. 2 shows an overview of the models and methods used in the present invention for demonstrating effects on the metabolic syndrome and type 2 diabetes

An overview of the models and methods used in the present invention for demonstrating effects on the metabolic syndrome and type 2 diabetes are presented in FIG. 2. Five blocks of experiments have been performed in order to elucidate the effects of DHA derivatives for reduction of insulin resistance and/or alleviating the metabolic syndrome. The invention shall not be limited to the shown embodiments and examples.

Example 1

Analysis of Intracellular Free Fatty Acids (Non-Esterified Fatty Acids) in Liver Cells (Block 1 in FIG. 2)
Background In the first block of experiments (see FIG. 2) liver tissue from animals fed PRB-1,2,5, and 7 was analysed with respect to free unesterified fatty acids. The animals were recruited from the fifth block of experiments (pharmacodynamic effects of DHA derivatives in an animal model of metabolic syndrome). The animals had been given DHA (15% of fat content of the diet) or the DHA-derivatives (1,5% of the fat content in their diet) for 8 weeks and were supposed to be in a steady-state situation with stable levels of DHA and the DHA-derivatives intracellularly. Liver tissue was chosen due to the fact that the metabolization rate is very high in liver.
Method The liver samples were homogenized in cold PBS buffer, and extracted immediately with chloroform:methanol (2:1) containing 0.2 mM butylated hydroxytoluene (BHT) using cis-10-heptadecenoic acid as internal standard. The organic phases were dried under nitrogen, re-dissolved in acetonitrile with 0.1% acetic acid and 10 µM BHT for RP-HPLC MS/MS analysis. Total protein content was measured using Bio-Rad method after homogenization.

Figure 3:
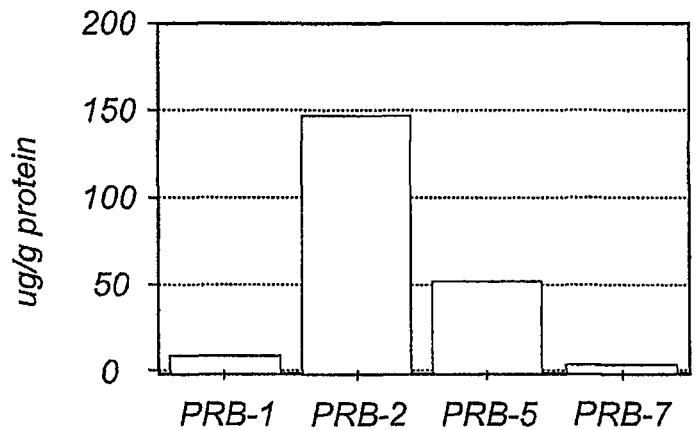
FIG. 3 depicts the free fatty acid concentrations of different compounds according to the invention in liver tissue from animals given these compounds in a concentration of 1.5% of total fat content.

Agilent 1100 system was used for reverse phase column (Supelco Ascentis C$_{18}$ column, 25 cm×4.6 mm, i.d. 5 µm) separation of DHA and its PRB derivatives within 22 min. The flow phase was iso-gradient acetonitrile-H$_2$O (87+13, v/v) containing 0.1% acetic acid. The column oven temperature was set at 35° C. The column elute was identified and quantified in the negative electrospray ionisation applying multiple reaction monitoring mode by triple tandem quadrupole mass/mass (ABI Qtrap-4000). The parent-daughter ion pairs were 327.3/327.3 (DHA), 341.3/341.3 (PRB-1), 355.3/355.3 (PRB-2 and PRB-5), 387.3/387.3 (PRB-7), 267.2/267.2 (I:S. FA 17:1) respectively under unit resolution. The signal collection dwell time was all 100 msec except for FA 17:1 which was set at 200 msec. Accurate verification of isomeric PRB compounds was done by combination of the retention time and characteristic mass/charge ratio. The quadratic regression standard curve was used for quantification after internal standard calibration.
Results Concentration of the different DHA-derivatives and the concentrations of DHA was given as µg per g of total amount of protein in the liver cells. FIG. 3 depicts the concentrations of the different PRBs from animals given PRB-1,2,5 and 7 in a concentration of 1.5% of total fat content in the high fat diet.

The highest intracellular concentration of the PRBs was obtained for PRB-2. Also PRB-5 was enriched intracellularly, although not to the same extent as PRB-2. This finding is unexpected.

Figure 4:
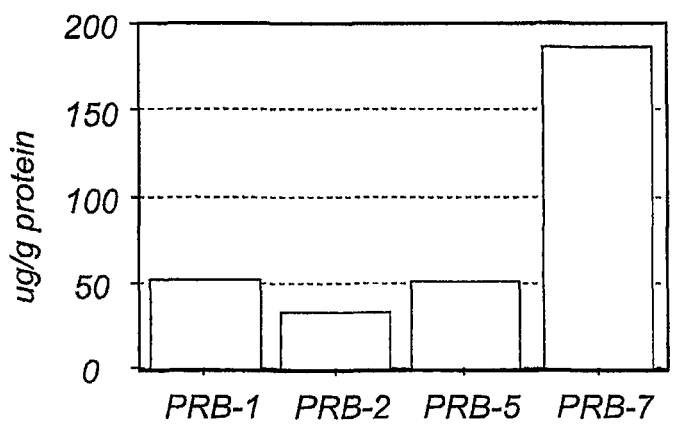
FIG. 4 depicts the intracellular concentrations of DHA in liver tissue from animals given different compounds according to the invention in a concentration of 1.5% of total fat content.

FIG. 4 depicts the intracellular concentrations of DHA in liver tissue from animals given the different PRBs. DHA reached a significantly higher level in the animals given PRB-7 compared to the other three DHA-derivatives. Animals given PRB-2 had the lowest concentration of DHA. It seems that PRB-7 is to some extent converted back to DHA.

PRB-2 reached the highest intracellular concentration. This means that PRB-2 will be more available as a ligand to nuclear receptors, a pattern which could be translated into therapeutic effects in handling of blood glucose and blood lipids.

Example 2

Computer Based Affinity Testing (Block 2 in FIG. 2)
Background

Nuclear receptors have been sequenced and the amino acid sequence is known for the PPARs and other relevant receptors engaged in the genetic control of glucose and fat. X-ray crystallography and NMR spectroscopy of the PPAR receptors are available and computerised affinity testing of fatty acids liganding to the receptors can be used to estimate binding kinetics. The binding geometrics, often called binding modes or poses, include both positioning of the ligand relative to the receptor and the conformational state of the ligand and the receptor. Effective ligand docking can therefore be analysed.

Affinity of the ligand to the receptor is defined by two different parameters: docking of the ligand (DHA derivative) into the binding site of the receptor and electrostatic bonding between certain amino acids of the receptor and the carboxyl group or side chains in the head of the fatty acid. (Krumrine).

As previously known, the PPARα receptor is more promiscuous compared to PPARγ, meaning that PPARα will accept more fatty acids as ligands compared to PPARγ. However, since patients with metabolic syndrome or type 2 diabetes are usually obese or overweight and have pathologic blood lipids; mainly elevated triglycerides and low High-Density Cholesterol (HDL-chol) activation of the PPARα receptor is important. An ideal drug for treatment of metabolic syndrome or type 2 diabetes should act as ligand to both these receptors, preferably with the highest affinity to the PPARγ receptor.
Method Ranking of the different DHA-derivatives according to their binding affinity was calculated and given as lowest binding affinity (LBA) and average binding affinity (ABE).

A total of 15 DHA derivatives (PRB-1 through PRB-15) were tested with the computerized docking method. Some of the derivatives, such as PRB-1, PRB-2, PRB-7, PRB-9, PRB-10, PRB-11, PRB-12, PRB-13, PRB-14 and PRB-15, are presented as r and s enantiomers and in this case both were tested. The PPARγ ligands rosiglitazone and pioglitazone, both in the r and s form, were also tested for comparison. These compounds are registered pharmaceuticals for treatment of diabetes.
Results The results are shown in Table 1, presenting the parameters Lowest binding energy of single confirmation (LBE), average binding energy (ABE) of the correctly posed confirmation and fraction of correctly posed confirmation of the ICMsaved 20 lowest energy confirmation (Mound) of the compounds tested. Affinity to the RXRα was tested in the same setting. The RXRα receptor interacts with the PPAR receptor forming a heterodimer by liganding of a fatty acid.

Figure 5:
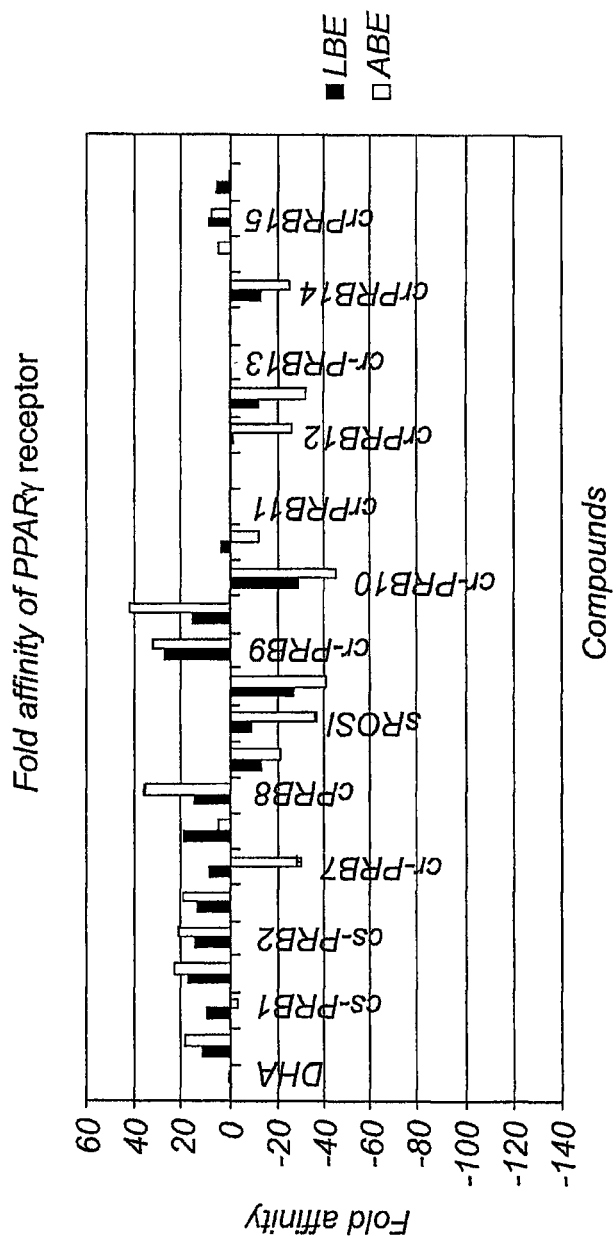
FIG. 5 depicts the binding affinities for the PPARγ receptor of different compounds according to the invention.

FIG. 5 depicts the binding affinities for the PPARγ receptor, which is mainly engaged in the transcription of proteins engaged in handling of blood glucose. Clearly PRB-2 both in the r and the s stereoisomer forms had a good affinity to the PPARγ receptor. PRB-5 scored somewhat poorer while PRB-8 had the highest ABE score. These findings are highly unsuspected and could be translated into a more effective transcription of the respective PPARγ activated gene responsible for handling of blood glucose.

Figure 6:
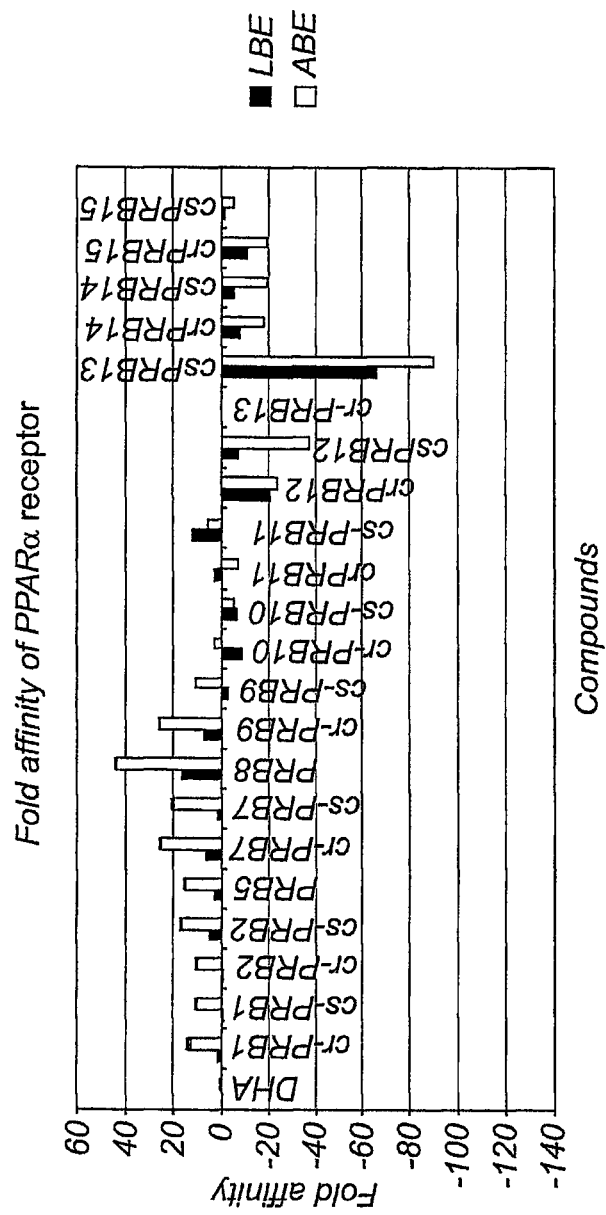
FIG. 6 depicts the binding affinities to the nuclear receptor PPARα of different compounds according to the invention.

FIG. 6 depicts the binding affinities to the nuclear receptor PPARα which is mainly responsible for metabolization of fat, blood lipids, fat tissue biology and weight control. Several DHA-derivatives had high binding affinity but PRB8 had the highest score. This is also highly unsuspected.

Figure 7:
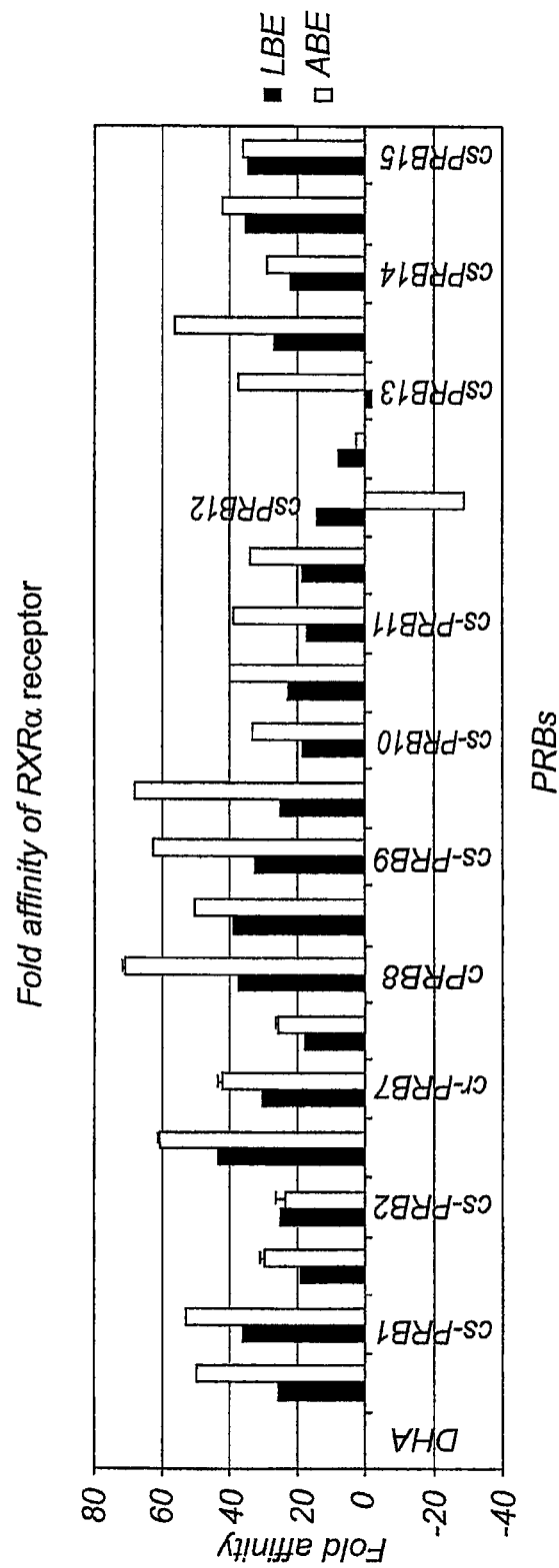
FIG. 7 depicts the binding affinities to the nuclear receptor RXRα of different compounds according to the invention.

FIG. 7 depicts the binding affinities to the nuclear receptor RXRα. The physiologic consequence of binding to the RXRα receptor has not been firmly established. It is known that RXR binds to the PPAR receptors thereby forming a heterodimer which then, subsequently, initiates transcription of the defined gene.

Several of the PRBs have a high LBE and ABE score for the PPARα and PPARγ receptors even compared to the mother compound DHA but also to the PPARγ ligands rosiglitazone and pioglitazone, both in the r and s form. This is an interesting observation indicating that several of the PRBs could be promising competitors to the established anti-diabetics rosiglitazone and pioglitazone.

Ethyl derivatives in alfa position of the same fatty acids, both the r and the s form, did not improve affinity. This was especially true for the PPARγ receptor. As mentioned previously the PPARα receptor is more promiscuous binding a long series of fatty acids.

In conclusion, many of the DHA-derivatives tested demonstrated interesting affinities to the PPARα and PPARγ receptors with binding affinities better than rosiglitazone and pioglitazone.

Example 3

Affinity Testing in Transfected Cells (Block 3 in FIG. 2)
Background

Release of luciferase is correlated to transcription of genes. Binding of a ligand to a nuclear receptor such as PPARγ induces transcription of the respective gene thereby releasing

TABLE 1

| | PPARα | | | PPARγ | | | RXRα | | |
|---|---|---|---|---|---|---|---|---|---|
| | LBE | ABE | $f_{bound}$ | LBE | ABE | $f_{bound}$ | LBE | ABE | $f_{bound}$ |
| DHA | −16.14 | −13.29 (0.47) | 0.60 | −11.34 | −10.51 (0.21) | 0.35 | −12.15 | −10.72 (0.29) | 0.40 |
| cr-PRB1 | −16.29 | −14.25 (0.53) | 0.50 | −12.96 | −11.82 (0.38) | 0.30 | −15.68 | −14.25 (0.35) | 0.30 |
| cs-PRB1 | −15.97 | −14.01 (0.30) | 0.80 | −12.74 | −10.24 (0.48) | 0.65 | −17.17 | −14.48 (0.44) | 0.50 |
| cr-PRB2 | −16.00 | −14.02 (0.54) | 0.50 | −13.72 | −12.17 (0.54) | 0.25 | −14.81 | −12.80 (1.56) | 0.20 |
| cs-PRB2 | −16.86 | −14.48 (0.27) | 0.85 | −13.34 | −12.05 (0.30) | 0.60 | −15.57 | −12.39 (2.20) | 0.20 |
| PRB5 | −16.54 | −14.37 (0.40) | 0.65 | −13.16 | −11.88 (0.30) | 0.50 | −18.21 | −15.028 1.03) | 0.30 |
| cr-PRB7 | −17.06 | −15.09 (0.32) | 0.80 | −12.52 | −8.34 (2.30) | 0.50 | −16.35 | −13.72 (0.96) | 0.30 |
| cs-PRB7 | −16.31 | −14.72 (0.37) | 0.65 | −14.00 | −10.84 (0.40) | 0.55 | −14.63 | −12.52 (0.84) | 0.30 |
| PRB8 | −18.45 | −16.41 (0.57) | 0.45 | −13.39 | −13.04 (0.35) | 0.10 | −17.31 | −15.79 (0.57) | 0.30 |
| sROSI | | | | −9.47 | −9.01 (0.17) | 0.20 | | | |
| sROSI | | | | −10.05 | −7.89 (0.91) | 0.20 | | | |
| rPIO | | | | ND | | | | | |
| sPIO | | | | −7.59 | −7.59 | 0.05 | | | |
| cr-PRB9 | −17.15 | −15.12 | 0.35 | −15.14 | −12.84 | 0.25 | −17.56 | −14.30 | 0.15 |
| cs-PRB9 | −15.66 | −14.06 | 0.45 | −13.50 | −13.50 | 0.05 | −16.63 | −15.20 | 0.15 |
| cr-PRB10 | −14.88 | −13.46 | 0.25 | −7.31 | −7.31 | 0.05 | −15.59 | −15.58 | 0.10 |
| cs-PRB10 | −15.17 | −12.90 | 0.50 | −11.78 | −9.64 | 0.20 | −14.75 | −13.05 | 0.30 |
| crPRB11 | −16.50 | −12.76 | 0.30 | ND | ND | ND | −15.26 | −13.56 | 0.10 |
| cs-PRB11 | −17.77 | −13.66 | 0.20 | ND | ND | ND | −14.48 | −13.48 | 0.20 |
| cr-PRB12 | −13.23 | −11.61 | 0.65 | −11.11 | −8.61 | 0.30 | −14.73 | −13.13 | 0.35 |
| cs-PRB12 | −15.10 | −10.60 | 0.55 | −9.64 | −8.20 | 0.45 | −14.08 | −8.67 | 0.60 |
| cr-PRB13 | ND | ND | — | ND | ND | ND | −13.20 | −10.95 | 0.25 |
| cs-PRB13 | −6.89 | −6.89 | 0.05 | ND | ND | ND | −11.84 | −13.10 | 0.50 |
| cr-PRB14 | −14.96 | −11.99 | 0.60 | −9.50 | −8.72 | 0.20 | −15.84 | −14.77 | 0.20 |
| cs-PRB14 | −15.42 | −11.89 | 0.40 | −11.29 | −10.87 | 0.20 | −15.22 | −12.77 | 0.30 |
| cr-PRB15 | −14.62 | −11.88 | 0.45 | −12.49 | −11.05 | 0.45 | −17.01 | −13.73 | 0.45 |
| cs-PRB15 | −15.90 | −12.90 | 0.40 | −12.15 | −10.55 | 0.50 | −16.93 | −13.27 | 0.60 |

ND = Not docked, c = the double bonds in all-cis form. r = R enantioisomer, s = S enantioisomer. ROSI = Rosiglitazone, PIO = Pioglitazone luciferase. This technique therefore provides a measure of ligand affinity to the receptor as well as activation of the responsible gene.

Method

Transient transfection of COS-1 cells was performed in 6-well plates as described by Graham and van der Eb (Graham). For full length PPAR transfection studies, each well received 5 µg reporter construct, 2.5 µg pSV-β-galactosidase as an internal control, 0.4 µg pSG5-PPARγ2. The cells were harvested after 72 h, and the luciferase activity was measured according to the protocol (Promega). The luciferase activity was normalized against β-galactosidase activity. The adipocytes were transfected at D11 of differentiation using 16 µl LipofectaminPlus reagent, 4 µl Lipofectamine (Life Technologies Inc.), 0.2 µg pSG5-PPARγ, and 100 ng pTK Renilla luciferase as control of transfection efficiency. Three hours after transfection, cells were cultured in serum containing medium and incubated for 48 hours in the same medium containing appropriate agents. The luciferase activities were measured as recommended by the manufacturer (Dual Luciferase assay, Promega). All transfections were performed in triplicate.

Figure 8:
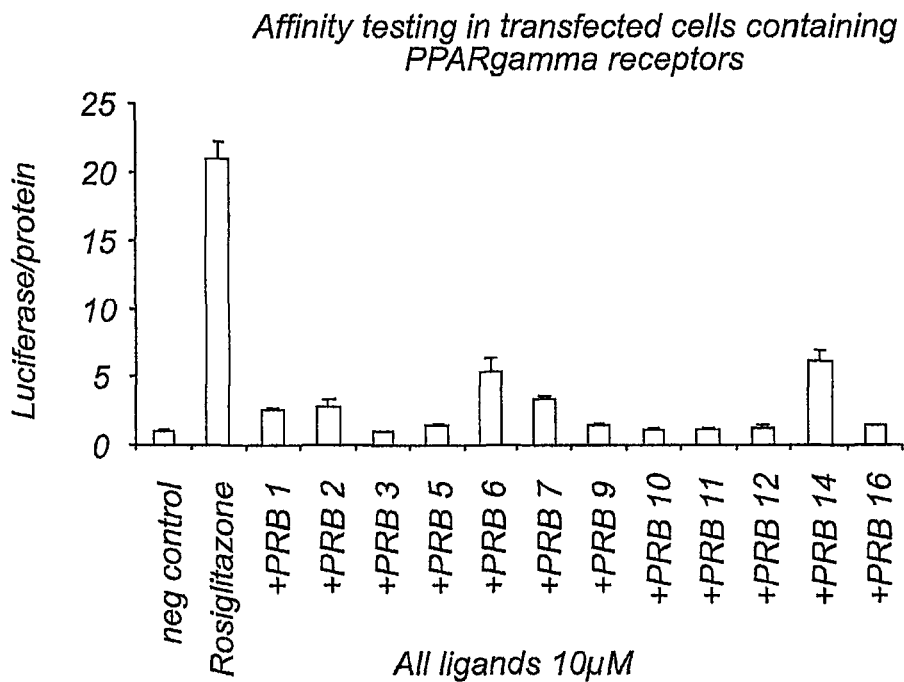
FIG. 8 depicts the release of luciferase from transfected cells treated with different compounds according to the invention.

Fatty acids (BRL or DHA) and PRBs (stock solutions) were solubilized to 0.1 M final concentration in DMSO. Then, Fatty solubilized to 10 mM in DMSO and stored in 1.5 ml tubes (homopolymer, plastic tubes) flushed with argon and stored at −20° C. 10 µM of PRBs or fatty acids and DMSO (control) was added to the media 5 h after transfection. Transfected cells were maintained for 24 h before lysis by reporter lysis buffer. Binding of PRBs or fatty acids to the LBD of PPAR activates GAL4 binding to UAS, which in turn stimulates the tk promoter to drive luciferase expression. Luciferase activity was measured using a luminometer (TD-20/20 luminometer; Turner Designs, Sunnycvale, Calif.) and normalized against protein content Results FIG. 8 depicts the release of luciferase from transfected cells treated with different PRBs. The results indicate that PRB-1,2,6,7 and 14 have a significantly higher release of luciferase compared to PRB-3,5,9,10,11,12, and 16.

Example 4

Affinity Testing in Adipose Prone Animals with Metabolic Syndrome (Block 4 in FIG. 2)

Background

Figure 9:
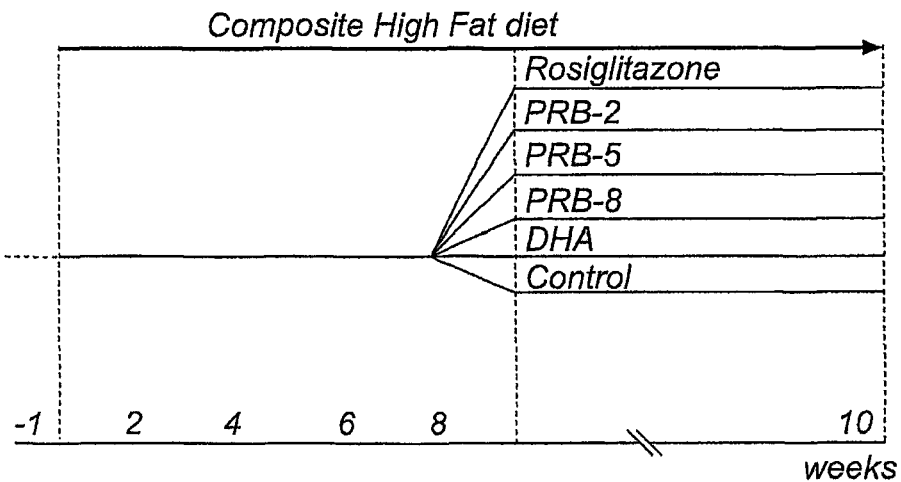
FIG. 9 shows the study design of the experiment of block 4.

An animal model of the metabolic syndrome using the adipose prone mice of the C57BL/6J strain was used to test affinity of PRB-2,5, and 8 compared to 97% DHA and the antidiabetic compound rosiglitazone to PPARγ, by measuring the release of luciferase from adipose cells taken from these animals. The animals (n=8 in each group) were fed high fat diet (fat constituting 60% of total calories, the same diet as used in Block 5) for 8 weeks. Thereafter they were given the PRBs in a dose of 1.5% of the fat content of the diet for another two weeks. The rosiglitazone group was given an amount of 100 mg/KG diet. The control groups continued with either only high fat diet or standard chow. FIG. 9 shows the study design.

Method

After sacrifice adipose tissue (epididymal and subcutaneous) was cleared from other structures and cut into millimeter-size pieces. Fat tissue was rinsed in 0.9% NaCl and digested in 5 mL of Krebs-Ringer solution containing Hepes, fatty-acid free bovine serum albumin, 200 nM of adenosin, 2 nM of glucose, and 260 U/mL of collagenase for 1,5 h at 37 degrees C. in a shaking water bath. After collagenase digestion, adipocytes were separated from tissue debris by filtering. Cells were then washed in Krebs-Ringer solution containing Hepes, fatty-acid free bovine serum albumin, 200 nM of adenosin, 2 nM of glucose and kept in a shaking water bath at 37 degrees for a maximum of 30 min until electroporation.

Isolated primary adipocytes were transfected by electroporation to measure the specific PPAR gamma response element (PPRE) activity. In this case we incorporated a plasmid encoding firefly luciferase cDNA under control of a PPRE from the acyl-CoA-oxidase gene. The cells were also co-transfected with a plasmid containing cDNA for Renilla luciferase controlled by a constitutively active promoter. The PPRE inducible firefly luciferase activity was normalized according to Renilla luciferase, thus correcting for potential differences in the amount of transfected cells. To measure luciferase signal we used the Dual-Luciferase® Reporter assay System (Promega, USA).

Pooled epidydimal fat tissue was enough to isolate adipocytes for running duplicates. Each of groups was sacrificed in two separated days, and 4 independent transfections for each dietetic group were obtained.

Results

Figure 10:
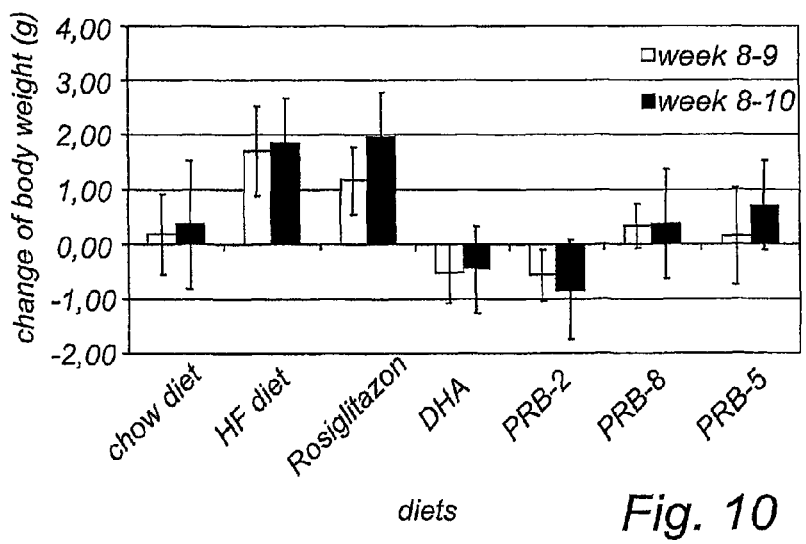
FIG. 10 shows the change of body weight during 2 weeks of diet intervention after 8 weeks of HF diet.

During first 8 weeks of feeding with HF diet (33.7% of fat, w/w), there was a gradual increase of body weight in comparison to control mice fed with chow diet (4,5% w/w). During last 2 weeks of feeding with experimental diets high fat diet animals and animals given high fat diet in combination with Rosiglitazon continued gaining weight, approximately with the same rate as before. In case of PRB-8 and PRB-5 enriched HF diet the weight gain was reduced. However, in case of PRB-2 and DHA (5% w/w) the diet completely stopped the weight gain and even led to reduction of body weight (FIG. 10). Food consumption was recorded occasionally (4×). There were no differences between the HF and the intervention groups.

Figure 11:
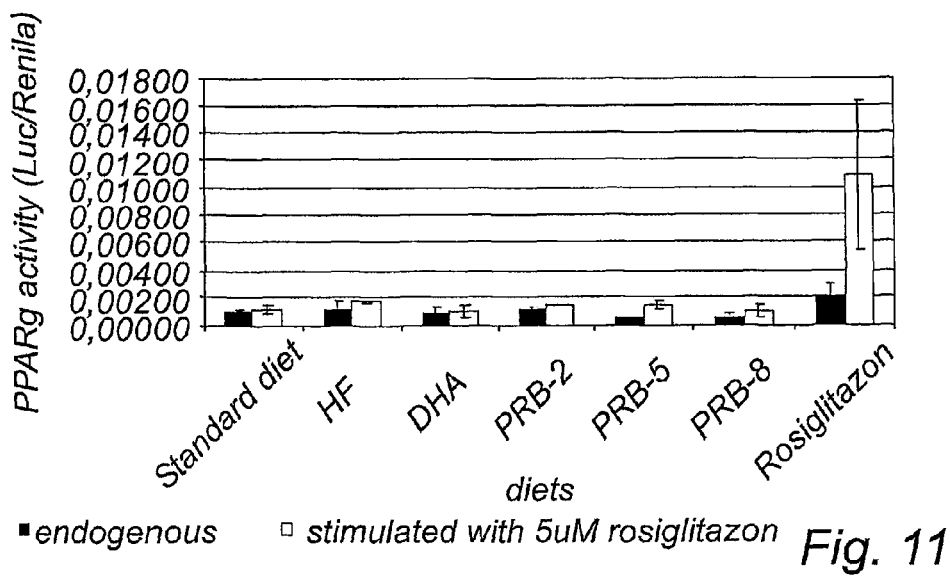
FIG. 11 shows the results from luciferase activity, i.e. endogenous PPARγ—activity).

In case of high fat in combination with Rosiglitazon, the endogenous activity of PPARγ was approximately 2-fold higher than in all the others diet groups (FIG. 11). Furthermore, these fat cells became more sensitive to additional in vitro stimulation with 5 uM Rosiglitazon (5,12-fold stimulation) in comparison to i.e. HF diet itself (1,5-fold stimulation). This rosiglitazon—sensitizing effect was also recorded in the PRB-2 and the PRB-5 diet group (2.6-fold stimulation).

Figure 12:
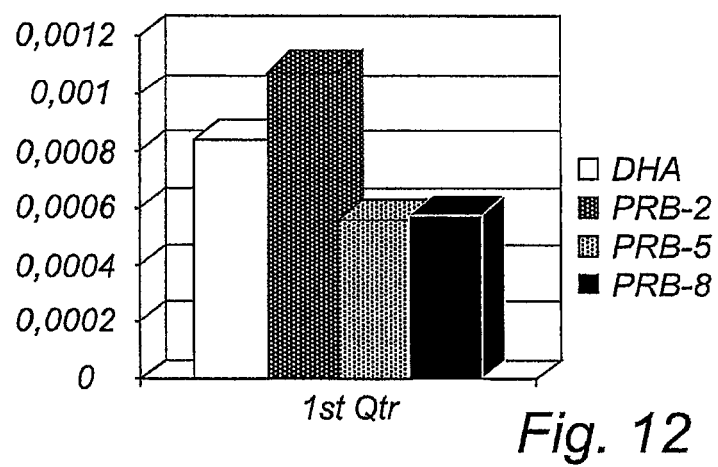
FIG. 12 shows the endogenous luciferase activity in difference compounds according to the invention compared to DHA.

Data from this study clearly demonstrates activity on the nuclear PPAR receptors, in particular with the effects on weight which was most prominent for the groups given PRB-2. Even animals given PRB-5 and PRB-8 did not increase in weight as did the high fat diet group. Interestingly animals given rosiglitazone increased in weight to the same extent as animals given only the high fat diet. This clearly demonstrates the negative effects of giving only a PPARγ ligand, like the glitazones, with the risk of weight increase even if insulin resistance is reduced. However, when it comes to PPARγ activation measured as luciferase activity in this experiment, rosiglitazone scores higher compared to any of the PRBs. Within the PRB groups PRB-2 and PRB-5 had a higher score compared to PRB-8 and DHA only (FIG. 12).

Example 5

Pharmacodynamic Effects of DHA Derivatives in an Animal Model of Metabolic Syndrome (Block 5 in FIG. 2)

Background

An animal model of the metabolic syndrome using the adipose prone mice of the C57BL/6J strain was used to document effects on typical laboratory and pathological anatomical features common for the metabolic syndrome. When given a high fat diet containing about 60% of fat, the animals are getting obese developing high insulin plasma levels, pathological glucose tolerance test, elevated serum triglycerides and non-esterified fatty acids, and fat liver.

Example 5a

Effect of MIA Derivatives in Adipose Prone Mice During 4 Months of Dietary Interventions Method All experiments were performed on male C57BL/6 mice, either a substrain C57BL/N (supplier: Charles River, Germany, n=160, experiments A-C, see below), or a substrain C57BL/6J (supplier: the Jackson laboratory, Bar Harbor, Me., USA, n=32, experiment D). Total numbers of animals used were higher (n=170 and 36, respectively), because of culling. In the latter case, animals were bred for several generations (<20) at the Institute of Physiology. At the beginning of the treatment, animals were 14-week-old and their body weight range was 23.6-27.1 g. One week before the study start, animals were sorted according to their body weight and assigned to subgroups (n=8) of similar mean body weight. This method allowed for culling of about 5-10% of animals showing the lowest and highest body weight, respectively. The animals eliminated from the study at this stage were sacrificed by cervical dislocation. Complete health check of mice was performed by the supplier Charles River and at the start of study serological tests were performed by ANLAB (Prague, Czech Republic). In addition, regular health checks were performed in the animal house in 3-mo-intervals using sentinel mice and serological examinations (ANLAB). In all the tests, the animals were free of specific pathogens.

Diets

Animals were fed 3 types of experimental diets:
  (i) Chow diet (ssniff R/M–H from SSNIFF Spezialdieten Gmbh, Soest, Germany; see also http://ssniff.de) with protein, fat and carbohydrate forming 33, 9, and 58 energy %, respectively
  (ii) High-fat diet prepared in the laboratory (cHF diet) with protein, fat and carbohydrate forming 15, 59, and 26 energy %, respectively, and well characterized fatty acid composition (with most of the lipids coming from corn oil; see Ruzickova 2004)
  (iii) cHF diets in which 0.15, 0.5, and 1.5% of fat (specifically the corn oil constituent) was replaced by various PRB-compounds, namely PRB1, PRB2, PRB5, PRB7, and PRB8, or by DHA; All these compounds were in the form of ethyl esters, provided by Pronova Biocare a.s. in sealed containers. Chemical composition of the PRB-compounds was unknown to the laboratory performing the experiments (Institute of Physiology, Academy of Sciences Prague, Czech Republic).

After arrival, the PRB-compounds were stored in a refrigerator in original containers. The containers were opened just before preparation of the experimental diets. Diets were kept in plastic bags flushed by nitrogen and stored at −70° C. in small aliquots sufficient for feeding animals for one week. Fresh ratios were given in 2-day intervals or daily.

Outline of the Study

The study was based on 4 individual experiments. In each of the experiments, different PRB-compounds (or DHA, respectively) admixed to cHF diet in three different concentrations (0.15, 0.5, and 1.5% of the fat content) were tested. In each experiment, a subgroup of plain cHF diet-fed mice was included and served as a control. Mice were caged in groups of 4 and fed standard chow diet until 3 mo of age, when animals (n=8-13) were randomly assigned to the different test diets. After 2 mo on this new diet (at 5 mo of age), animals were fasted overnight and in the morning, intraperitoneal Glucose Tolerance Test (OTT) was performed. Animals were sacrificed after 4 months on the experimental diets, at 7 mo of age, and the end-point analysis were performed.

Study Parameters.

The parameters in the study were: Body weight gain (grams), area under the curve (AUC) from intraperitoneal glucose tolerance tests (mMol×180 min), plasma insulin (ng/ml), serum triglycerides (TAGs, mmol/l), and non-esterified fatty acids (NEFA, mmol/l).

Figure 13:
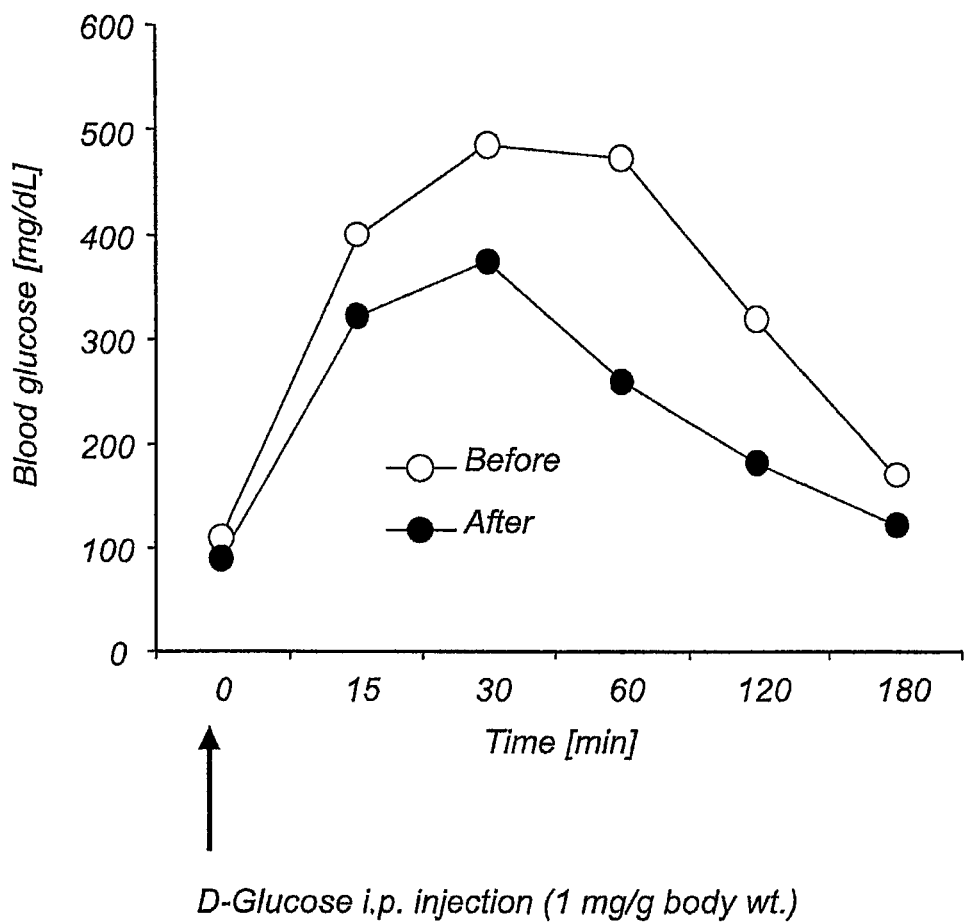
FIG. 13 shows a typical blood glucose elimination curve before and after animals with insulin resistance are given a compound with insulin resistance reducing effect.

FIG. 13 shows a typical blood glucose elimination curve before and after animals with insulin resistance are given a compound with insulin resistance reducing effect. Reduction of the area wider the curve means that blood glucose is eliminated more effectively due to reduced insulin resistance.

Results

The results are shown in the following tables 2, 3 and 4. (*=significant differences compared to cHF diets (P<0.05).)

Table 2 shows the effects in animals given 1.5% concentration of the PRB test compounds compared to animals given standard chow (STD), composite high fat diet (cHF) or 97% DHA. Body weight gain was significantly reduced in animals given PRB-2 compared to animals given high fat diet (cHF). Food intake was somewhat lower in this group. The most pronounced reduction in AUC from glucose tolerance tests was seen in the same group and even in animals given PRB-1. Plasma insulin was significantly lower in the PRB-2 group compared to the cHF controls even if the PRB-1 and PRB-5 treated animals showed some effect on this parameter too. The PRB-2 group showed the biggest reduction in triglycerides (TAGs) and non-esterified fatty acids (NEFA).

Table 3 shows the effects in animals given a lower concentration, 0.5%, of the PRB test compounds compared to animals given standard chow (SW), composite high fat diet (cHF) or 97% DHA. Body weight gain was somewhat lower in animals given PRB-2 and PRB-5. AUC from the glucose tolerance test as well as plasma insulin, however, was significantly lower only in the PRB-2 group.

Table 4 shows the results from the lowest PRB concentration given, 0.15%. Here, the differences were small. Weight gain was somewhat lower in the PRB-1 and PRB-2 groups while AUC was significantly lower only in the PRB-2 group. Plasma insulin was lower in PRB-1,2 and 7.

TABLE 2

The effect of PRB derivatives after 4 months of treatment with 1.5% concentration

| Parameter | STD | cHF | PRB-1 | PRB-2 | PRB-5 | PRB-7 | DHA |
|---|---|---|---|---|---|---|---|
| Body weight (grams) | 32.4 ± 0.7 | 49.6 ± 0.6 | 44.0 ± 1.5* | 30.1 ± 1.1* | 46.3 ± 1.6 | 45.9 ± 1.1* | 47.1 ± 0.7* |
| Body wt. gain (grams) | 7.8 ± 0.4 | 25.2 ± 0.5 | 20.2 ± 1.3* | 6.4 ± 0.8* | 22.4 ± 1.4 | 21.7 ± 0.9* | 23.0 ± 0.8* |

TABLE 2-continued

The effect of PRB derivatives after 4 months of treatment with 1.5% concentration

| Parameter | STD | cHF | PRB-1 | PRB-2 | PRB-5 | PRB-7 | DHA |
|---|---|---|---|---|---|---|---|
| Food intake (grams/mouse/day) | 3.64 ± 0.04 | 2.70 ± 0.02 | 2.64 ± 0.03 | 2.38 ± 0.05* | 2.62 ± 0.02 | 2.68 ± 0.03 | 2.63 ± 0.02 |
| AUCglucose (mM × 180 min) | 1124 ± 57 | 1625 ± 151 | 913 ± 68* | 982 ± 80* | 1264 ± 192 | 1122 ± 73 | 2132 ± 288* |
| Fasted glucose (mg/dL) | 77 ± 3 | 145 ± 7 | 130 ± 14 | 95 ± 6* | 136 ± 12 | 120 ± 9 | 138 ± 7 |
| Insulin (ng/mL) | 1.03 ± 0.09 | 5.35 ± 0.36 | 2.73 ± 0.33 | 0.60 ± 0.18* | 2.47 ± 0.19* | 4.42 ± 0.87 | 6.55 ± 0.31 |
| TAGs (mmol/L) | 1.41 ± 0.09 | 1.45 ± 0.07 | 1.58 ± 0.08 | 0.71 ± 0.01* | 1.19 ± 0.07 | 1.15 ± 0.08 | 1.91 ± 0.26* |
| NEFA (mmol/L) | 0.57 ± 0.05 | 0.61 ± 0.04 | 0.63 ± 0.03* | 0.54 ± 0.03* | 0.72 ± 0.05 | 0.82 ± 0.06 | 0.98 ± 0.07 |

TABLE 3

The effect of PRB derivatives after 4 months of dietary interventions: 0.5% concentration.

| Parameter | STD | CHF | PRB-1 | PRB-2 | PRB-5 | PRB-7 | DHA |
|---|---|---|---|---|---|---|---|
| Body weight (grams) | 32.4 ± 0.7 | 49.6 ± 0.6 | 47.4 ± 0.6 | 45.8 ± 1.7 | 45.7 ± 1.5 | 48.8 ± 0.9 | 46.9 ± 0.7* |
| Body wt. gain (grams) | 7.8 ± 0.4 | 25.2 ± 0.5 | 23.8 ± 0.5 | 21.9 ± 0.6 | 22.0 ± 1.4 | 24.8 ± 0.8 | 22.9 ± 0.7* |
| Food intake (grams/mouse/day) | 3.64 ± 0.04 | 2.70 ± 0.02 | 2.67 ± 0.04 | 2.69 ± 0.04 | 2.63 ± 0.02 | 2.69 ± 0.03 | 2.70 ± 0.03 |
| AUCglucose (mM × 180 min) | 1124 ± 57 | 1625 ± 151 | 1596 ± 205 | 1224 ± 72* | 1581 ± 231 | 1674 ± 203 | 1816 ± 182 |
| Fasted glucose (mg/dL) | 77 ± 3 | 145 ± 7 | 131 ± 7 | 136 ± 7 | 130 ± 7 | 152 ± 6 | 136 ± 8 |
| Insulin (ng/mL) | 1.03 ± 0.08 | 5.35 ± 0.36 | 3.93 ± 0.59 | 2.75 ± 0.21* | 5.12 ± 0.93 | 4.10 ± 0.57* | 5.82 ± 0.47 |
| TAGs (mmol/L) | 1.41 ± 0.09 | 1.45 ± 0.07 | 2.03 ± 0.22 | 1.29 ± 0.08 | 1.46 ± 0.17 | 1.42 ± 0.08 | 1.78 ± 0.08* |
| NEFA (mmol/L) | 0.57 ± 0.05 | 0.61 ± 0.04 | 0.73 ± 0.04* | 0.75 ± 0.04 | 0.77 ± 0.03* | 0.87 ± 0.04 | 0.89 ± 0.03 |

TABLE 4

The effect of PRB derivatives after 4 months of dietary interventions: 0.15% concentration.

| Parameter | STD | cHF | PRB-1 | PRB-2 | PRB-5 | PRB-7 | DHA |
|---|---|---|---|---|---|---|---|
| Body weight (grams) | 32.4 ± 0.7 | 49.6 ± 0.6 | 47.2 ± 1.3 | 46.7 ± 1.1 | 48.0 ± 0.8 | 47.4 ± 0.8* | 48.3 ± 0.6 |
| Body wt. Gain (grams) | 7.8 ± 0.4 | 25.2 ± 0.5 | 22.9 ± 1.1 | 22.8 ± 0.9 | 24.2 ± 0.5 | 23.2 ± 0.7* | 24.3 ± 0.8 |
| Food intake (grams/mouse/day) | 3.64 ± 0.04 | 2.70 ± 0.02 | 2.63 ± 0.04 | 2.57 ± 0.03* | 2.66 ± 0.02 | 2.59 ± 0.02 | 2.79 ± 0.03 |
| AUCglucose (mM × 180 min) | 1124 ± 57 | 1625 ± 151 | 1291 ± 172 | 1071 ± 148* | 1443 ± 70 | 1425 ± 97 | 1477 ± 214 |
| Fasted glucose (mg/dL) | 77 ± 3 | 145 ± 7 | 126 ± 15 | 132 ± 5 | 151 ± 5 | 141 ± 9 | 141 ± 10 |
| Insulin (ng/mL) | 1.03 ± 0.08 | 5.35 ± 0.36 | 3.50 ± 0.29 | 4.00 ± 0.64 | 6.21 ± 0.45 | 3.76 ± 0.72* | 4.31 ± 0.39* |
| TAGs (mmol/L) | 1.41 ± 0.09 | 1.45 ± 0.07 | 1.75 ± 0.08 | 1.42 ± 0.07 | 1.64 ± 0.28 | 1.41 ± 0.11 | 1.50 ± 0.13 |
| NEFA (mmol/L) | 0.57 ± 0.05 | 0.61 ± 0.04 | 0.62 ± 0.04* | 0.78 ± 0.04* | 0.71 ± 0.09 | 0.85 ± 0.06 | 0.96 ± 0.07 |

In conclusion, testing of PBR-1,2,5, and 7 during 4 months in adipose prone animals with insulin resistance and metabolic syndrome demonstrated a clear and unsuspected effect of the PRBs tested, in particular the DHA-derivative PBR-2, on insulin resistance and symptoms of the metabolic syndrome such as weight reduction, reduced AUC in the intraperitoneal glucose tolerance test, lower insulin/plasma levels as well as reduced triglyceride and non-esterified free fatty acids. Effects were observed in the dose of 1.5% as well as in the 0.5% group. Some effects were even noticed in the lowest concentration group of 0.15%.

Testing of the PRB-8 compound was started later, therefore only data from 2 months intervention in three dose groups (1.5%, 0.5% and 0.15%) are given. In the group given 1.5%, body weight (BW) was 28.0±0.7 grams compared to controls 29.6±0.9, AUC 1031±104 compared to 1074±91. These differences are small but the trend is interesting. There were no differences between intervention and controls for the lower doses of 0.5% and 0.15%. The data regarding PRB-8 data from 2 months medication showing a trend towards weight reduction and AUC.

Example 5b

Figure 14:
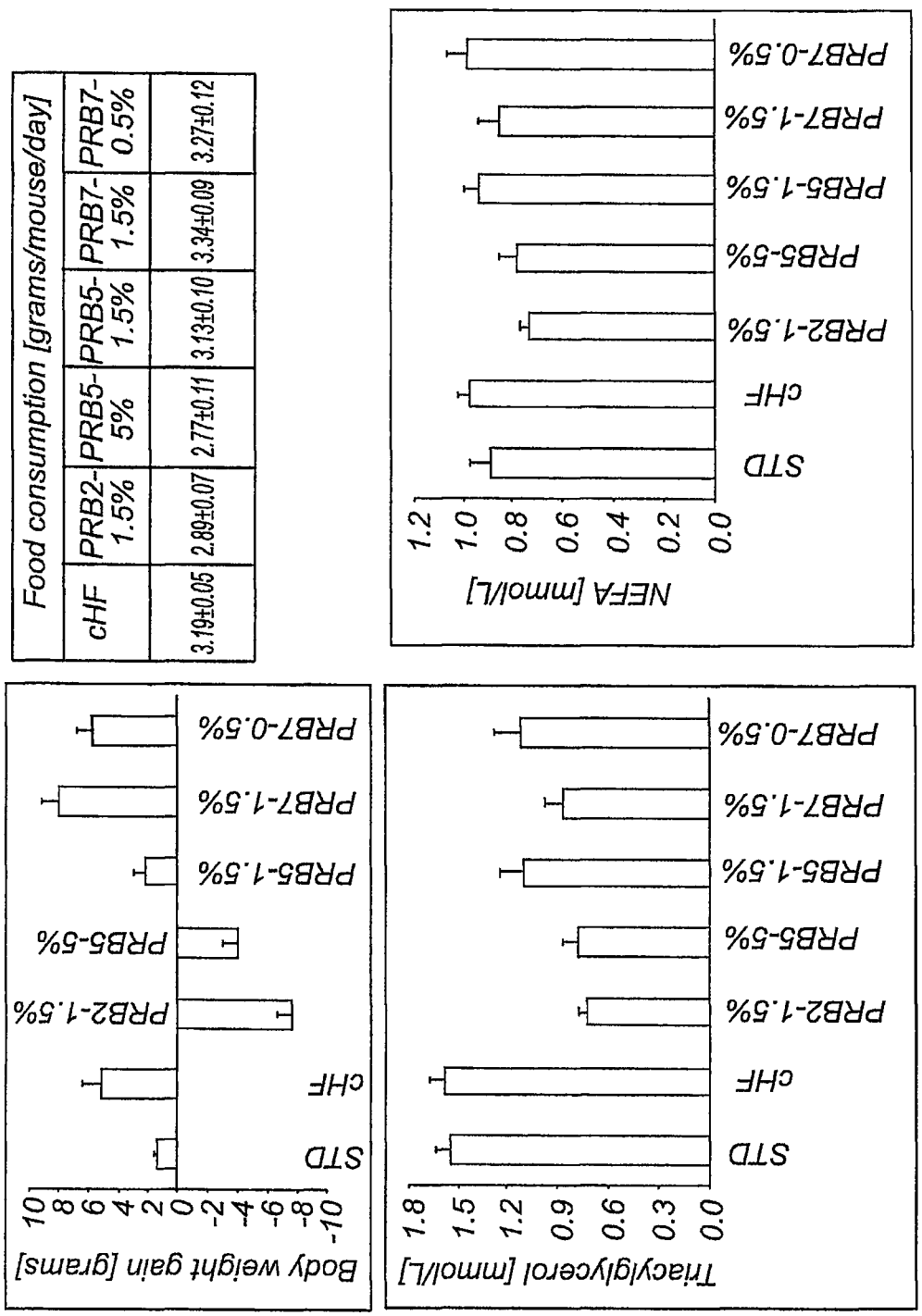
FIGS. 14, 15 and 16 show different effects of DHA derivatives according to the invention on metabolic syndrome and insulin resistance.

Effect of DHA Derivatives on Established Metabolic Syndrome and Insulin Resistance
Method In another experiment, PRB-2, PRB-5, and PRB-7 were tested in the same breed of animals. In this experiment, animals were initially fed high fat diet (the same as in the previous experiment 5a) for 8 weeks developing insulin resistance and the metabolic syndrome, and then given the PRBs. The start dose was to substitute 15% of the fat content with the PRBs but the animals did not tolerate this dose. After a period of another two weeks the animals were given 1.5% of PRB-2, 5% and 1.5% of PRB-5, and 1.5% and 0.5% of PRB-7.
Results Weight reduction was very good in the animals given PRB-2. Even the animals given PRB-5 showed some weight reduction but in the higher dose of 5%. Triglycerides were reduced with all derivatives tested compared to the control animals fed composite High Fat diet. Reduction of non-esterified fatty acids was most pronounced with PRB-2 and PRB-5, however in different doses. (See FIG. 14)

Figure 15:
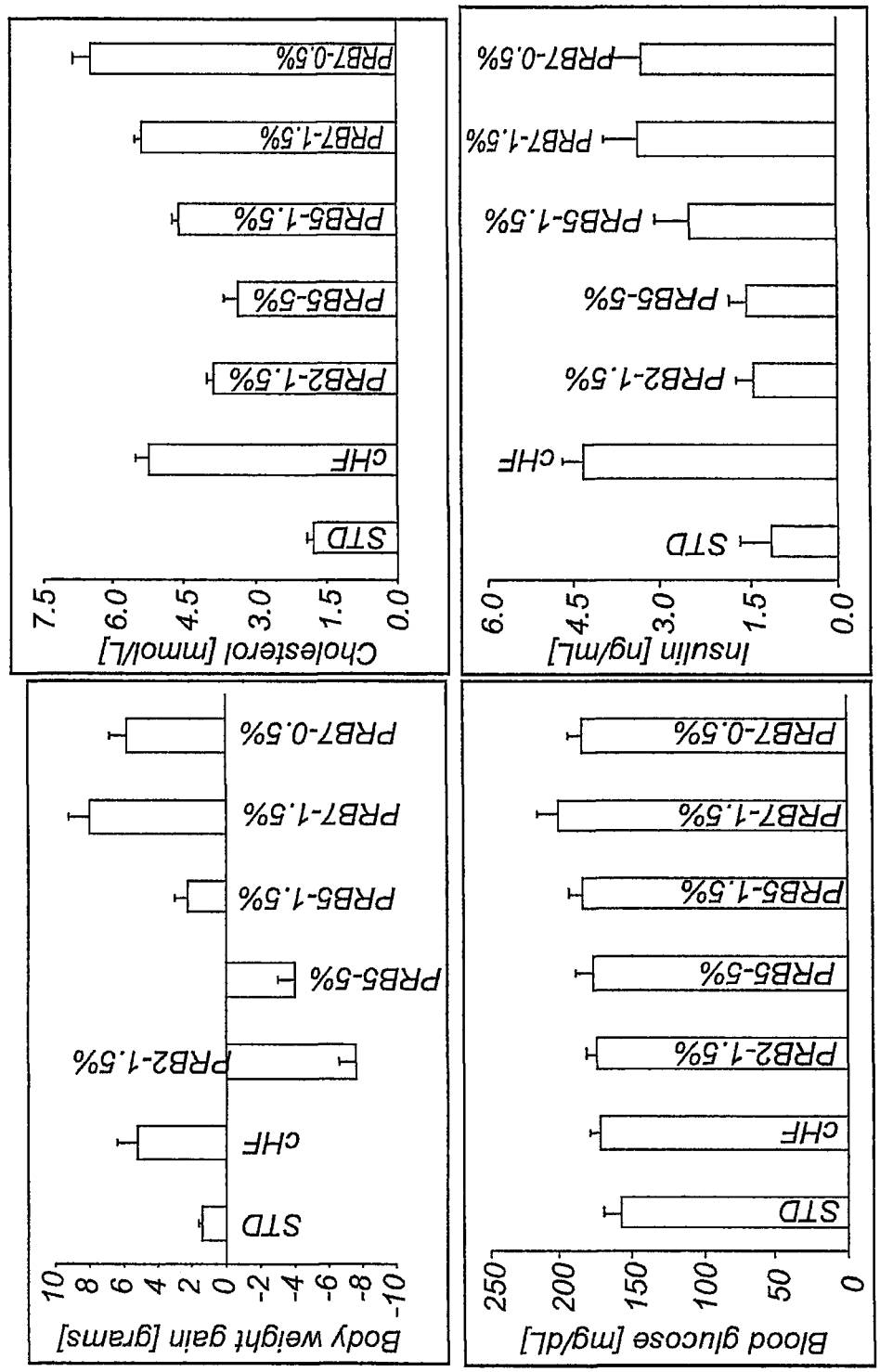

Blood cholesterol was reduced in animals given PRB-2 and PRB-5. Blood glucose was not affected due to the fact that these animals are in a pre-diabetic state with normal glucose due to a high insulin production. However, more importantly, plasma insulin was significantly reduced in the PRB-2 group in a much lower concentration compared to the second best DHA-derivative PRB-5. Even PRB-7 showed some effects on the insulin concentration. (See FIG. 15)

Figure 16:
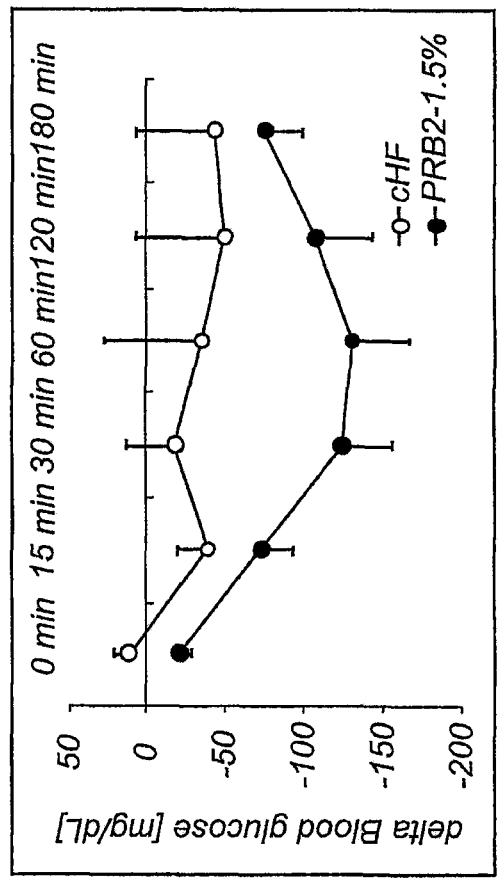

PRB-2 showed a statistically significant reduction of the AUC blood glucose at all time points of the curve compared to the baseline values. This means that blood glucose was more effectively removed after treatment of 1.5% of PRB-2. PBR-5 and PBR-7 showed some effect but not to the same extent. (See FIG. 16)

These effects are highly unsuspected and very relevant for a positive effect in metabolic syndrome and type 2 diabetes. These patients are almost exclusively overweight or obese and a weight reductive effect of a drug is highly positive. The mostly used remedies used for treatment of type 2 diabetes today, the thiazolidinediones, which are potent PPARγ ligands thereby reducing insulin resistance, often result in weight increase which is highly negative for these subset of patients (Yki-Järvinen 2004).

Reduction of serum triglycerides is another very important effect that was demonstrated in the experiments. Patients with metabolic syndrome and type 2 diabetes usually have elevated triglycerides. The triglyceride lowering effects of the DHA-derivatives is a positive finding and again PRB-2 demonstrated the most potent effect with the lowest dose given. The very positive effects on plasma insulin and glucose tolerance test are very promising and highly unsuspected. Taken together the effects obtained with the DHA-derivatives in particular PRB-2 are very promising forming a good basis for development of an antidiabetic drug.

Example 5c

Testing of DHA Derivatives on Liver Fat
Method

Tissue samples from animals in the experiments with DHA derivatives was histologically analysed. After paraffination, tissue samples from liver, adipose tissue, skeletal muscle, pancreas, and kidney were stained with eosin-hematoxylin.
Results There were no pathological findings in the tissues examined with exception from liver. Control animals fed high fat diet had developed fat liver (liver steatosis). Fat droplets in the liver can easily be distinguished from normal liver cells. Animals treated with PRB-1, 5, and 7 had low degree of fat liver. However, animals treated with 1.5% of PRB-2 had completely normal liver cells with no trace of steatosis.

This is an extremely important finding and very relevant for treatment of patients with insulin resistance, obesity and type 2 diabetes. Liver steatosis is a common finding in these patients which is usually related to an overload of fatty acids and triglycerides, biological markers present in the development of insulin resistance and the metabolic syndrome. DHA-derivatives reduce liver steatosis, and PRB-2 was the most efficient compound showing this effect.

Discussion and Conclusions

The present application clearly identifies a new group of compounds which are activating nuclear receptors, especially PPARγ and PPARα, thereby offering a series of therapeutic effects in the treatment of insulin resistance, the metabolic syndrome, type 2 diabetes, cardiovascular disease and other atherosclerotic related diseases.

Members of this group are DHA derivatives with side chains of different kind in the alfa position of the molecule. A large number of alfa-substituted DHA derivatives have been tested and compared with controls as well as pure DHA and EPA. Several of the compounds tested have demonstrated interesting biological effects very relevant for a potential anti-diabetic drug.

Interestingly, and not conceivable on beforehand, alfa-ethyl DHA ethyl ester (PRB-2) was significantly more effective in the battery of tests used to demonstrate effects related to insulin resistance and thereby diseases mainly caused by this pathophysiologic condition such as the metabolic syndrome, type 2 diabetes, cardiovascular disease and other atherosclerotic related diseases. Alfa-ethyl DHA ethyl ester was enriched in liver tissue from animals given the different DHA derivatives tested (Block 1) indicating that this compound was not utilised for synthesis of triglycerides, eicosanoids or other metabolic intermediates. Indirectly this would mean that alfa-ethyl DHA would be available for liganding to nuclear receptors like the PPARs.

In testing of affinity to PPAR γ and PPARα using computerized docking technology a large number of the DHA-derivatives showed affinities to both receptors, not least PPAR γ which probably is the most important nuclear receptor engaged in the activation of genes responsible for metabolization of blood glucose. In particular alfa-ethyl DHA (PRB-2) as well as alfa-diethyl DHA (PBR-8) possessed excellent affinity to these nuclear receptors. Compared to alfa-diethyl DHA alfa-ethyl DHA has two stereoisomers, the r and the s form. Using the docking technology both stereo isomers possessed about the same affinity to PPAR γ and PPARα meaning that neither the r or the s form should have advantages compared to the racemic form. In fact the racemic form may have advantages over each one of the stereoisomers.

When affinity was tested in transfected cells carrying the nuclear receptor and the subsequent DNA response element, several of the PRBs demonstrated good affinity measured as release of luciferase. Alfa-ethyl DHA (PRB-2) together with PRB-6,7 and 14 demonstrated the best effects.

Five of the DHA derivatives have been extensively tested in the C57BL/6 mouse model developing insulin resistance and the metabolic syndrome when fed high fat diet. Alfa-ethyl DHA (PRB-2) has been tested in three individual experiments while PRB-1,5, and 7 were tested in two and alfa-diethyl DHA (PRB-8) was tested in one experiment. All derivatives demonstrated significant biological effects. However, alfa-ethyl DHA (PRB-2) showed the most promising effects with a consistent reduction in body weight, AUC from intraperitoneal glucose tolerance testing, plasma insulin as well as serum triglycerides and non-esterified fatty acids. The effects were obtained on the doses 1.5% and 0.5%. The lowest tested dose 0.15% did not perform convincingly. Alfa-ethyl DHA (PRB-2) in a dose of 1.5% has also demonstrated a normalisation of fat liver, an important pathological finding in patients and animals with insulin resistance and metabolic syndrome.

Comparing with pure DHA, alfa-ethyl DHA (PRB-2) seems to be 10-30 times as potent as DHA. All in all these findings and the potency compared to the mother molecule DHA are not predictable and highly unexpected.

Since alfa-ethyl DHA (PRB-2) seems to work by simultaneous liganding to the nuclear receptors PPARα and PPARγ the compound would not only possess therapeutic interesting effects on glucose and lipid metabolism, not least in patients with insulin resistance, metabolic syndrome and type 2 diabetes but also have weight reduction as well as a general anti-inflammatory effect. Directly or through positive intervention on risk factors alfa-ethyl DHA (PRB-2) would have a preventive effect on the development of cardiovascular disease such as myocardial infarction and cerebral stroke as well as having a preventive effect on cardio-vascular mortality.

Pharmaceuticals acting as PPARγ ligands are already on the market but even if these compounds are having positive effects on glucose metabolism, they are hampered by adverse effects such as elevated triglycerides, weight increase and oedema. The alfa-substituted DHA derivatives presented in this application are having a combined PPARγ and PPARα effect which is probably both relevant and advantageous for patients with insulin resistance, metabolic syndrome and type 2 diabetes. Furthermore, these combinative actions should have important effects also on blood lipids, inflammatory events, atherosclerosis, and thereby cardiovascular disease.

The invention shall not be limited to the shown embodiments and examples.

References

Simonopoulos A P. Essential fatty acids in health and chronic disease. Am J Clin Nutr 1999; 70 (Suppl):560S-569S Geleijnse J M, Giltay E J, Grobbee D E, et al. Blood pressure response to fish oil supplementation: metaregression analysis of randomized trials. J Hypertension 2002; 20:1493-1499

Storlien L H, Hulbert A J, and Else P L. Polyunsaturated fatty acids, membrane function and metabolic diseases such as diabetes and obesity. Curr Opin Clin Nutr Metab Care 1998; 1:559-563

Jump D B. The biochemistry of n-3 polyunsaturated fatty acids. J Biol Chem 2002; 277:8755-8758

Pawar A and Jump D. Unsaturated fatty acid regulation of peroxisomes proliferator-activated receptor alfa activity in rat primary hepatocytes. J Biol Chem 2003; 278:35931-35939

Meigs J B, Wilson P W F, Nathan D M, et al. Prevalence and characteristics of the metabolic syndrome in the San Antonio Heart and Framingham offspring studies. Diabetes 2003; 52:2160-2167

Storlien L H, Kraegen W E, Chisholm D J, et al. Fish oil prevents insulin resistance induced by high fat feeding in rats. Science 1987; 237:885-888

Field C J, Ryan E A, Thomson A B R, et al. Diet fat composition alters membrane phospholipid composition, insulin binding and glucose metabolism in adipocytes from control and diabetic animals. J Biol Chemistry 1990; 265: 11143-11150

Yki-Järvinen, H. Thiazolidinediones. NEJM 2004; 351: 1106-1118

Adams M, Montague C T, Prins J B, et al. Activators of peroxisomes proliferator-activated receptor gamma have depot-specific effects on human preadipocyte differentiation. J Clin Invest 1997; 100:3149-3153

Ruzickovaj, Rossmeisl M, Prazak T, et al. Omega-3 PUFA of marine origin limit diet-induced obesity in mice by reducing cellularity of adipose tissue, Lipids 2004; 39: 1177-1185

Vaagenes H, Madsen L, Dyroy E, et al. The hypolipidaemic effect of EPA is potentiated by 2- and 3-methylation. Biochim Pharmacol 1999; 58:1133-1143

Larsen L, Granslund L, Holmeide A K, et al. Sulfur-substituted and α-methylated fatty acids as peroxisome proliferator-activated receptor activators. Lipids 2005; 40:49-57

Larsen L, Hørvik K, Sørensen H I N, et al. Polyunsaturated thia- and oxa-fatty acids: incorporation into cell-lipids and their effects on arachidonic acid- and eicosanoids synthesis. Biochim et Biophys Acta 1997; 1348:346-354

Larsen, eta) Biochemical Pharmacology 1998; 55, 405

Chih-Hao L, Olson P, and Evans R M. Lipid metabolism, metabolic diseases, and peroxisome proliferator-activated receptors. Endocrinology 2003; 144:2201-2207

Willumsen N, Waagenes H, Holmsen H, et al. On the effect of 2-deuterium- and 2-methyl-eicosapentaenoic acid derivatives on triglycerides, peroxisomal beta-oxidation and platelet aggregation in rats. Biochim Biophys Acta 1998; 1369:193-203

Mitsunobu O, Synthesis 1981; 1

Ager D J, Prakash I, and Schaad D R. 1,2-amino alcohols and their heterocyclic derivatives as chiral auxiliaries in asymmetric synthesis Chem Rev 1996; 96:835-876

The invention claimed is:

1. A method for the treatment of a disease or condition chosen from
   peripheral insulin resistance;
   a diabetic condition;
   obesity or an overweight condition; and/or
   an inflammatory disease or condition;
   comprising administering to a human or animal patient in need thereof a pharmaceutically effective amount of a compound of formula (I)

wherein $R_1$ and $R_2$ are the same or different and are chosen from a hydrogen atom, an alkyl group, a halogen atom, a hydroxy group, an alkoxy group, an acyloxy group, an acyl group, an alkenyl group, an aikynyl group, an aryl group, an alkylthio group, an alkoxycarbonyl group, an alkylsulfinyl group, an alkylsulfonyl group, an amino group, and an alkylamino group; and X represents a carboxylic acid group or a carboxylate group, or any pharmaceutically acceptable salt thereof;

with the provisos that:
the compound of formula (I) is not (all-Z)-4,7,10,13,16,19-docosahexaenoic acid (DHA), alpha-methyl DHA, alpha-methyl DHA methyl ester, alpha-methyl DHA ethyl ester, or alpha-hydroxy DHA ethyl ester, and $R_1$ and $R_2$ are not simultaneously a hydrogen atom.

2. The method according to claim 1, wherein the diabetic condition is Type II diabetes.

3. A method for the treatment of dyslipidemia comprising administering to a human or animal patient in need thereof a pharmaceutically effective amount of a compound of formula (I)

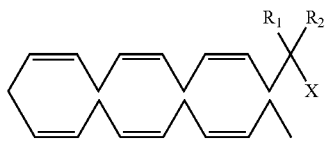

wherein $R_1$ and $R_2$ are the same or different and are chosen from a hydrogen atom, an alkyl group, a halogen atom, a hydroxy group, an alkoxy group, an acyloxy group, an acyl group, an alkenyl group, an alkynyl group, an aryl group, an alkylthio group, an alkoxycarbonyl group, an alkylsulfinyl group, an alkylsulfonyl group, an amino group, and an alkylamino group; and X represents a carboxylic acid group or a carboxylate group, or any pharmaceutically acceptable salt thereof; with the provisos that:
the compound of formula (I) not (all-Z)-4,7,10,13,16,19-docosahexaenoic acid (DHA), alpha-methyl DHA, alpha-methyl DHA methyl ester, alpha-methyl DHA ethyl ester, or alpha-hydroxy DHA ethyl ester, and $R_1$ and $R_2$ are not simultaneously a hydrogen atom.

4. The method according to claim 3, wherein the dyslipidemia is a hyperlipidemic condition.

5. The method according to claim 3, wherein the dyslipidemia includes elevated triglyceride levels and/or non-HDL cholesterol, wherein the non-HDL cholesterol is LDL cholesterol and/or VLDL cholesterol.

6. A method for reducing insulin, blood glucose, and/or serum triglyceride levels by administering to a human or animal patient in need thereof a pharmaceutically effective amount of a compound of formula (I)

wherein $R_1$ and $R_2$ are the same or different and are chosen from a hydrogen atom, an alkyl group, a halogen atom, a hydroxy group, an alkoxy group, an acyloxy group, an acyl group, an alkenyl group, an alkynyl group, an aryl group, an alkylthio group, an alkoxycarbonyl group, an alkylsulfinyl group, an alkylsulfonyl group, an amino group, and an alkylamino group; and X represents a carboxylic acid group or a carboxylate group, or any pharmaceutically acceptable salt thereof; with the provisos that:
the compound of formula (I) is not (all-Z)-4,7,10,13,16,19-docosahexaenoic acid (DHA), alpha-methyl DHA, alpha-methyl DHA methyl ester, alpha-methyl DHA ethyl ester, or alpha-hydroxy DHA ethyl ester, and $R_1$ and $R_2$ are not simultaneously a hydrogen atom.

7. A method for reducing body weight by administering to a human or animal patient in need thereof a pharmaceutically effective amount of a compound of formula (I)

wherein $R_1$ and $R_2$ are the same or different and are chosen from a hydrogen atom, an alkyl group, a halogen atom, a hydroxy group, an alkoxy group, an acyloxy group, an acyl group, an alkenyl group, an alkynyl group, an aryl group, an alkylthio group, an alkoxycarbonyl group, an alkylsulfinyl group, an alkylsulfonyl group, an amino group, and an alkylamino group; and X represents a carboxylic acid group or a carboxylate group, or any pharmaceutically acceptable salt thereof; with the provisos that:
the compound of formula (I) is not (all-Z)-4,7,10,13,16,19-docosahexaenoic acid (DHA), alpha-methyl DHA, alpha-methyl DHA methyl ester, alpha-methyl DHA ethyl ester, or alpha-hydroxy DHA ethyl ester, and $R_1$ and $R_2$ are not simultaneously a hydrogen atom.

8. A method for activating and/or mediating at least one human peroxisome proliferator-activated receptor (PPAR) isoforms by administering to a human or animal patient in need thereof a pharmaceutically effective amount of a compound of formula (I)

wherein $R_1$ and $R_2$ are the same or different and are chosen from a hydrogen atom, an alkyl group, a hydroxy group, a halogen atom, an alkoxy group, an acyloxy group, an acyl group, an alkenyl group, an alkynyl group, an aryl group, an alkylthio group, an alkoxycarbonyl group, an alkylsulfinyl group, an alkylsulfonyl group, an amino group, and an alkylamino group; and X represents a carboxylic acid group or a carboxylate group, or any pharmaceutically acceptable salt thereof; with the provisos that:
the compound of formula (I) is not (all-Z)-4,7,10,13,16,19-docosahexaenoic acid (DHA), alpha-methyl DHA, alpha-methyl DHA methyl ester, alpha-methyl DHA ethyl ester, or alpha-hydroxy DHA ethyl ester, and $R_1$ and $R_2$ are not simultaneously a hydrogen atom.

9. The method according to claim 1, wherein $R_1$ is hydrogen and $R_2$ is an alkyl group.

10. The method according to claim 9, wherein the alkyl group is a propyl group.

11. The method according to claim 1, wherein X is a carboxylate group.

12. The method according to claim 11, wherein the carboxylate group is ethyl carboxylate.

13. The method according to claim 1, wherein X is a carboxylic acid group.

14. A pharmaceutical composition comprising a compound of formula (I):

wherein $R_1$ and $R_2$ are the same or different and are chosen from a hydrogen atom, an alkyl group, a halogen atom an alkoxy group, an acyloxy group, an acyl group, an alkenyl group, an alkynyl group, an aryl group, an alkylthio group, an alkoxycarbonyl group, an alkylsulfinyl group, an alkylsulfonyl group, an amino group, and an alkylamino group; and X represents a carboxylic acid group or a carboxylate group, or any pharmaceutically acceptable salt thereof;

with the provisos that:

the compound of formula (I) is not (all-Z)-4,7,10,13,16, 19-docosahexaenoic acid (DHA), alpha-methyl DHA, alpha-methyl DHA methyl ester, alpha-methyl DHA ethyl ester, or alpha-hydroxy DHA ethyl ester, and $R_1$ and $R_2$ are not simultaneously a hydrogen atom.

15. A pharmaceutical composition comprising a compound of formula (I):

wherein $R_1$ and $R_2$ are the same or different and are chosen from a hydrogen atom, a hydroxy group, an alkyl group, a halogen atom, an alkoxy group, and acyloxy group, an acyl group, an alkenyl group, an alkynyl group, an aryl group, and alkylthio group, an alkoxycarbonyl group, an alkylsulfinyl group, an alkylsulfonyl group, an amino group, or an alkylamino group; and X represents a carboxylic acid group, or any pharmaceutically acceptable salt thereof;

with the provisos that:

the compound of formula (I) is not (all-Z)-4,7,10,13,16, 19-docosahexaenoic acid (DHA), alpha-methyl DHA, alpha-methyl DHA methyl ester, alpha-methyl DHA ethyl ester or alpha-hydroxy DHA ethyl ester, and $R_1$ and $R_2$ are not simultaneously a hydrogen atom.

16. A pharmaceutical composition comprising a compound of formula (I):

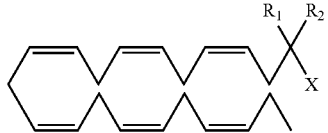

wherein $R_1$ and $R_2$ are the same or different and are chosen from a hydrogen atom, a hydroxy group, an alkyl group, a halogen atom, an alkoxy group, and acyloxy group, an acyl group, an alkenyl group, an alkynyl group, an aryl group, andalkylthio group, an alkoxycarbonyl group, an alkylsulfinyl group, an alkylsulfonyl group, an amino group, or an alkylamino group; and X represents a carboxylic acid group, wherein the carboxylic acid is present as its diglyceride derivative;

with the provisos that:

the compound of formula (I) is not (all-Z)-4,7,10,13,16,10, 19-docosahexaenoic acid (DHA), alpha-methyl DHA, alpha-methyl DHA methyl ester, alpha-methyl DHA ethyl ester or alpha-hydroxy DHA ethyl ester, and $R_1$ and $R_2$ are not simultaneously a hydrogen atom.

17. The method according to claim 1, wherein $R_1$ and $R_2$ are both alkyl groups.

18. The method according to claim 17, wherein $R_1$ and $R_2$ are both ethyl groups.

19. The method according to claim 3, wherein $R_1$ is hydrogen and $R_2$ is an alkyl group.

20. The method according to claim 19, wherein the alkyl group is a propyl group.

21. The method according to claim 3, wherein X is a carboxylate group.

22. The method according to claim 3, wherein the carboxylate group is ethyl carboxylate.

23. The method according to claim 3, wherein X is a carboxylic acid group.

24. The method according to claim 6, wherein $R_1$ is hydrogen and $R_2$ is an alkyl group.

25. The method according to claim 24, wherein the alkyl group is a propyl group.

26. The method according to claim 6, wherein X is a carboxylate group.

27. The method according to claim 6, wherein the carboxylate group is ethyl carboxylate.

28. The method according to claim 6, wherein X is a carboxylic acid group.

29. The method according to claim 6, wherein $R_1$ and $R_2$ are both alkyl groups.

30. The method according to claim 6, wherein $R_1$ and $R_2$ are both ethyl groups.

31. The method according to claim 7, wherein $R_1$ is hydrogen and $R_2$ is an alkyl group.

32. The method according to claim 31, wherein the alkyl group is a propyl group.

33. The method according to claim 7, wherein X is a carboxylate group.

34. The method according to claim 7, wherein the carboxylate group is ethyl carboxylate.

35. The method according to claim 7, wherein X is a carboxylic acid group.

36. The method according to claim 7, wherein $R_1$ and $R_2$ are both alkyl groups.

37. The method according to claim 7, wherein $R_1$ and $R_2$ are both ethyl groups.

38. The method according to claim 8, wherein $R_1$ is hydrogen and $R_2$ is an alkyl group.

39. The method according to claim 38, wherein the alkyl group is a propyl group.

40. The method according to claim 8, wherein X is a carboxylate group.

41. The method according to claim 8, wherein the carboxylate group is ethyl carboxylate.

42. The method according to claim 8, wherein X is a carboxylic acid group.

43. The method according to claim 8, wherein $R_1$ and $R_2$ are both alkyl groups.

44. The method according to claim 8, wherein $R_1$ and $R_2$ are both ethyl groups.

45. A pharmaceutical composition according to claim 14, wherein the compound of formula I is (4Z,7Z,10Z,13Z,16Z,19Z)-2-ethyldocosa-4,7,10,13,16,19-hexaenoate.

46. The method according to claim 3, wherein the dyslipidemia is hypertriglyceridemia.

47. A method of reducing blood cholesterol by administering to a human or animal patient in need thereof a pharmaceutically effective amount of a compound of the following formula:

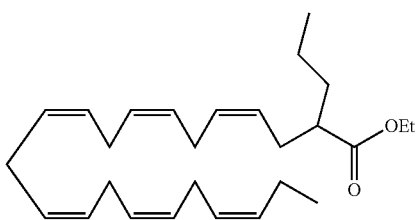 [SMILES: CC/C=C\C/C=C\C/C=C\C/C=C\C/C=C\C/C=C\CC(CCC)C(=O)OCC]

ethyl(4Z,7Z,10Z,13Z,16Z,19Z)-2-propyldocosa-4,7,10,13,16,19-hexaenoate.

48. A method of reducing blood cholesterol by administering to a human or animal patient in need thereof a pharmaceutically effective amount of a compound of the following formula:

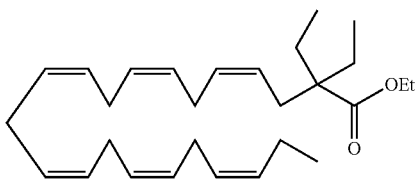

ethyl(4Z,7Z,10Z,13Z,16Z,19Z)-2,2-diethyldocosa-4,7,10,13,16,19-hexaenoate.

49. A method of elevating HDL cholesterol levels in the serum by administering to a human or animal patient in need thereof a pharmaceutically effective amount of the following formula:

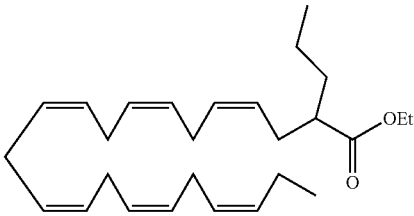

ethyl(4Z,7Z,10Z,13Z,16Z,19Z)-2-propyldocosa-4,7,10,13,16,19-hexaenoate.

50. A method of elevating HDL cholesterol levels in the serum by administering to a human or animal patient in need thereof a pharmaceutically effective amount of the following formula:

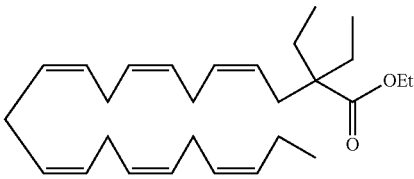 [SMILES: CC/C=C\C/C=C\C/C=C\C/C=C\C/C=C\C/C=C\CC(CC)(CC)C(=O)OCC]

ethyl(4Z,7Z,10Z,13Z,16Z,19Z)-2,2-diethyldocosa-4,7,10,13,16,19-hexaenoate.

* * * * *

UNITED STATES PATENT AND TRADEMARK OFFICE
CERTIFICATE OF CORRECTION

| | | |
|---|---|---|
| PATENT NO. | : 8,618,165 B2 | Page 1 of 1 |
| APPLICATION NO. | : 13/225855 | |
| DATED | : December 31, 2013 | |
| INVENTOR(S) | : Morten Bryhn et al. | |

It is certified that error appears in the above-identified patent and that said Letters Patent is hereby corrected as shown below:

In the Claims

Claim 1, column 50, line 62, "aikynyl" should read -- alkynyl --.

Claim 3, column 51, line 32, "formula (I) not" should read -- formula (I) is not --.

Claim 15, column 53, line 43, "and alkylthio group" should read -- an alkylthio group --.

Claim 16, column 54, line 1, "andalkylthio group" should read -- an alkylthio group --.

Claim 16, column 54, line 7, "4,7,10,13,16,10,19-" should read -- 4,7,10,13,16,19- --.

Signed and Sealed this
Twenty-second Day of April, 2014

Michelle K. Lee
*Deputy Director of the United States Patent and Trademark Office*